US009732382B2

(12) United States Patent
Yue et al.

(10) Patent No.: US 9,732,382 B2
(45) Date of Patent: *Aug. 15, 2017

(54) PHOTODAMAGE MITIGATION COMPOUNDS AND SYSTEMS

(71) Applicant: Pacific Biosciences of California, Inc., Menlo Park, CA (US)

(72) Inventors: Stephen Yue, Eugene, OR (US); Robert Weber, San Francisco, CA (US); Xiangxu Kong, Union City, CA (US); Andrei Fedorov, San Bruno, CA (US); John Lyle, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 351 days.

This patent is subject to a terminal disclaimer.

(21) Appl. No.: 14/456,590

(22) Filed: Aug. 11, 2014

(65) Prior Publication Data

US 2015/0079603 A1 Mar. 19, 2015

Related U.S. Application Data

(63) Continuation of application No. 13/208,151, filed on Aug. 11, 2011, now Pat. No. 8,834,847.

(60) Provisional application No. 61/401,471, filed on Aug. 12, 2010, provisional application No. 61/466,734, filed on Mar. 23, 2011.

(51) Int. Cl.
*C12Q 1/68* (2006.01)
*G01N 33/52* (2006.01)
*C12Q 1/25* (2006.01)
*G01N 33/543* (2006.01)
*C12N 13/00* (2006.01)

(52) U.S. Cl.
CPC ........... *C12Q 1/6869* (2013.01); *C12N 13/00* (2013.01); *C12Q 1/25* (2013.01); *G01N 33/52* (2013.01); *G01N 33/54373* (2013.01); *G01N 2333/916* (2013.01); *G01N 2333/91245* (2013.01)

(58) Field of Classification Search
None
See application file for complete search history.

(56) References Cited

U.S. PATENT DOCUMENTS

| | | | |
|---|---|---|---|
| 2,511,428 A | 6/1950 | Buston et al. | |
| 3,986,980 A | 10/1976 | Cort | |
| 4,003,919 A | 1/1977 | Scott et al. | |
| 4,302,569 A | 11/1981 | Halle et al. | |
| 4,619,666 A | 10/1986 | Rose et al. | |
| 4,689,307 A | 8/1987 | Schwartz | |
| 4,979,824 A | 12/1990 | Mathies et al. | |
| 5,242,835 A | 9/1993 | Jensen | |
| 5,331,004 A | 7/1994 | Denny et al. | |
| 5,476,849 A | 12/1995 | Ulrich et al. | |
| 5,514,676 A | 5/1996 | Ulrich et al. | |
| 5,547,839 A | 8/1996 | Dower et al. | |
| 5,674,716 A | 10/1997 | Tabor et al. | |
| 5,821,058 A | 10/1998 | Smith et al. | |
| 5,866,331 A | 2/1999 | Singer et al. | |
| 6,068,848 A | 5/2000 | Gubernick et al. | |
| 6,190,685 B1 | 2/2001 | Karita | |
| 6,210,896 B1 | 4/2001 | Chan | |
| 6,296,810 B1 | 10/2001 | Ulmer | |
| 6,544,797 B1 | 4/2003 | Buechler et al. | |
| 6,818,395 B1 | 11/2004 | Quake et al. | |
| 6,869,764 B2 | 3/2005 | Williams et al. | |
| 6,953,659 B2 | 10/2005 | Jacobson et al. | |
| 6,982,146 B1 | 1/2006 | Schneider et al. | |
| 7,033,762 B2 | 4/2006 | Nelson et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,064,197 B1 | 6/2006 | Rabbani et al. | |
| 7,235,357 B2 | 6/2007 | Iwaki | |
| 7,351,397 B2 | 4/2008 | Cyr | |
| 7,993,895 B2 | 8/2011 | Eid et al. | |
| 2002/0037479 A1 | 3/2002 | Schwartzkopf et al. | |
| 2002/0064524 A1 | 5/2002 | Cevc | |
| 2002/0100896 A1 | 8/2002 | Koizumi et al. | |
| 2002/0102595 A1 | 8/2002 | Davis | |
| 2002/0156037 A1 | 10/2002 | Volkin et al. | |
| 2003/0044781 A1 | 3/2003 | Korlach et al. | |
| 2003/0044830 A1 | 3/2003 | Iwaki | |
| 2003/0087259 A1 | 5/2003 | Clancy et al. | |
| 2003/0124576 A1 | 7/2003 | Kumar et al. | |

(Continued)

FOREIGN PATENT DOCUMENTS

| | | |
|---|---|---|
| EP | 428000 A1 | 5/1991 |
| EP | 1105529 BI | 11/2005 |
| WO | 91/06678 | 5/1991 |
| WO | 96/27025 | 9/1996 |
| WO | 99/05315 | 2/1999 |
| WO | 00/36152 | 6/2000 |
| WO | 01/16375 A2 | 3/2001 |
| WO | 2009/100382 A1 | 8/2009 |

OTHER PUBLICATIONS

Debey et al., Israel J. Chem. (1970) 8:115-123.
Dittrich et al., "Photobleaching and stabilization of fluorophores used for single-molecule analysis with one-and two-photon excitation" Appl Phys B (2001) 73:829-837.

(Continued)

*Primary Examiner* — Michael G Hartley
*Assistant Examiner* — Jennifer Lamberski
(74) *Attorney, Agent, or Firm* — David C. Scherer; Deana A. Arnold

(57) ABSTRACT

Compositions, devices, systems and methods for reducing and/or preventing photo-induced damage of one or more reactants in an illuminated analytical reaction by addition of one or more photoprotective compounds to the reaction mixture and allowing the reaction to proceed for a period that is less than a photo-induced damage threshold period.

16 Claims, 15 Drawing Sheets

(56) References Cited

U.S. PATENT DOCUMENTS

| | | |
|---|---|---|
| 2003/0129642 A1 | 7/2003 | Buechler et al. |
| 2003/0174992 A1 | 9/2003 | Levene et al. |
| 2003/0186276 A1 | 10/2003 | Odera |
| 2003/0190647 A1 | 10/2003 | Odera |
| 2003/0194740 A1 | 10/2003 | Williams |
| 2003/0215862 A1 | 11/2003 | Parce et al. |
| 2004/0048301 A1 | 3/2004 | Sood et al. |
| 2004/0170585 A1 | 9/2004 | Berens et al. |
| 2004/0224319 A1 | 11/2004 | Sood et al. |
| 2005/0026847 A1 | 2/2005 | Jacobs et al. |
| 2005/0141843 A1 | 6/2005 | Warden et al. |
| 2005/0148027 A1 | 7/2005 | Pirrung et al. |
| 2005/0233399 A1 | 10/2005 | Aebersold et al. |
| 2005/0271705 A1 | 12/2005 | Hughes et al. |
| 2006/0019267 A1 | 1/2006 | Quake |
| 2006/0210440 A1 | 9/2006 | Potyrailo et al. |
| 2006/0229407 A1 | 10/2006 | Vogel et al. |
| 2007/0128133 A1 | 6/2007 | Eid et al. |
| 2007/0161017 A1 | 7/2007 | Eid et al. |
| 2007/0167458 A1 | 7/2007 | Bouchon et al. |
| 2008/0176241 A1 | 7/2008 | Eid et al. |
| 2008/0176316 A1 | 7/2008 | Eid et al. |
| 2008/0299565 A1 | 12/2008 | Schneider et al. |
| 2009/0202993 A1 | 8/2009 | Lagunavicius et al. |
| 2009/0325260 A1 | 12/2009 | Otto et al. |
| 2010/0136592 A1 | 6/2010 | Kong et al. |

OTHER PUBLICATIONS

Giloh, H. et al., "Fluorecence microscopy: reduced photobleaching of rhodarnine and fluorescein protein conjugates by n-propyl gallate" Science (1982) 217:1252-1255.
Kapanidis et al., J. Chem. Phys (2002) 117(25)10953-10964.
Levene et al. "Zero-mode waveguides for single-molecule analysis at high concentrations" Science (2003) 299:682-686.
Piston et al., "Molecular expressions optical microscopy primer: specialized techniques" webpage (2004) http://www.microscopy.fsu.edu/primer/techniques/fluorescence/multiphoton/multiphotonintro.html.
Song, L. et al., "Influence of the triplet excited statea on the photobleaching kinetics of fluorescein in the microscopy" Biophys J (1996) 70(6):5969-2968.
Subramanyam, R. et al., "Protective effect of active oxygen scavengers on protein degradation and photochemical function in photosystem I submembrane fractions during light stress" FEBS J. (2005) 272(4):892-902.
Van Dijk et al., J. Phys. Chem. B (2004) 108:6479-6484.
Derwent Abstract (English) for JP 02123303 downloaded Apr. 20, 2009.
Barra et al. "Triplet State Dynamics within Cyclodextrin Solid Complexes" Arkivoc (2003) 4:48-58.
Chen et al, "Anti-inflammatory Benzenoids from Antrodia camphorate" J. Natural Products (2007) 70(6):989-992.
Chen et al. "Benzopyrans, Biphenyls and Xanthones from the Root of Garcinia Linii and Their Activity Against *Mycobacterium tuberculosis*" Plant Medica (2006) 72:473-477.
Chen et al. "New Cytotoxic Tetrahydrofuran- and Dyhudrofuan-Type Ligands from the Stem of BEilSchmiedia Tsangii" Plant Medica (2006) 72:351-357.
Chen et al. "Tocopherols and Triterpenoids from Side Acute" J. Chinese Chem Soc (2007) 54(1):41-45.
Chiang et al. "Two novel alpha-tocopheroids from the Aerial Roots of Ficus Microcarpa" Tetrahedron Lett (2003) 44(27):5125-5128.

Cordes et al. "On the mechanism of Trolox and antiblinking and antibleaching reagent" J Am Chem Soc (2009) 131:5018-5019.
D'Ischia et al. "Dye-sensitized photooxidation of vitamin E revisted. New 7-Oxaspiro[4. Sidec-1-ene-3,6-dione products by oxygenation and ring contraction of alpha-tocopherol" J Am Chem Soc (1991) 113-8353-8356.
Friaa et al. "Kinetics of the reaction between the antioxidant trolox and the free radical DPPH m semi-aqueous solution" Org Biomol Chem (2006) 4:2417-2423.
Gao et al. "Chemical constituents from leaves of allelopathic cultivar sunflower in China" Chem Nat Compounds (2008) 44(6):713-775.
Gazdaru, D. "Characterization of the fluorescence quencing of chlorophyll a by 1,4 benzaquinone using the nonlinear analysis" J Optoelec Adv Mat (2001) 3(1):145-148.
Grams, G.W. "Oxidation of alpha-tocopherol by singlet oxygen" Tetrahedron Lett (1971) 50:4823-4825.
Ham et al. "Antioxidant reactions of vitamin E in the perfused rat liver: Product distribution and effect of dietary vitamin E supplementation" Archives of Biochem & Biophys (1997) 339(1)157-164.
Kitajima, J. et al. "Constituents of Ficus pumila leaves" Chem Pharm Bull (1998) 46(10):1647-1649.
Lin et al. "Anti-platelet aggregation and chemical constituents from the rhizome of Gyura Japonica" Plant Medica (2003) 69:757-764.
Matsuo et al. "Oxygenations of Vitamin E (alpha-tocopherol) and its model compound 2,2,5,7,8-pentamethylchroman-6-0i1n in the presence of the superoxide radical solubilized in aprotic solvents: unique epoxidation and recyclizatoins" J Org Chem (1987) 52:3514-3520.
Nonell, S. et al. "Solvent influence on the kinetics of the photodynamic degradation of trolox, a water-soluble model compound for Vitamin E" J Photochm & Photobiology B: Biology (1995) 29:157-162.
Rasnik et al. "Nonblinking and Longlasting Single-Molecule Fluroescence Imaging" Nature Methods (2006) 3 (11):891-893.
Sapino et al. "On the complexation of trolox with Methy-b-Cyclodextrin: Characterization, Molecular Modeling and Photostabilizing Properties" J Incl Phenom Macrocycl Chem (2008) 62(1-2):179-186.
Schwille, H.E. "Fluorescence correlation spectroscopy. An introduction to its concepts and applications" Biophys Textbook Online (2001) pp. 1-33.
Acree et al. "Absorption and Luminescence Probes," Encyclopedia of Analytical Chemistry (2006) 1-25.
Chowhan, "pH-Solubility Profiles of Organic Carboxylic Acids and Their Salts," J. Pharm Set. (1978) 67:1257-1260.
Drewe et al., "Rational Design of Substituted Diarylureas: A Scaffold for Binding to G-Quadruplex Motifs," J. Med. Chem. (2008) 51:7751-7767.
Matsumoto, "Photoreduction of Methylene Blue by Some Derivatives of N-Phenyl-glycine. Relation Between the Structure and the Reactivity of the Electron Donors," Bulletin of the Chemical Society of Japan (1962) 35:1860-1866.
Sugimori et al., "Synthesis and Antitumor Activity fo Ring A- and F-Modified Hexacyclic Camptothecin Analogues," J. Med. Chem. (1998) 41:2308-2318.
Tuttle, "Synthesis of Phenylanthranilic Acids," J. Am. Chem. Soc. (1921) 45:1906-1916.
Vogelsang et al., "Controlling the Fluoresence of Ordinary Oxazine Dyes for Single-Molecule Switching and Superresolution Microscopy," Proc. Natl. Acad. Scie. USA (2009) 106:8107-8112.
International Search Report and Written Opinion dated Mar. 19, 2012 for related case PCT/US2011/047468.
International Preliminary Report on Patentability dated Feb. 21, 2013 for related case PCT/US2011/047468.

A.

B.

C.

Negative control

A.

B.

C.

D.

PHOTODAMAGE MITIGATION COMPOUNDS AND SYSTEMS

CROSS-REFERENCE TO RELATED APPLICATIONS

This application is a continuation of U.S. patent application Ser. No. 13/208,151 filed Aug. 11, 2011, which claims priority from Provisional U.S. Patent Application No. 61/401,471, filed Aug. 12, 2010; and Provisional U.S. Patent Application No. 61/466,734, filed Mar. 23, 2011, the full disclosures of which are incorporated herein by reference in their entireties for all purposes.

STATEMENT REGARDING FEDERALLY SPONSORED RESEARCH

Not Applicable.

BACKGROUND OF THE INVENTION

The use of optically detectable labeling groups, and particularly those groups having high quantum yields, e.g., fluorescent, phosphorescent, luminescent or chemiluminescent groups, is ubiquitous throughout the fields of analytical chemistry, biochemistry, and biology. In particular, by providing a highly visible signal associated with a given reaction, one can better monitor that reaction as well as any potential effectors of that reaction. Such analyses are the basic tools of life science research in genomics, diagnostics, pharmaceutical research, and related fields.

Such analyses have generally been performed under conditions where the amounts of reactants are present far in excess of what is required for the reaction in question. The result of this excess is to provide ample detectability, as well as to compensate for any damage caused by the detection system and allow for signal detection with minimal impact on the reactants. For example, analyses based on fluorescent labeling groups generally require the use of an excitation radiation source directed at the reaction mixture to excite the fluorescent labeling group, which is then separately detectable. However, one drawback to the use of optically detectable labeling groups is that prolonged exposure of chemical and biochemical reactants to such light sources, alone, or when in the presence of other components, e.g., the fluorescent groups, can damage such reactants, e.g., proteins, enzymes, and the like. The traditional solution to this drawback is to have the reactants present so far in excess that the number of undamaged reactant molecules far outnumbers the damaged reactant molecules, thus minimizing or negating the effects of the photo-induced damage.

A variety of analytical techniques currently being explored deviate from the traditional techniques. In particular, many reactions are based on increasingly smaller amounts of reagents, e.g., in microfluidic or nanofluidic reaction vessels or channels, or in "single molecule" analyses. Such low reactant volumes are increasingly important in many high throughput applications, such as microarrays.

The use of smaller reactant volumes offers challenges to the use of optical detection systems. When smaller reactant volumes are used, damage to reactants, such as from exposure to light sources for fluorescent detection, can become problematic and have a dramatic impact on the operation of a given analysis. This can be particularly detrimental, for example, in real time analysis of reactions that include fluorescent reagents that can expose multiple different reaction components to optical energy. In addition, smaller reactant volumes can lead to limitations in the amount of signal generated upon application of optical energy.

As such, methods and compositions that result in increased effective concentrations of reactants and detection molecules in smaller reactant volumes, thereby increasing signal in a smaller volume, would provide useful improvements to the methods and compositions currently available. For example, methods and compositions that prevent or mitigate to some extent photo-induced damage in a reaction of interest would be particularly useful.

BRIEF SUMMARY OF THE INVENTION

The present invention is generally directed to compounds, compositions, methods, devices and systems for preventing, reducing, or limiting the effects of photo-induced damage during illuminated reactions, particularly reactions that employ fluorescent or fluorogenic reactants. The term "photo-induced damage" refers generally to any direct or indirect impact of illumination on one or more reagents in a reaction resulting in a negative impact upon that reaction. The term "illuminated reactions" as used herein refers to reactions which are exposed to an optical energy source. Typically, such illumination is provided in order to observe the generation and/or consumption of reactants or products that possess a particular optical characteristic indicative of their presence, such as an alteration (in intensity, wavelength, etc.) in the absorbance spectrum and/or emission spectrum of the reaction mixture or its components.

In a first aspect, the invention provides reaction mixtures that include a fluorescent or fluorogenic molecule, and a photoprotective agent, the photoprotective agent including a reducing unit covalently bound to an oxidizing unit. In certain preferred embodiments, the photoprotective agent further comprises a water solubilizing unit. Optionally included in the mixtures is a nucleoside polyphosphate (or analog thereof) and/or an enzyme, e.g., a polymerase or ligase enzyme. The mixtures can further include a template nucleic acid molecule. At least one component of the reaction mixture can be confined within a zero mode waveguide. Preferably, at least one component of the reaction mixture is linked to a fluorescent or fluorogenic molecule. In certain specific embodiments, one component of the reaction mixture is a fluorescently labeled enzyme, nucleotide polyphosphate, polynucleotide, tRNA, amino acid, or analog thereof.

Reaction mixtures of the invention preferably include a photoprotective agent that reduces an amount of photo-induced damage to one or more reaction components that would otherwise occur in the absence of the photoprotective agent. In preferred embodiments, the photoprotective agent is a single molecule reducing and oxidizing system, a nitrobenzene derivative (e.g., nitrobenzoic acid or a derivative thereof), and the like. The reducing unit can include, e.g., one or more of a thiol group, a disulfide group, ascorbic acid, an ascorbic acid derivative, dialkylaniline, a dialkylaniline derivative, anthracene, an anthracene derivative, an aliphatic amine, and/or an aromatic amine. The oxidizing unit can include, e.g., one or more of a nitro group, a quinone or derivative thereof, a hydroquinone or derivative thereof, methylviologen, a methylviologen derivative, a nitrobenzene derivative, nitrobenzoic acid, or a nitrobenzoic acid derivative. Alternatively, in some preferred embodiments the photoprotective agent does not comprise a quinone, hydroquinone, or a derivative thereof. Optionally, the reaction mixtures include a photoprotective agent that includes a compound of a formula selected from the group consisting of:

-continued
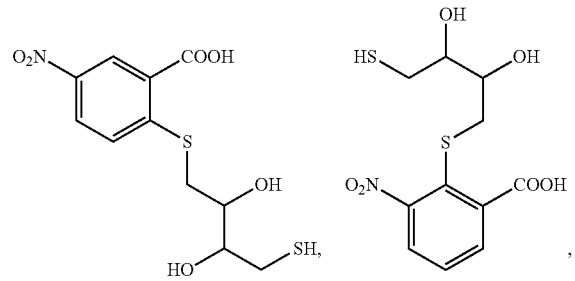
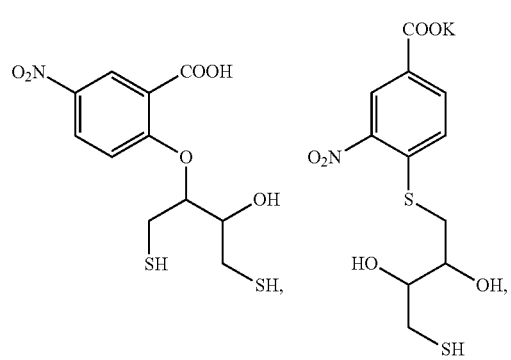
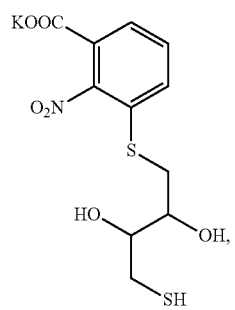
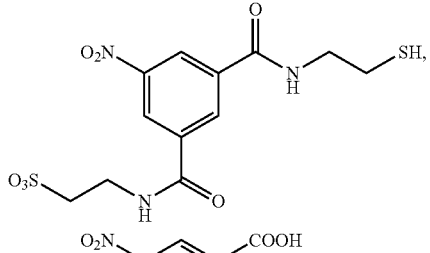
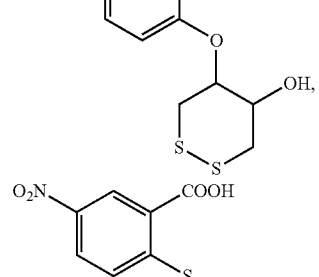
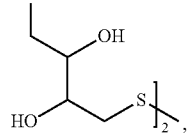
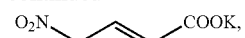
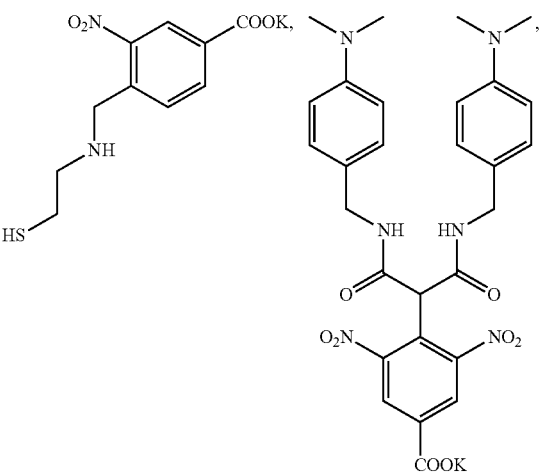
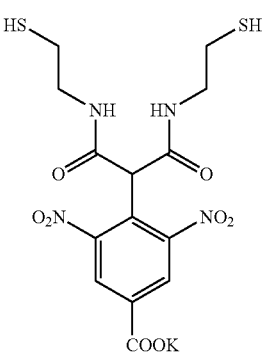
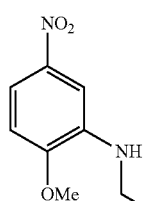
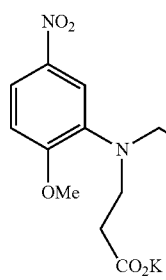
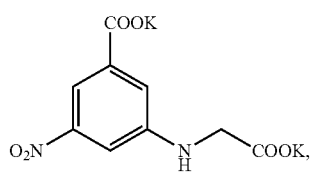
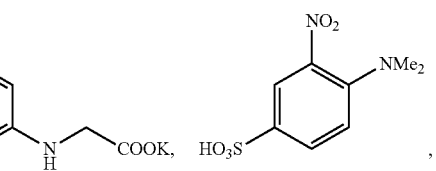

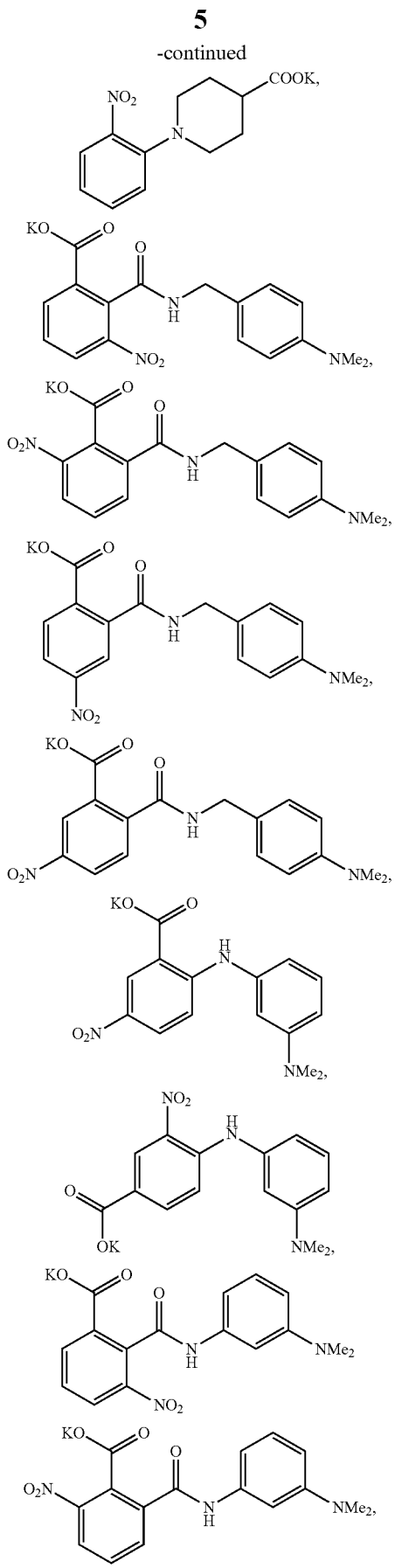
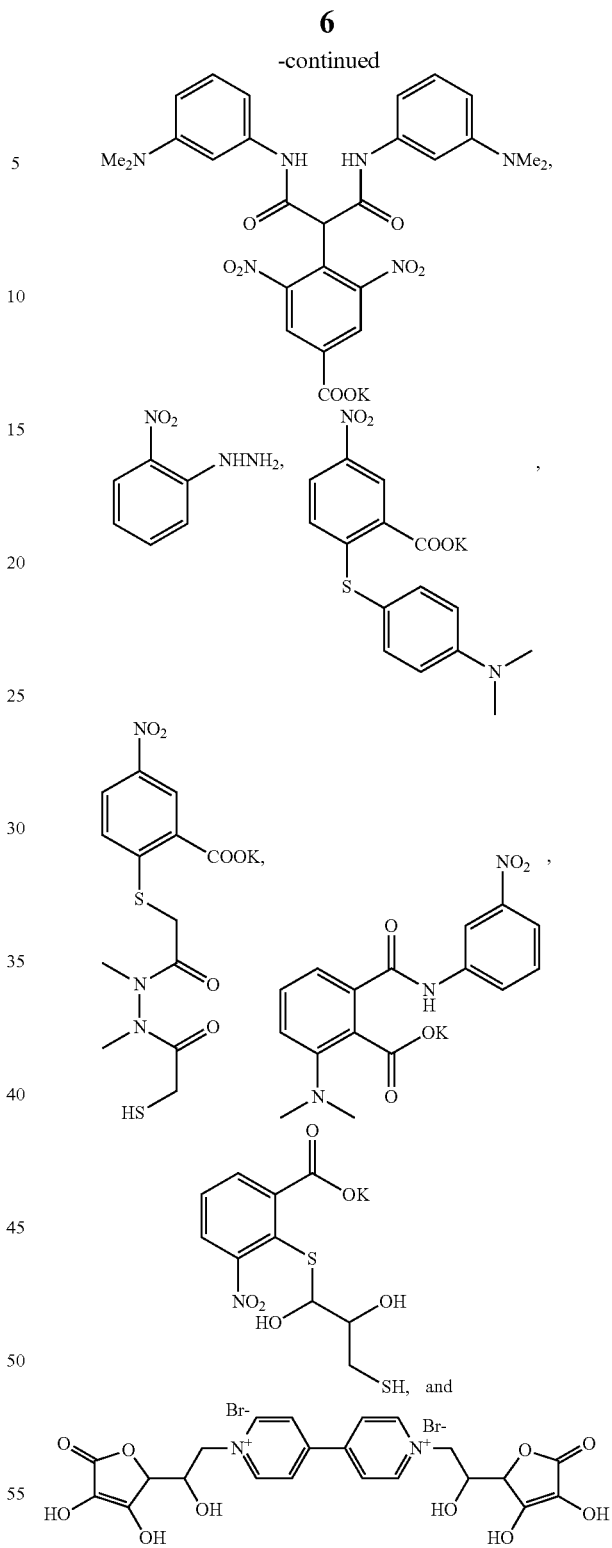

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., K+) illustrated).

In a related aspect, the invention provides reaction mixtures that include a first reactant, a second reactant comprising a fluorescent or fluorogenic label, and a photoprotective agent, the photoprotective agent including a reducing unit covalently bound to an oxidizing unit. In certain preferred embodiments, the photoprotective agent further comprises a water solubilizing unit. Here, interaction of the first and second reactants under excitation illumination causes photo-induced damage to the first reactant in the absence of the photoprotective agent, which reduces an amount of photo-induced damage to at least the first reactant. Optionally, the first reactant is a polymerase, ligase, nuclease, or a ribosome. The reaction mixtures optionally include a photoprotective agent that is a single molecule reducing and oxidizing system, e.g., a nitrobenzene derivative (e.g., nitrobenzoic acid or a derivative thereof), and the like. The reducing unit can include, e.g., one or more of a thiol group, a disulfide group, ascorbic acid, an ascorbic acid derivative, dialkylaniline, a dialkylaniline derivative, anthracene, an anthracene derivative, an aliphatic amine, and/or an aromatic amine. The oxidizing unit can include, e.g., one or more of a nitro group, a quinone, a quinone derivative, methylviologen, a methylviologen derivative, a nitrobenzene derivative, nitrobenzoic acid, or a nitrobenzoic acid derivative. Alternatively, in some preferred embodiments the photoprotective agent does not comprise a quinone, hydroquinone, or a derivative thereof. Optionally, reaction mixtures in this aspect of the invention include a photoprotective agent that includes a compound of a formula selected from the group consisting of:

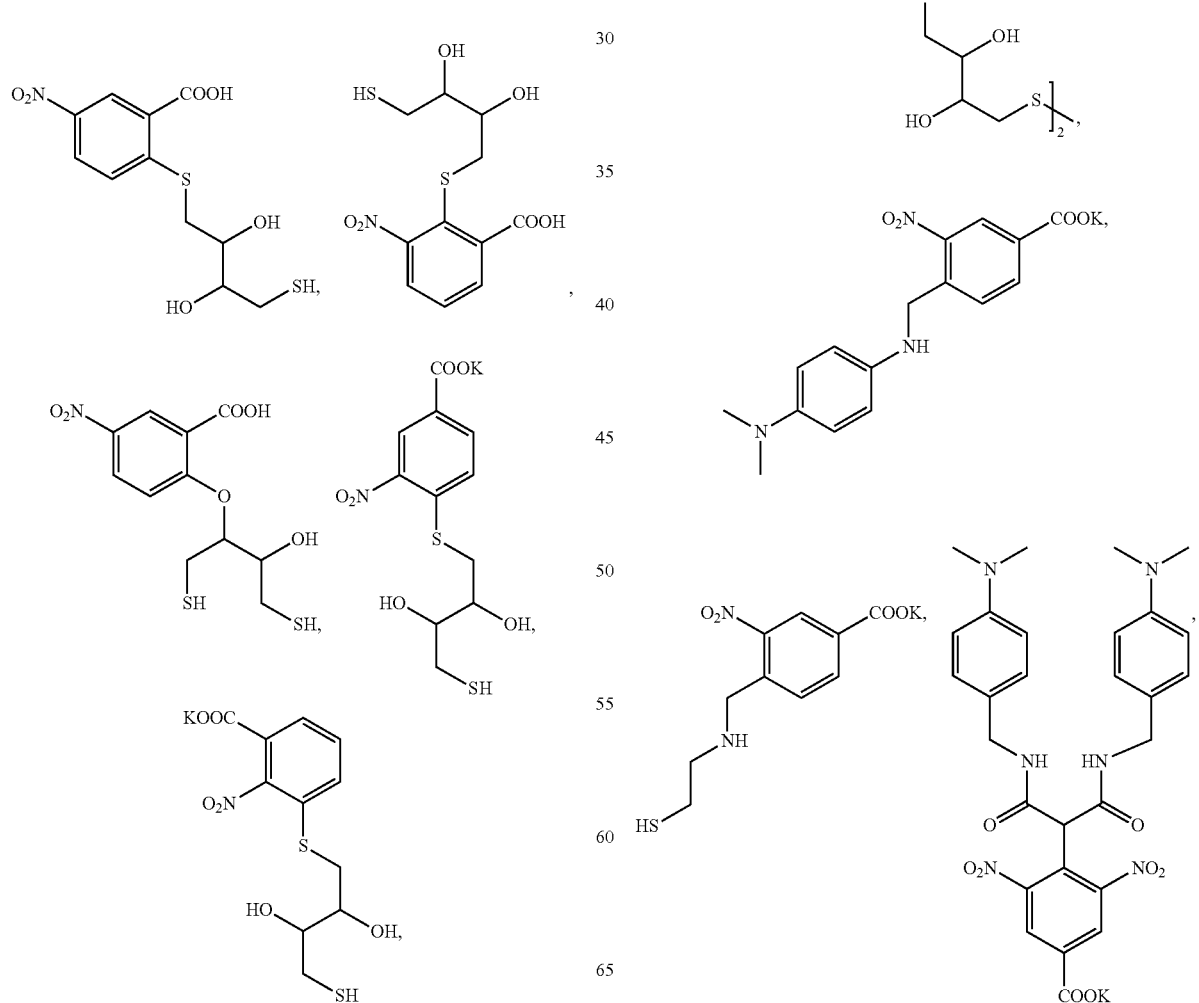

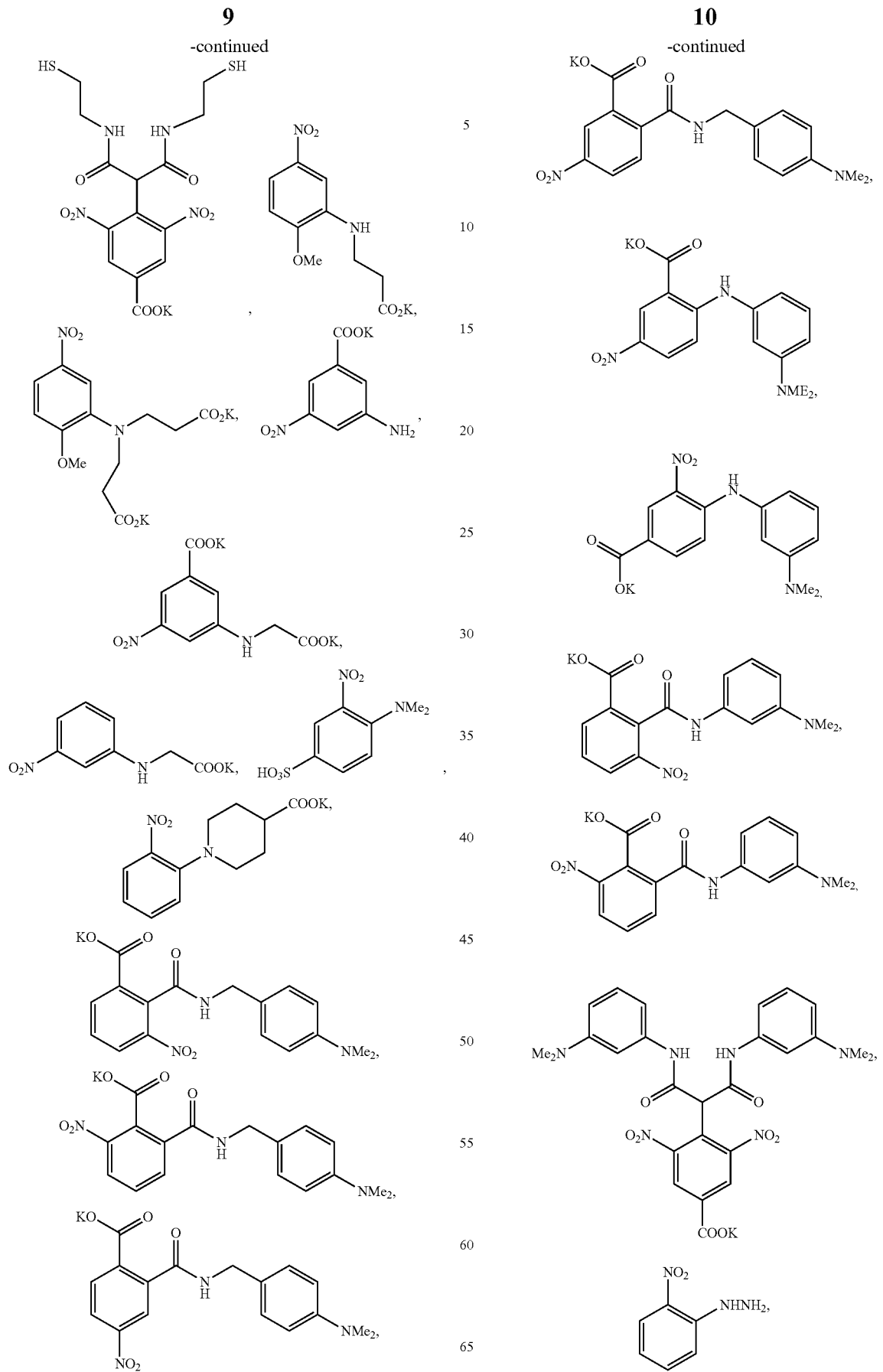

-continued

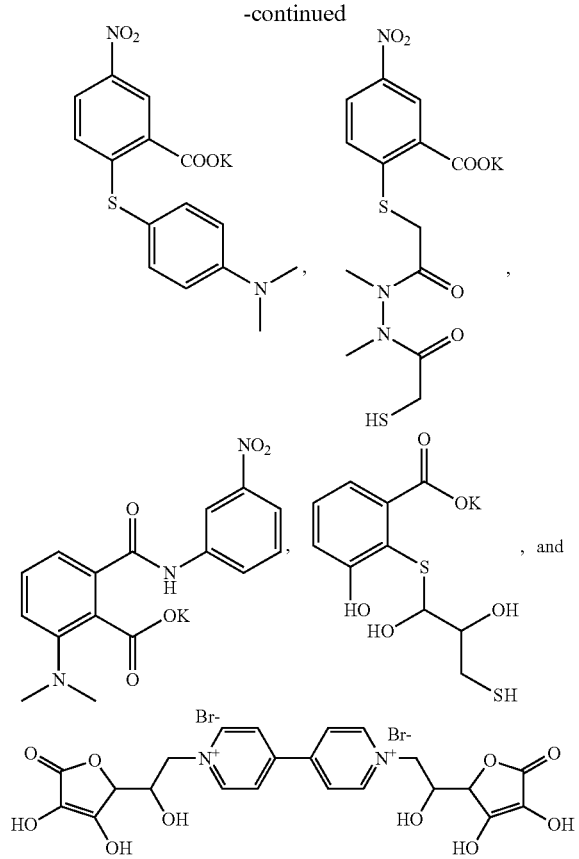

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., K⁺) illustrated).

Reaction mixtures that include a polymerase, nuclease, or ligase enzyme can further include a template nucleic acid molecule and/or a nucleoside polyphosphate or analog thereof. Reaction mixtures that include a ribosome can further include mRNA, tRNA, amino acids, and other reactants typically included in a translation reaction. Optionally, at least one component of the reaction mixture is confined within a zero mode waveguide.

Methods for protecting an enzyme from photo-induced damage in an illuminated reaction are also provided by the present invention. The methods include providing a reaction mixture that includes the enzyme and a fluorescent or fluorogenic substrate for the enzyme. Interaction of the enzyme and the fluorescent or fluorogenic substrate under excitation illumination results in altered activity of the enzyme. Such interaction may be a covalent or noncovalent interaction, binding interaction, a transient interaction, a catalytic interaction, and the like. In accordance with the methods of the invention, the reaction mixtures can further include a template nucleic acid molecule and/or a nucleoside polyphosphate or analog thereof. Optionally, at least one component of the reaction mixture is confined within a zero mode waveguide.

The methods further comprise adding a photoprotective agent to the reaction mixture, the photoprotective agent including a reducing unit covalently bound to an oxidizing unit (e.g., a single molecule reducing and oxidizing system). In certain preferred embodiments, the photoprotective agent further comprises a water solubilizing unit. In preferred embodiments, the photoprotective agent is a nitrobenzene derivative (e.g., nitrobenzoic acid or a derivative thereof). The reducing unit can include, e.g., one or more of a thiol group, a disulfide group, ascorbic acid, an ascorbic acid derivative, dialkylaniline, a dialkylaniline derivative, anthracene, an anthracene derivative, an aliphatic amine, and/or an aromatic amine. The oxidizing unit can include, e.g., one or more of a nitro group, a quinone or derivative thereof, a hydroquinone or derivative thereof, methylviologen, a methylviologen derivative, a nitrobenzene derivative, nitrobenzoic acid, or a nitrobenzoic acid derivative. Alternatively, in some preferred embodiments the photoprotective agent does not comprise a quinone, hydroquinone, or a derivative thereof. Optionally, the reaction mixtures include a photoprotective agent that includes a compound of a formula selected from the group consisting of:

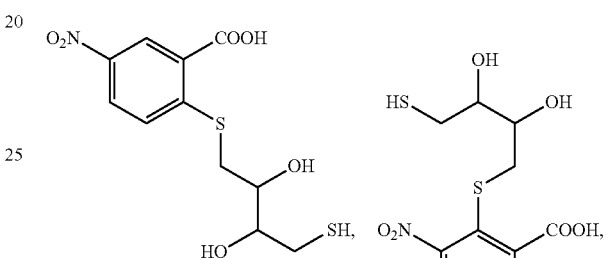

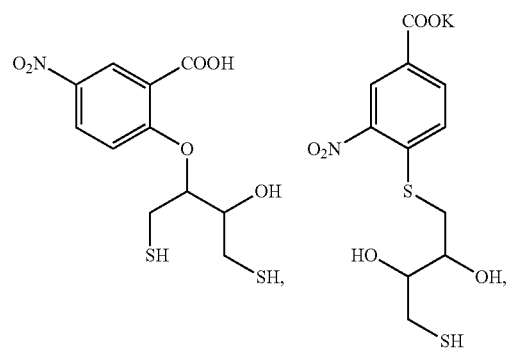

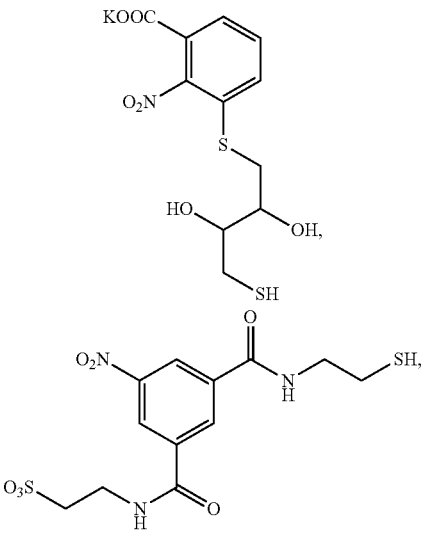

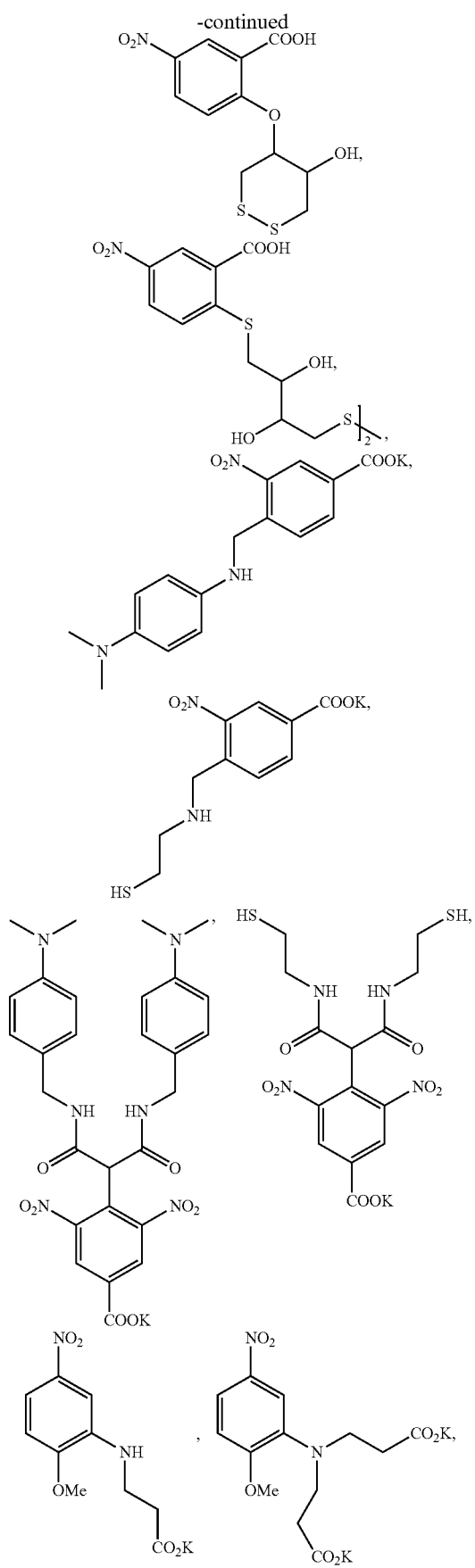
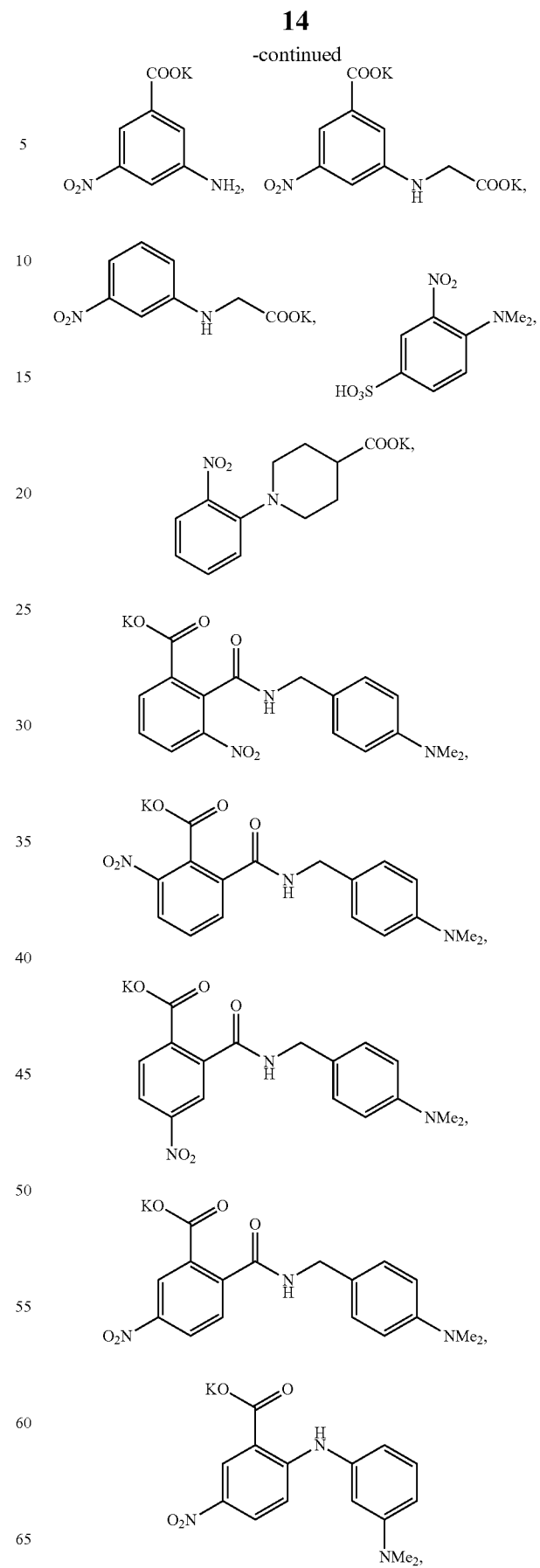

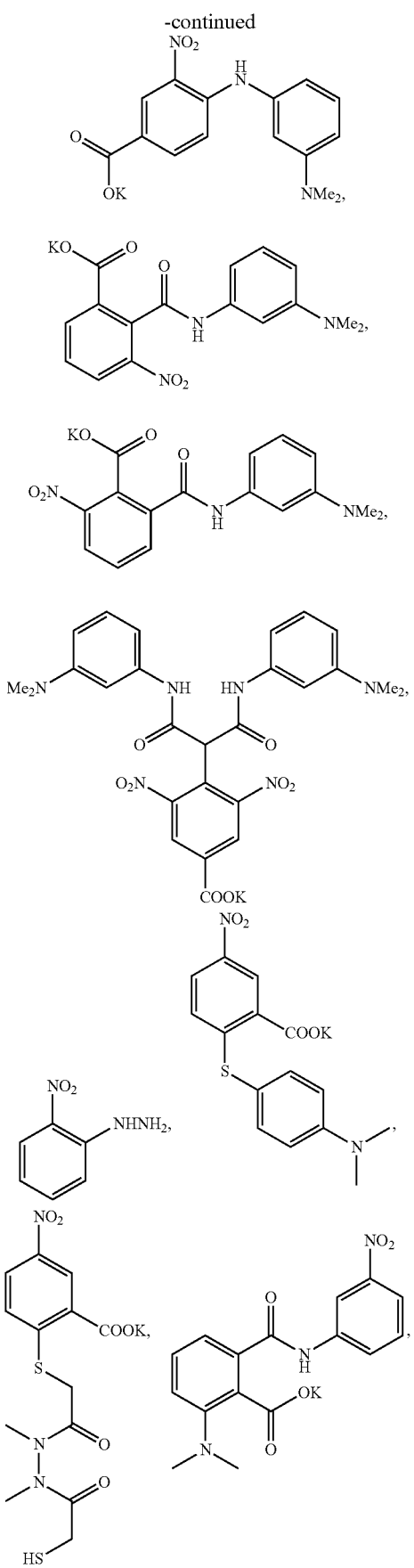

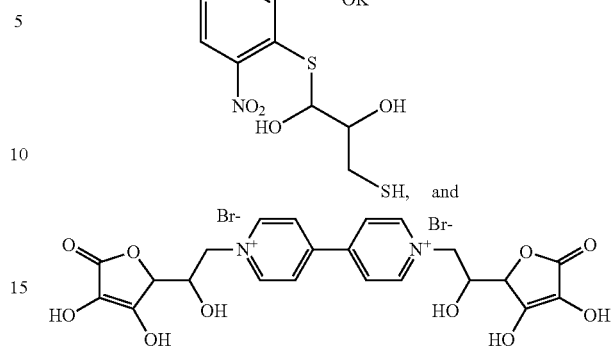

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., K⁺) illustrated).

The methods further include illuminating the reaction mixture with excitation illumination. The photoprotective agent reduces an amount of photo-induced damage to the enzyme resulting from interaction of the enzyme with the fluorescent or fluorogenic substrate under the excitation illumination to an amount that is less than that which would occur in the absence of the photoprotective agent. Such interaction may be a covalent or noncovalent interaction, binding interaction, a transient interaction, a catalytic interaction, and the like. Optionally, the reaction mixture is illuminated for a period of time that is less than a photo-induced damage threshold period, wherein the photo-induced damage threshold period is lengthened in the presence of the photoprotective agent.

Optionally, methods of the invention further include the step of monitoring a reaction between the enzyme and the fluorescent or fluorogenic substrate while illuminating the reaction mixture. In some preferred embodiments, the illuminated reaction is a base extension reaction and the enzyme is optionally a polymerase. Such a reaction typically includes at least one polynucleotide (e.g., template) and a plurality of nucleotide polyphosphates. In other preferred embodiments, the illuminated reaction is a translation reaction during which a polypeptide is synthesized. Such a reaction typically includes a ribosome, and mRNA, and a plurality of amino acid-charged tRNAs. Preferably, one or more component of the reaction mixture are confined upon a substrate, e.g., within a zero mode waveguide.

Also provided by the present invention are compounds having a formula selected from:

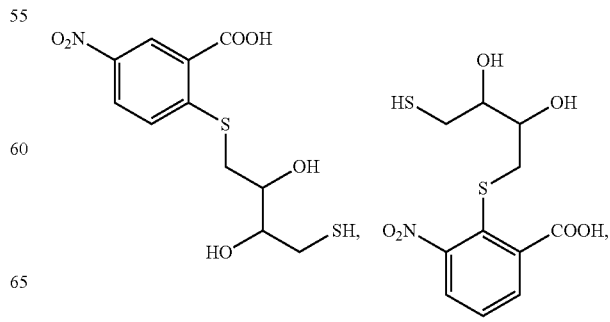

-continued
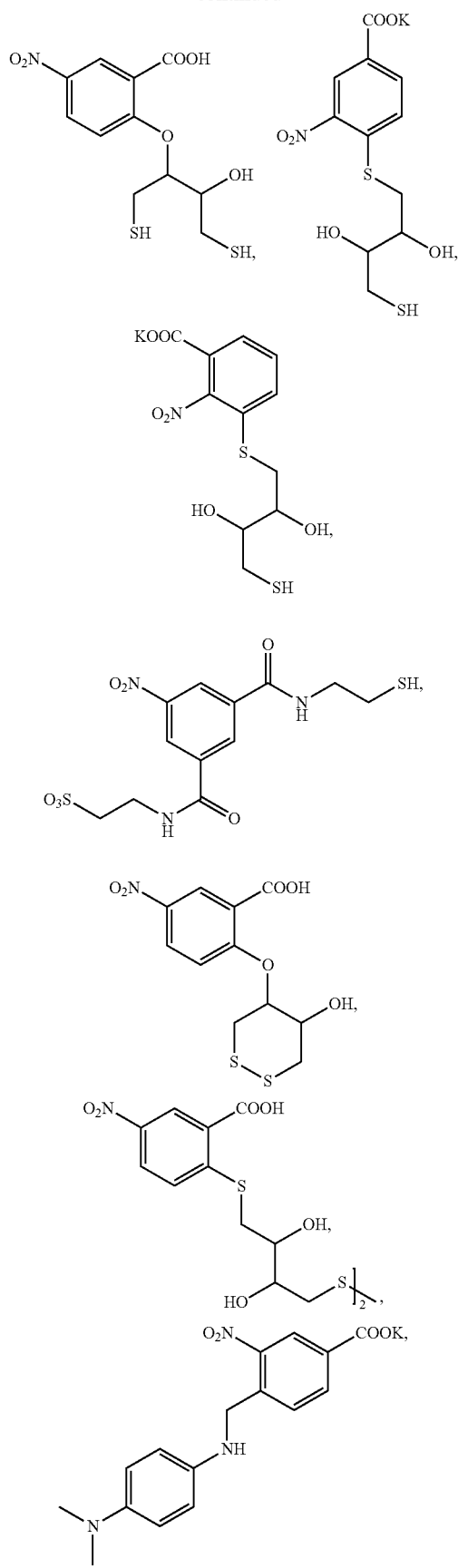
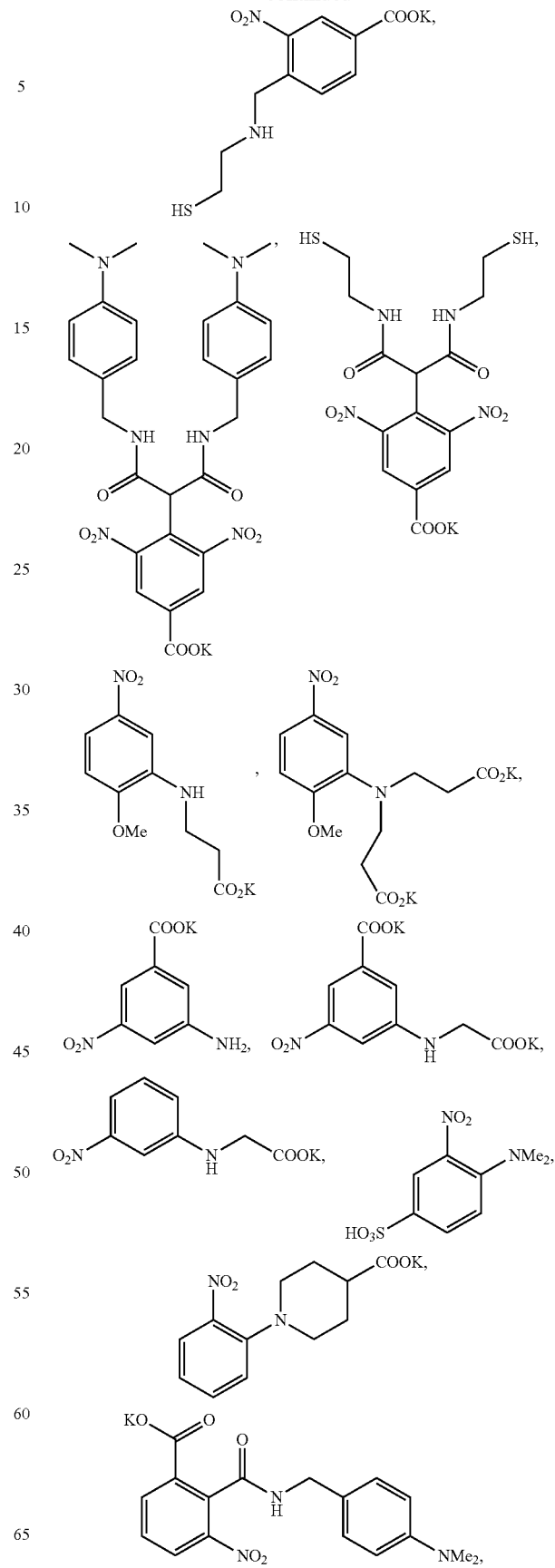

19
-continued

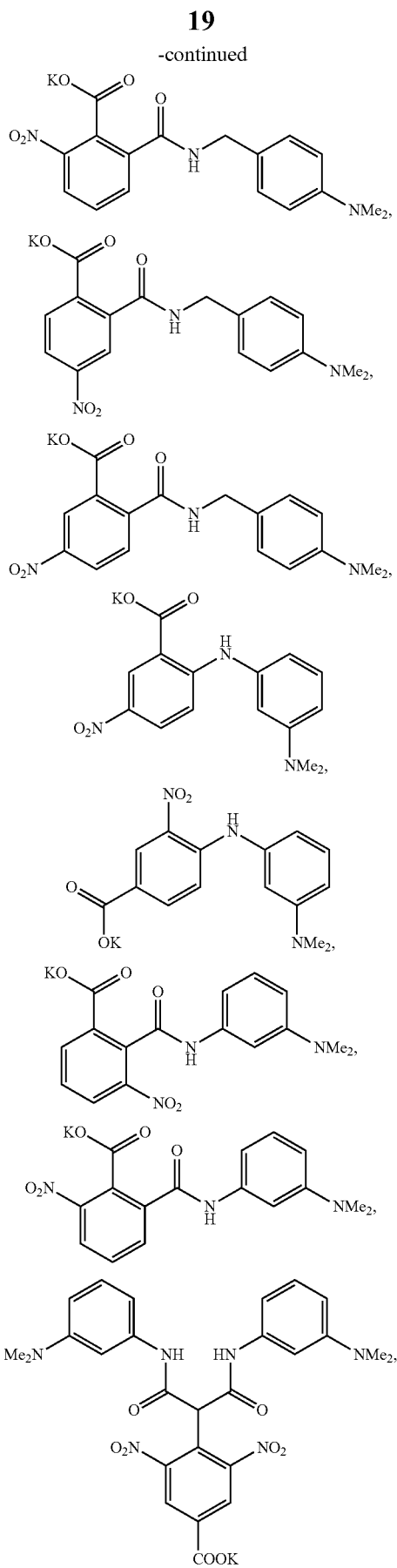

20
-continued

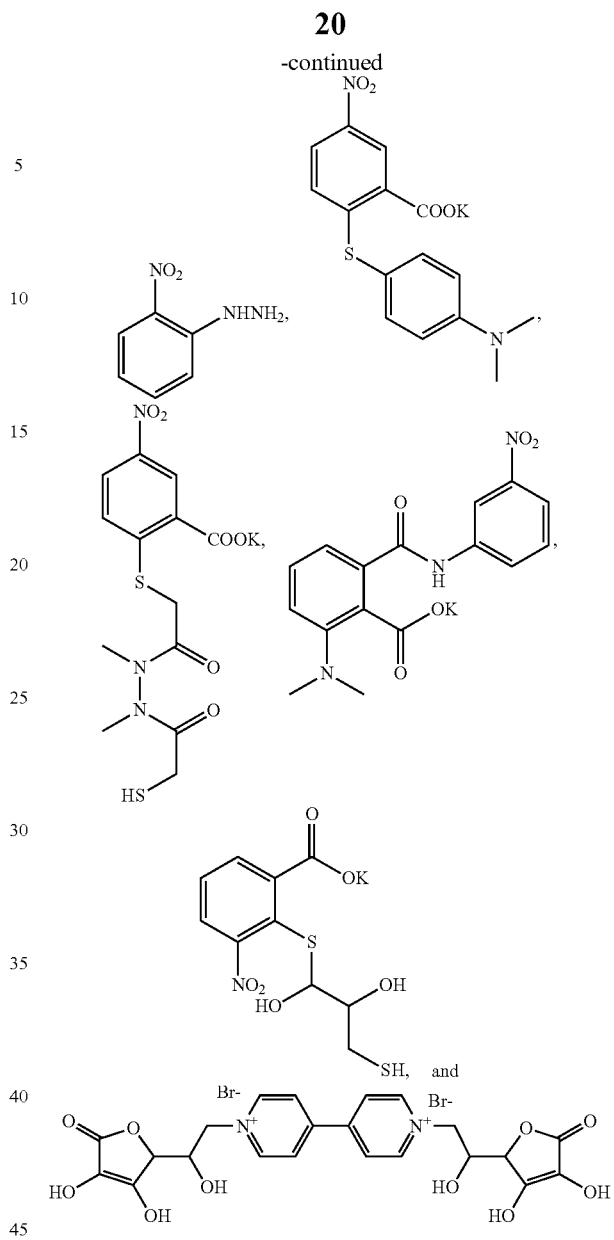

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., $K^+$) illustrated).

In another aspect, the present invention provides devices that include a substrate having an observation region (e.g., an observation region within a zero mode waveguide), a first reactant (e.g., an enzyme, e.g., a polymerase, ligase, nuclease, or a ribosome) immobilized within the observation region, a second reactant disposed within the observation region, where interaction between the first and second reactants under excitation illumination causes photo-induced damage to the first reactant. Where the first reactant is an enzyme, the second reactant is preferably a fluorescent or fluorogenic substrate for the enzyme. In preferred embodiments, at least one or more components of the reaction mixture comprising the first and second reactants is confined upon a substrate, e.g., within a zero mode waveguide. The devices further include a photoprotective agent disposed within the observation region, the photoprotective agent including a reducing unit covalently bound to an oxidizing unit. In certain preferred embodiments, the photoprotective agent further comprises a water solubilizing unit. Certain preferred photoprotective agents are nitrobenzene derivatives. In some embodiments, the photoprotective agent does not comprise a quinone, hydroquinone, or a derivative thereof. Devices of the invention optionally include a photoprotective agent that includes at least one compound of a formula selected from the group consisting of:

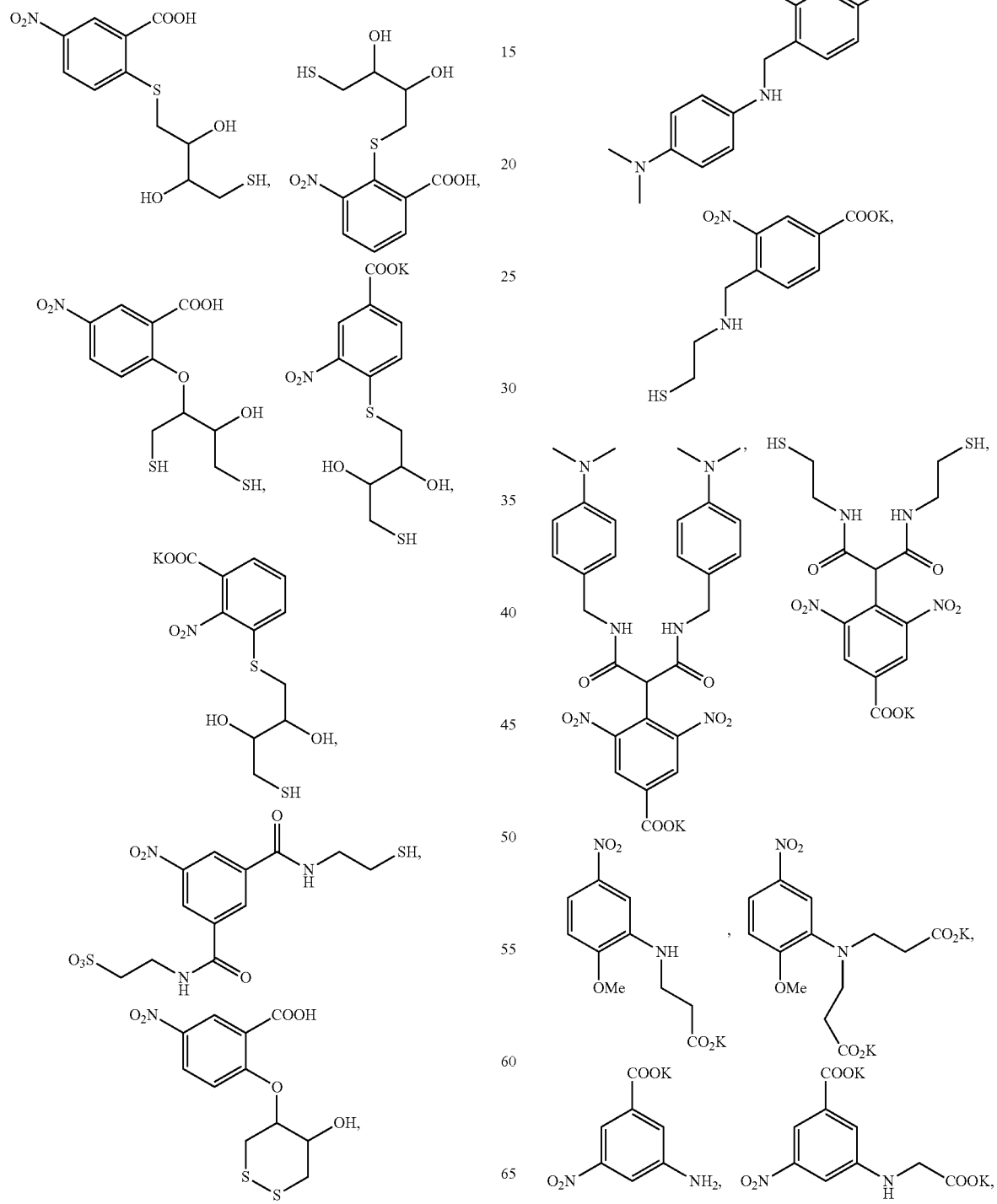

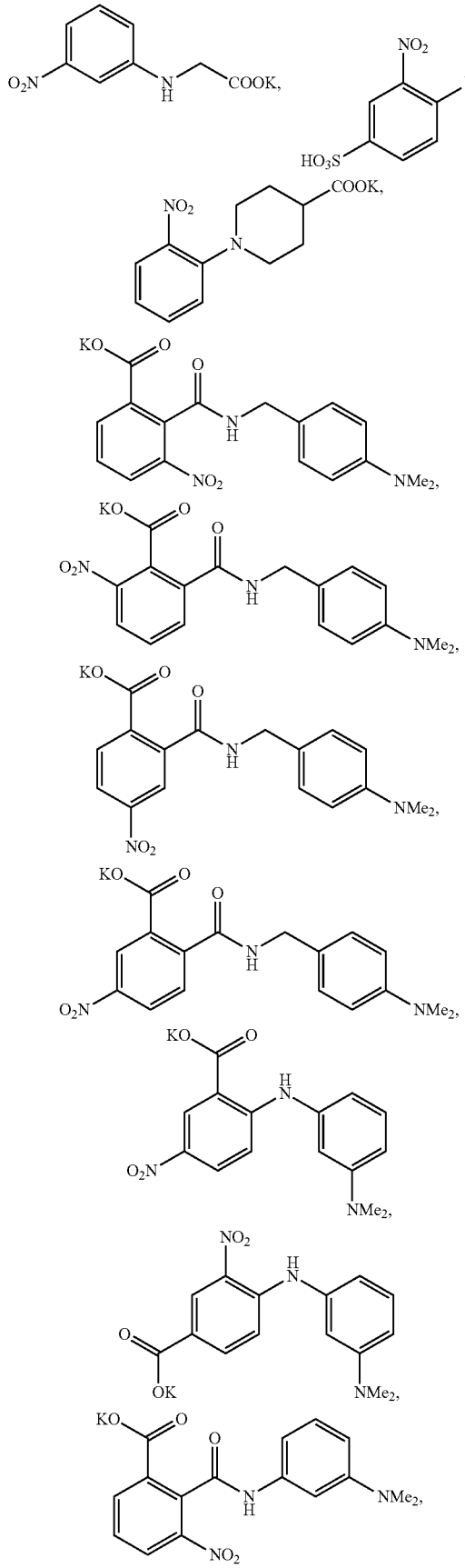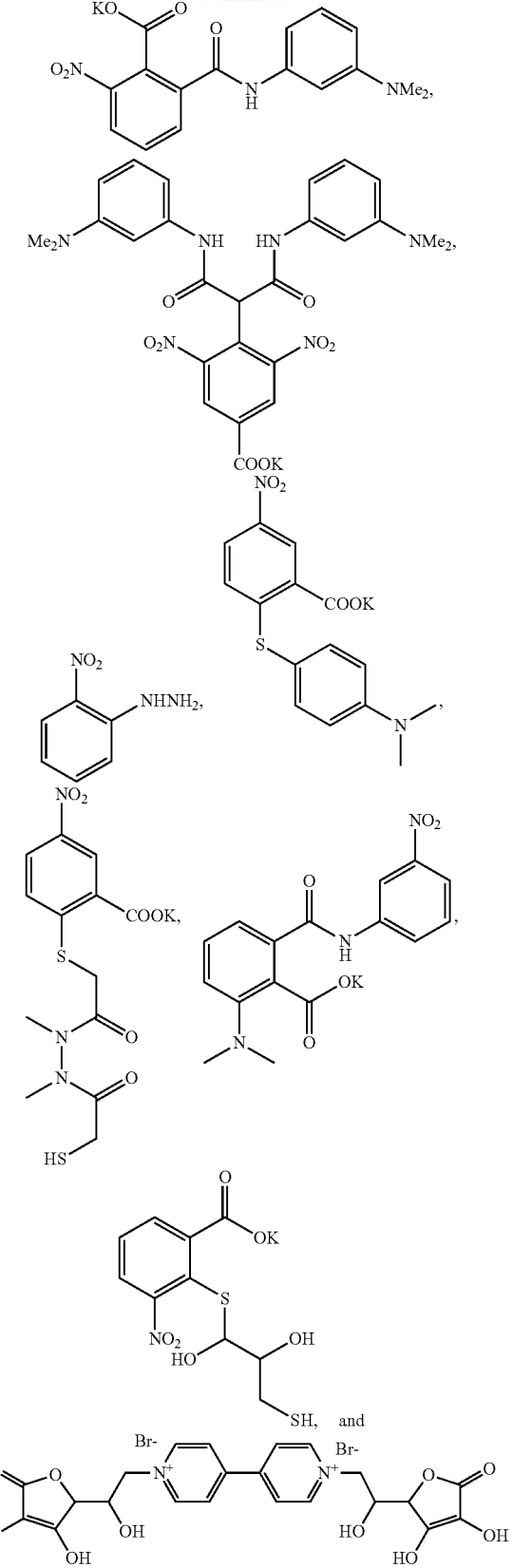
where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., K+) illustrated).

Also provided by the present invention are systems for analyzing an illuminated reaction (e.g., a sequencing reaction, a base extension reaction, etc.) that is susceptible to photo-induced damage when illuminated for a period longer than a photo-induced damage threshold period. Such systems include a mounting stage configured to receive the substrate, an optical train positioned to be in optical communication with at least a portion of the substrate to illuminate the portion of the substrate and detect signals emanating therefrom, a translation system operably coupled to the mounting stage or the optical train for moving one of the optical train and the substrate relative to the other, and a substrate having one or more reagents for the reaction disposed thereon, where at least one of the reagents is a photoprotective agent comprising a reducing unit covalently bound to an oxidizing unit. In certain preferred embodiments, the photoprotective agent further comprises a water solubilizing unit. In certain embodiments, the photoprotective agent comprises a nitrobenzene derivative, and additionally or alternatively, does not comprise a quinone, hydroquinone, or a derivative thereof. Optionally, the substrate includes at least one zero mode waveguide. The one or more photoprotective agents optionally include a compound of the formula selected from:

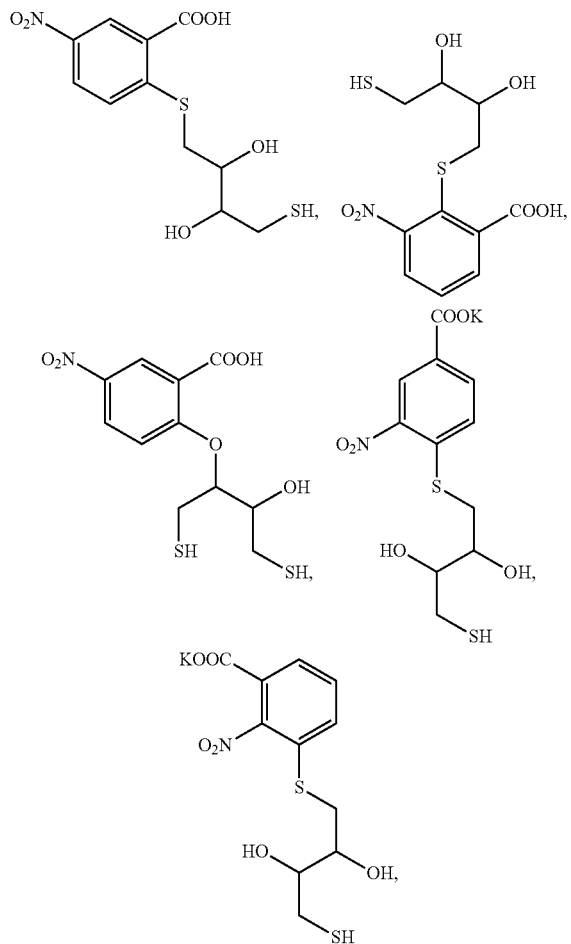

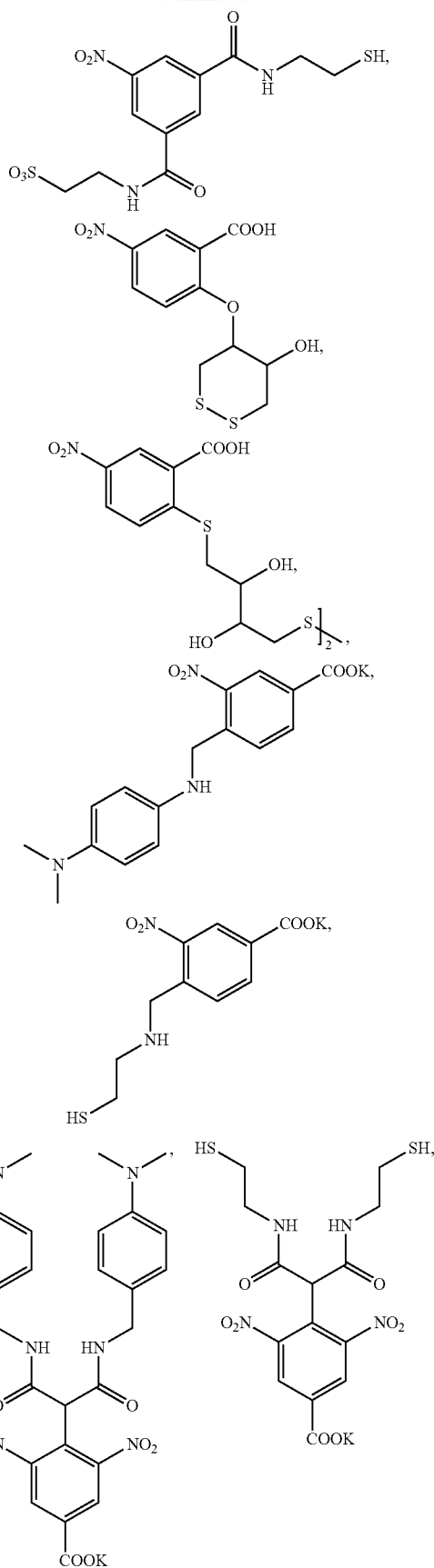

27
-continued
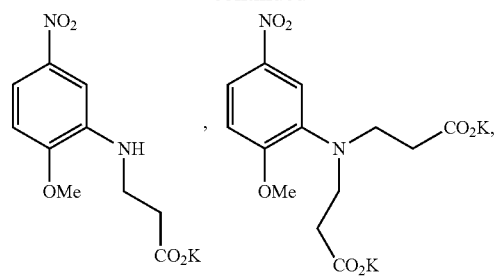
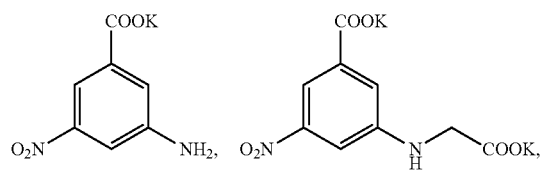
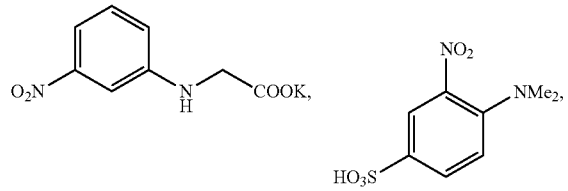
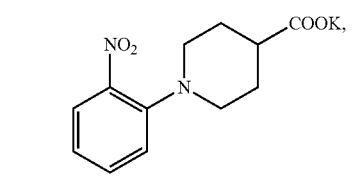
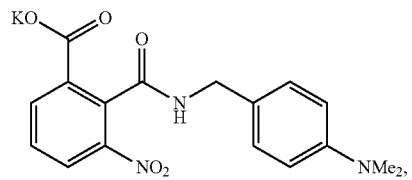
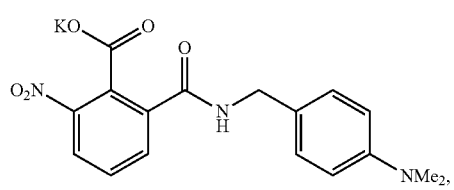
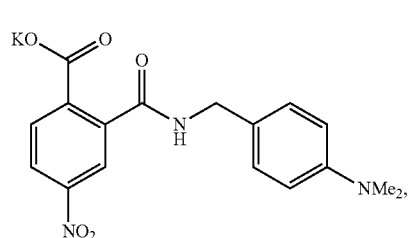
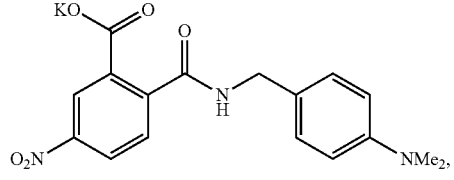
28
-continued
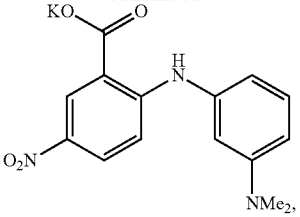
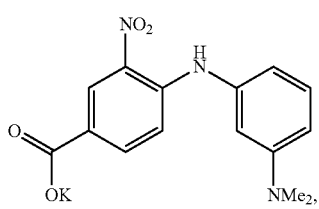
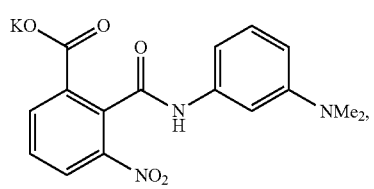
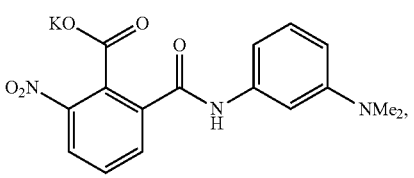
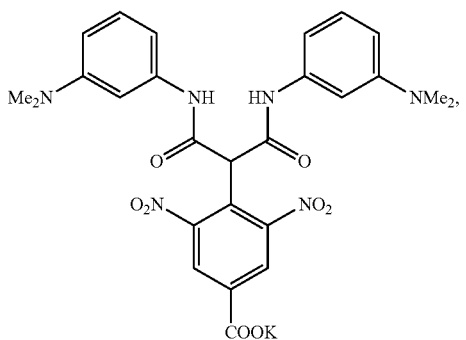
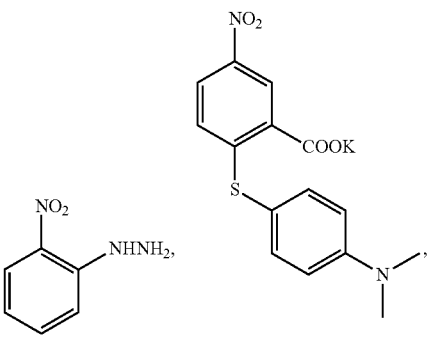

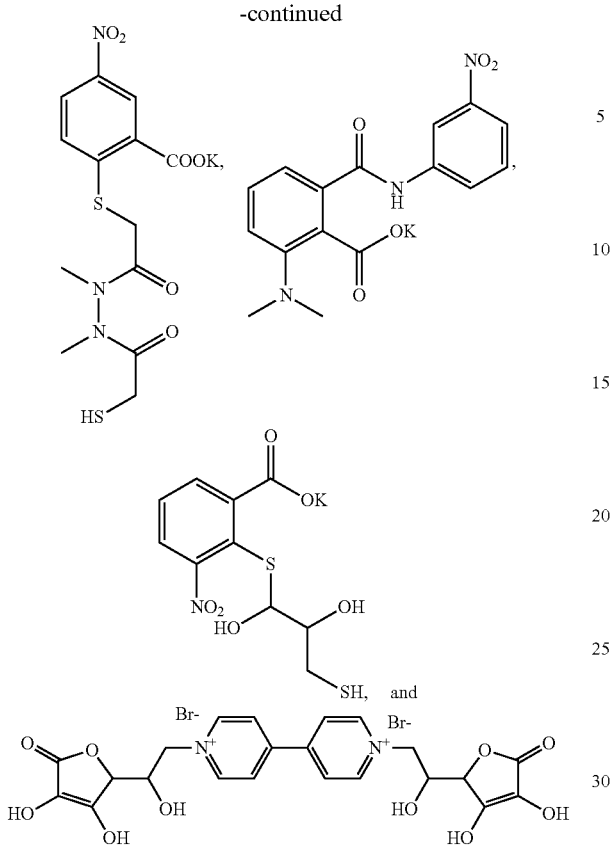

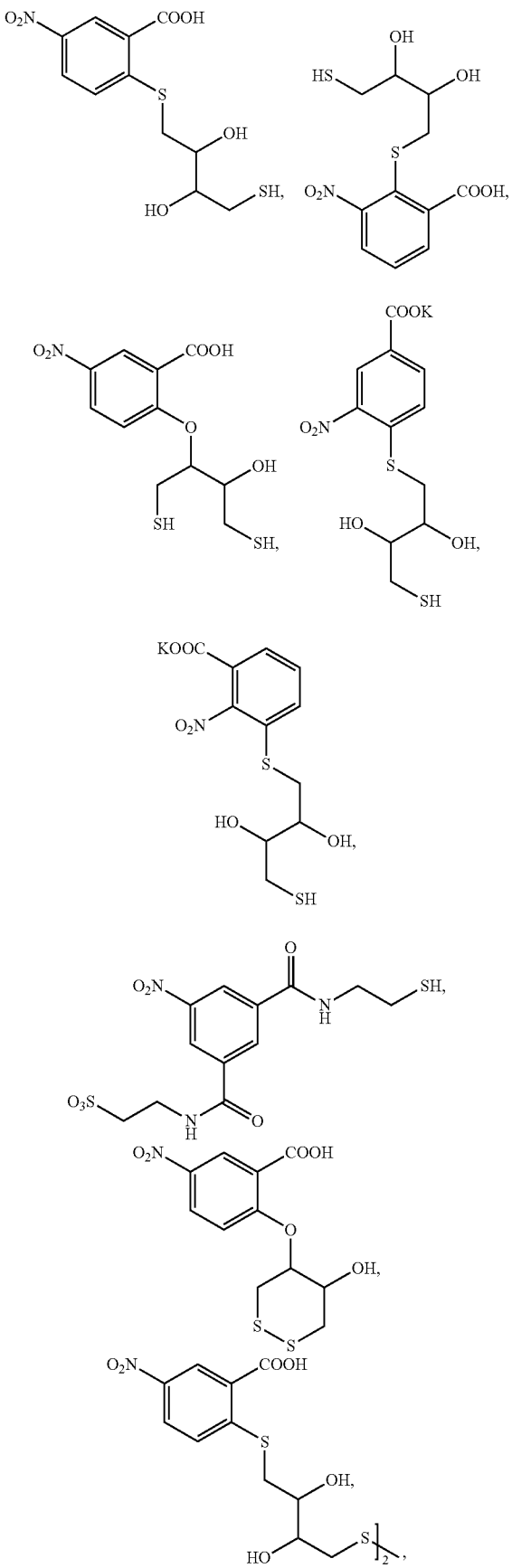

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., $K^+$) illustrated).

In a further aspect, the present invention provides methods for preparing an illuminated reaction mixture (e.g., a sequencing or base-extension reaction mixture) that comprises fluorescent of fluorogenic compounds. The methods include adding a photoprotective agent to the reaction mixture, the photoprotective agent including a reducing unit covalently bound to an oxidizing unit, where the photoprotective agent reduces an amount of photo-induced damage to at least one component of the illuminated reaction mixture that would otherwise occur in the absence of the photoprotective agent. In certain preferred embodiments, the photoprotective agent further comprises a water solubilizing unit. The reducing unit optionally includes one or more of a thiol group, a disulfide group, ascorbic acid, an ascorbic acid derivative, dialkylaniline, a dialkylaniline derivative, anthracene, an anthracene derivative, an aliphatic amine, and/or an aromatic amine. Optionally, the oxidizing unit includes one or more of a nitro group, a quinone, a quinone derivative, methylviologen, a methylviologen derivative, a nitrobenzene derivative, nitrobenzoic acid, or a nitrobenzoic acid derivative. In some preferred embodiments, the photoprotective agent does not comprise a quinone, hydroquinone, or a derivative thereof. The photoprotective agent is preferably a triplet-state quencher, a nitrobenzene derivative (e.g., nitrobenzoic acid or a derivative thereof), or a photoprotective agent that includes a compound of a formula selected from the group consisting of:

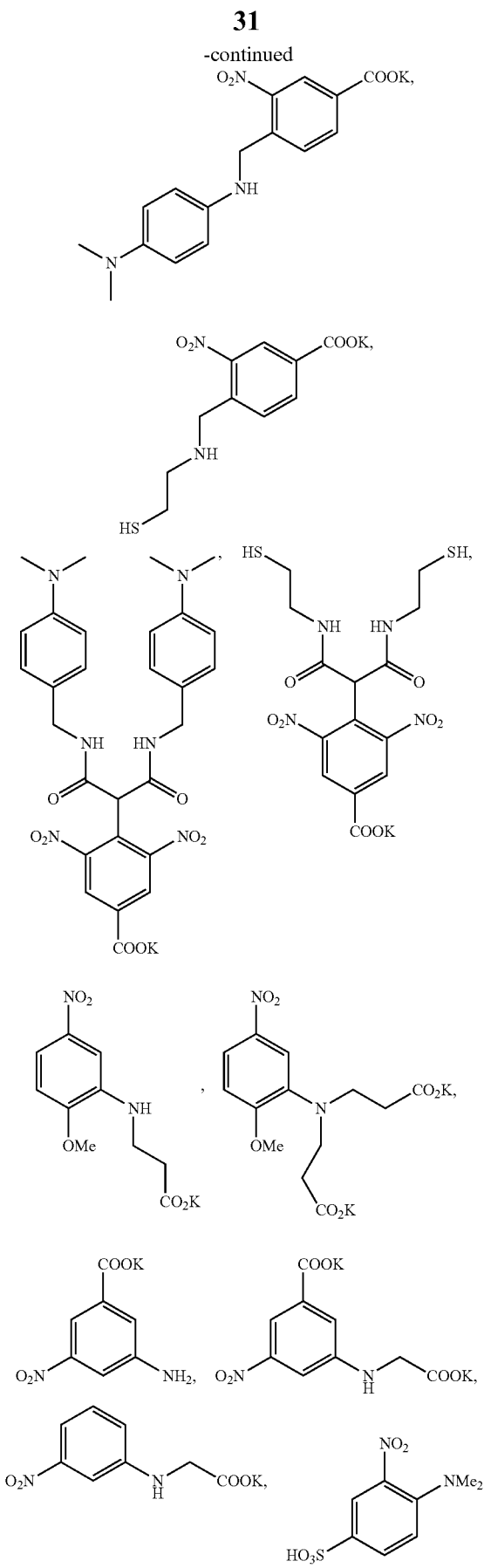
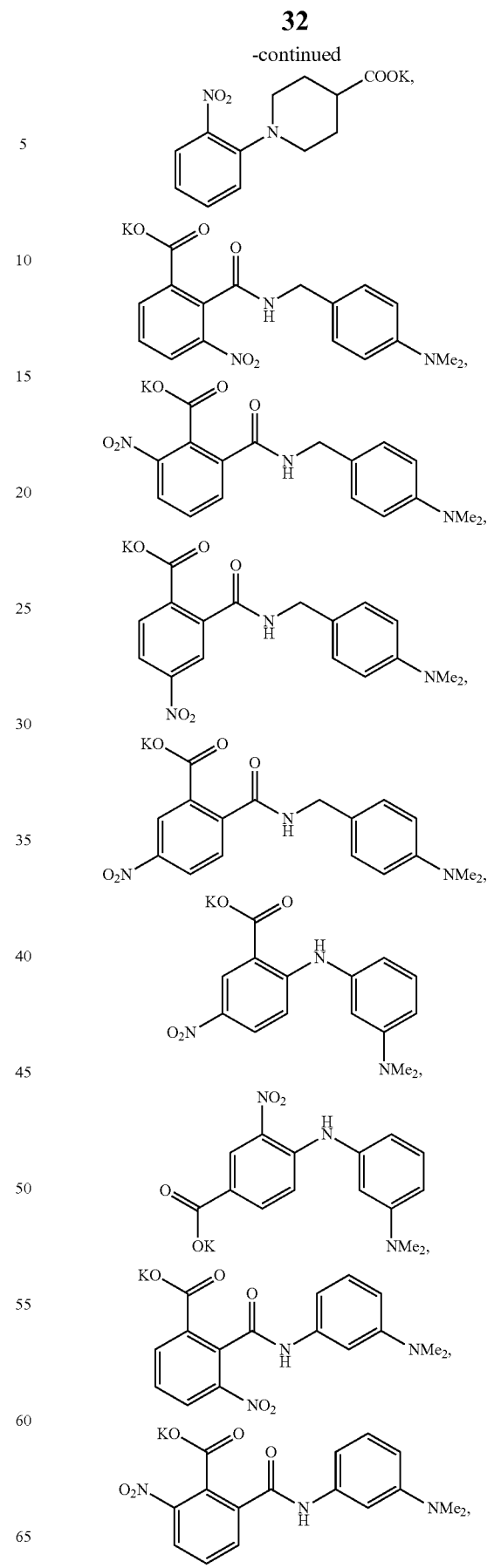

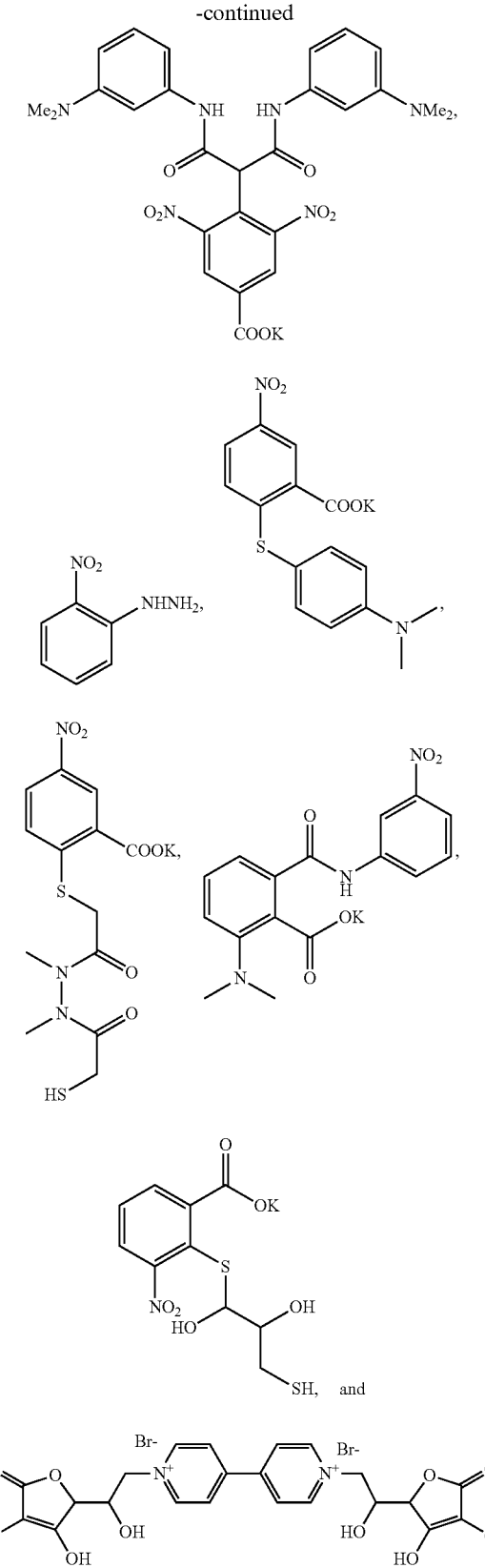

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., K+) illustrated). Optionally, the methods further comprise confining at least one component of the reaction mixture on a substrate, e.g., a substrate that includes one or more zero mode waveguides.

In another aspect, the present invention provides methods for increasing the accuracy of an illuminated sequencing reaction. The methods include providing a reaction mixture that includes a polymerase, a template nucleic acid, one or more fluorescent or fluorogenic nucleotides or nucleotide analogs, and a photoprotective agent that comprises a reducing unit covalently bound to an oxidizing unit, and optionally further comprising a water solubilizing unit. The reaction mixture is exposed to excitation illumination and emission signals are detected from the reaction mixture, e.g, during monitoring of the reaction mixture during the exposure to excitation illumination. The presence of the photoprotective agent enhances the accurate detection of the fluorescent or fluorogenic nucleotides, thereby increasing the accuracy of the resulting sequencing reaction data. For example, the photoprotective agent can decrease an amount of blinking and/or photobleaching of a dye within the fluorescent or fluorogenic nucleotides or nucleotide analogs. Such blinking and/or photobleaching can result from exposure of the dye to the excitation illumination. Addition of the photoprotective agent reduces the amount of blinking and/or photobleaching that would otherwise occur in the absence of the photoprotective agent. In certain preferred embodiments, the illuminated sequencing reaction is a base extension reaction, e.g., a template-directed nascent strand extension reaction. Optionally, at least one component of the reaction mixture is confined within a zero mode waveguide, e.g., the polymerase or the template nucleic acid.

The photoprotective agent is preferably a single molecule ROXS compound as provided elsewhere herein. For example, the photoprotective agent can comprise a nitrobenzene derivative, and/or can optionally not comprise a quinone, hydroquinone, or a derivative thereof. A photoprotective agent can include a compound of a formula selected from the group consisting of:

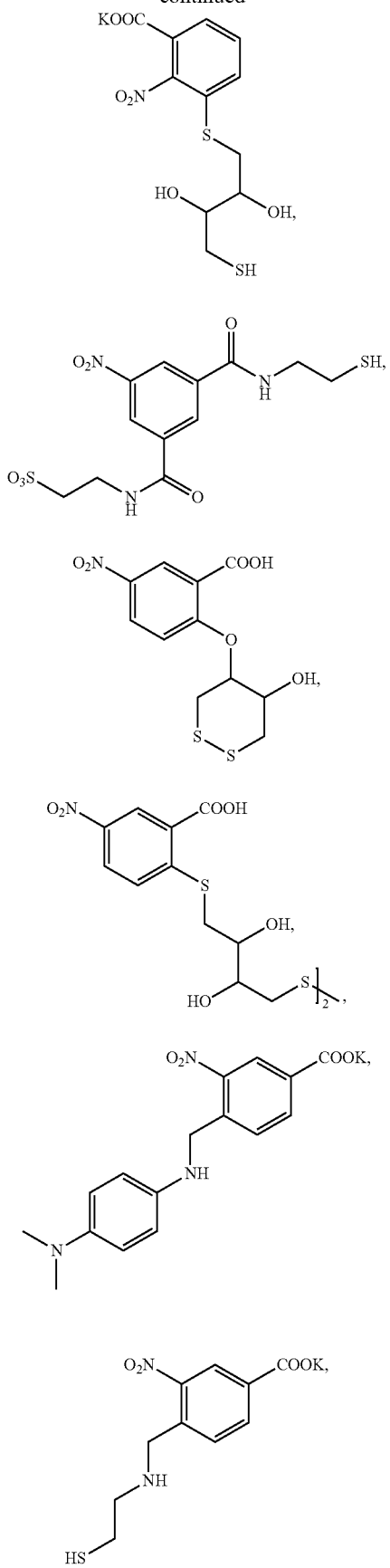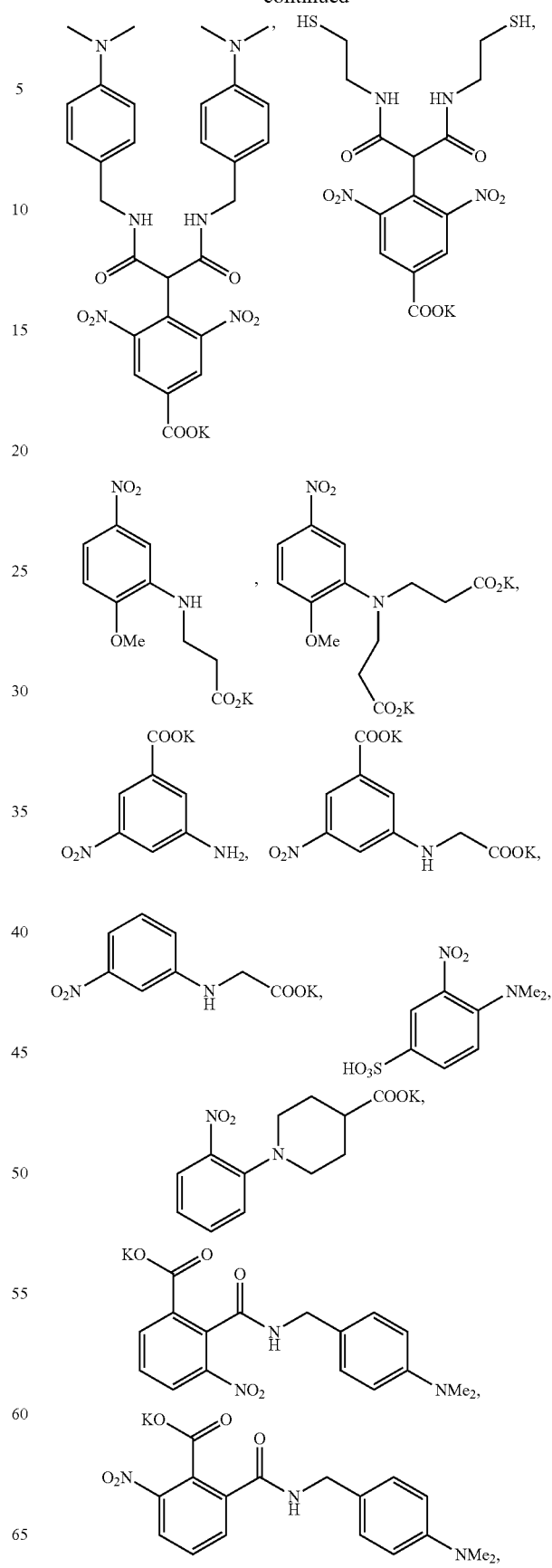

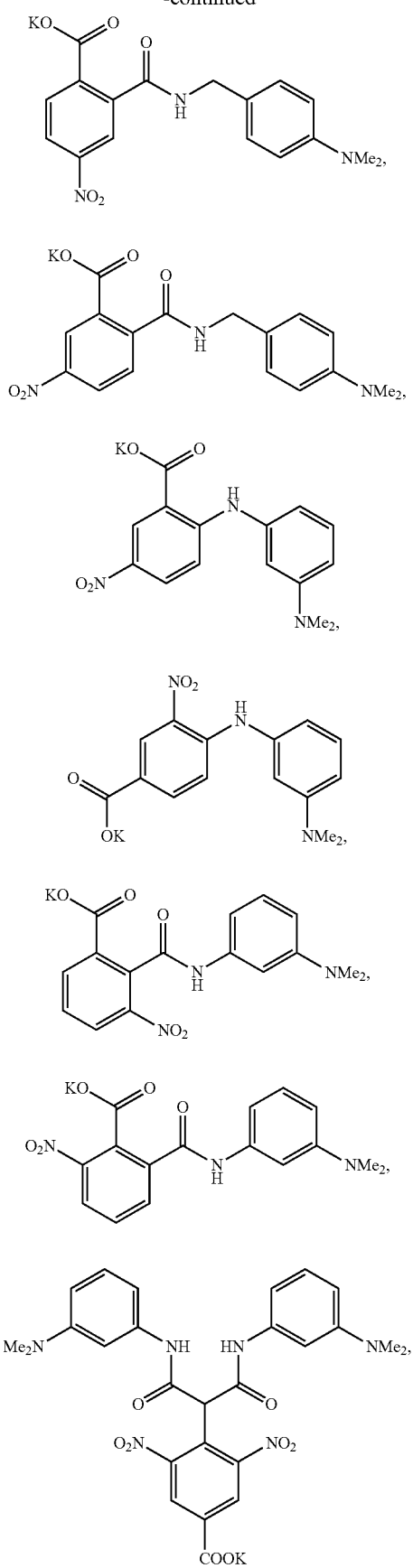

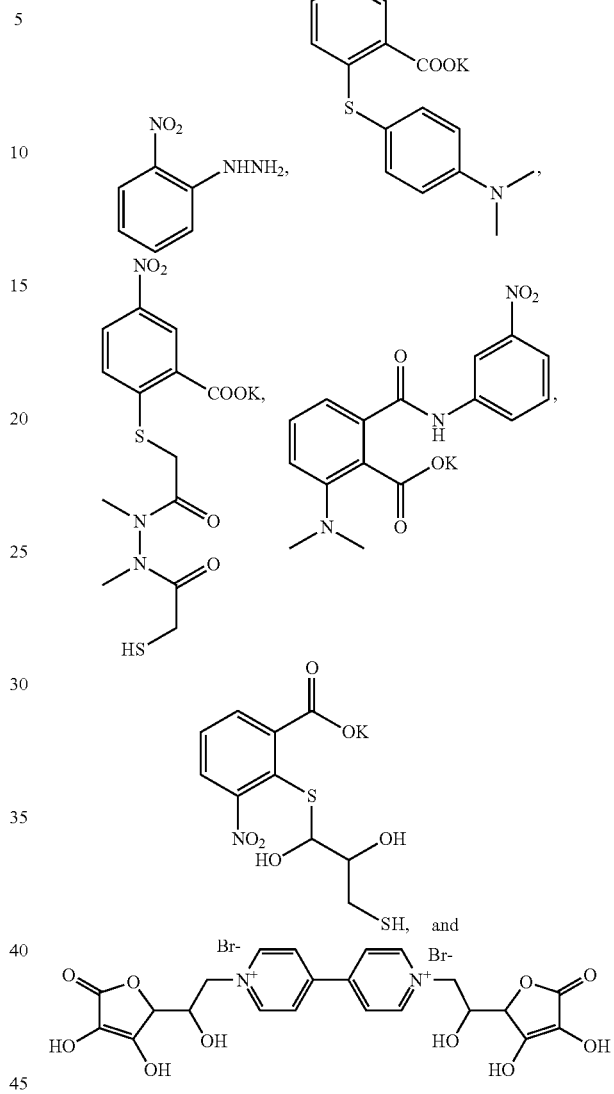

where a carboxyl group may also be a carboxylate salt thereof, e.g., potassium carboxylate; and where a carboxylate salt may be a carboxyl group or a different carboxylate salt (a carboxylate anion bound to a cationic unit different from the one (e.g., $K^+$) illustrated).

The present invention also provides kits that incorporate photo-induced damage mitigating agents, or admixtures thereof, optionally with additional useful reagents. Such kits typically include a photo-induced damage mitigating agent of the invention packaged in a fashion to enable use of the agent with any of a variety of analytical reaction components susceptible to photo-induced damage that participate in a reaction with one or more fluorescent or fluorogenic reaction components. For example, a photo-induced damage mitigating agent of the invention can be packaged with any of a variety of enzymes that participate in a reaction with one or more fluorescent or fluorogenic substrates. Alternatively, a photo-induced damage mitigating agent of the invention can be packaged with any of a variety of antibodies that participate in a reaction with one or more fluorescent or fluorogenic antigens, or vice versa. In still other embodiments, a photo-induced damage mitigating agent of the invention can be packaged with any of a variety of protein receptors that participate in a reaction with one or more fluorescent or fluorogenic ligands. It will be clear that the methods, compositions, and systems described herein are useful with a multitude of other types of analytical reactions, including but not limited to hybridization assays, binding assays (e.g., antibody assays), nucleic acid sequencing assays, protein sequencing assays, polymerization assays, ligation reactions, catalytic reactions, etc. Depending upon the desired application, the kits of the invention optionally include, e.g., buffer solutions and/or salt solutions, divalent metal ions, i.e., $Mg^{++}$, $Mn^{++}$, $Ca^{++}$, $Zn^{++}$ and/or $Fe^{++}$, enzyme cofactors, substrates, standard solutions, e.g., dye standards for detector calibration, etc. Kits can optionally include reagents and instructions for preparing photo-induced damage mitigating agent admixtures. Such kits also typically include instructions for use of the compounds and other reagents in accordance with the desired application methods, e.g., nucleic acid sequencing and the like.

DETAILED DESCRIPTION OF THE INVENTION

Figure 1:
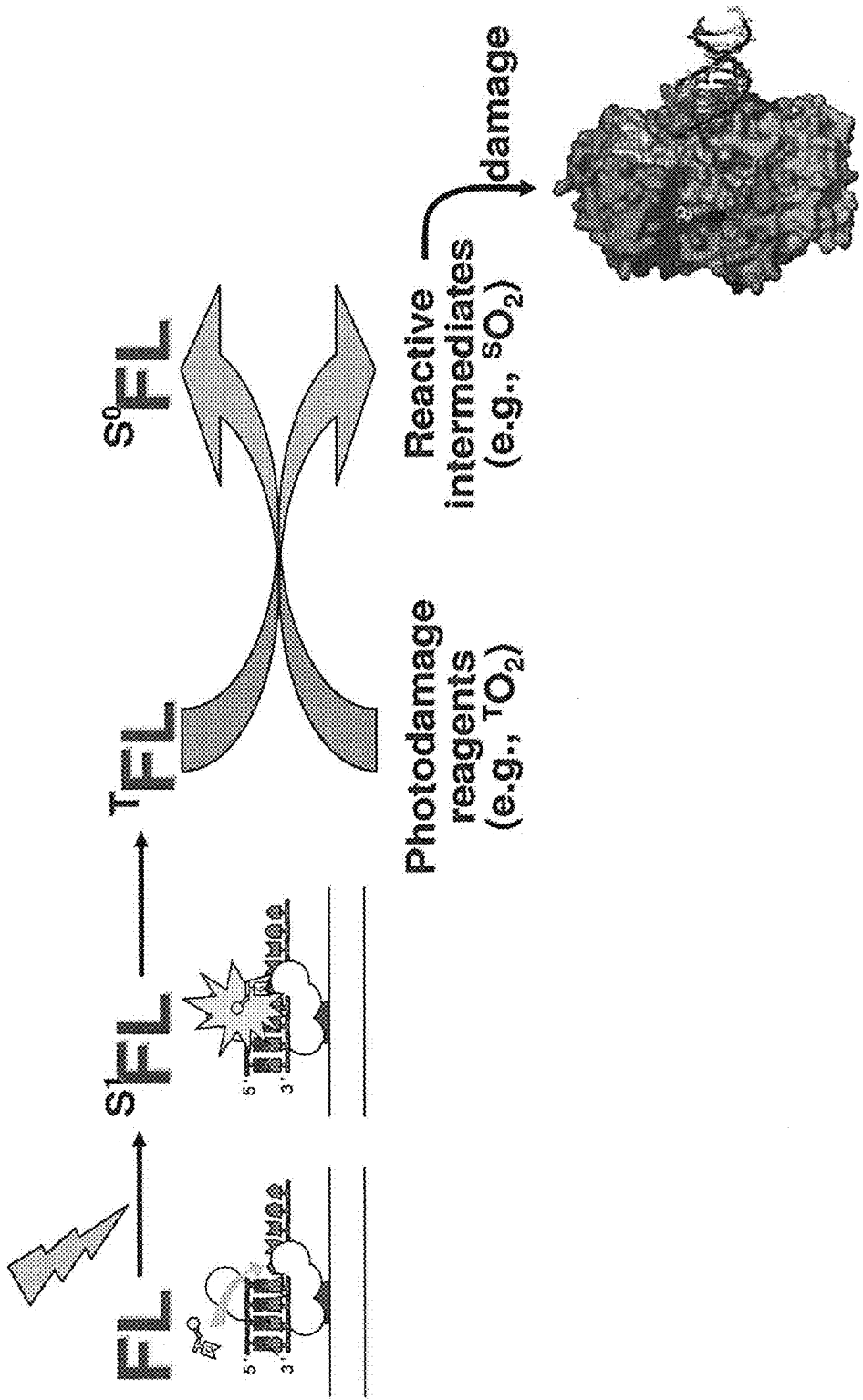
FIG. 1 is a schematic illustration of a proposed mechanism of photo-induced damage to DNA polymerase in template-dependent synthesis using fluorescent nucleotide analogs while under excitation illumination.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth. Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

I. General

The present invention is generally directed to compounds, compositions, methods, devices and systems for preventing, reducing, or limiting the effects of photo-induced damage during illuminated reactions, particularly reactions that employ fluorescent or fluorogenic reactants. Fluorescent or fluorogenic reactants generally include reaction components linked to a fluorescent or fluorogenic molecule or "label." Such reaction components include without limitation enzymes, enzyme substrates, cofactors, reactive proteins, binding partners, and other types of molecules desired to be detected during an analytical reaction. Further, in some embodiments, a fluorescent or fluorogenic molecule can be linked to a reaction site rather than, or in addition to, a reaction component. The present invention provides methods and compositions for protecting reaction components (e.g., enzymes, enzyme substrates, ligands, or fluorescent dyes) from photo-induced damage that can alter the activity of the reaction components. The term "photo-induced damage" refers generally to any direct or indirect impact of illumination on one or more reagents or other components in a reaction resulting in a negative impact upon that reaction. The term "illuminated reactions" as used herein refers to reactions which are exposed to an optical energy source. Typically, such illumination is provided in order to observe the presence (e.g., generation, binding, and/or consumption) of reactants or products that possess a particular optical characteristic indicative of their presence, such as a shift in the absorbance spectrum and/or emission spectrum of the reaction mixture or its components or a change in intensity of fluorescence.

For example, the fluorescence detected in a fluorescence-based optical assay is the result of a three-stage process that occurs in the fluorophores or fluorescent dyes present in a reaction mixture. The first stage is excitation in which a photon with quantized energy from an external light source having a specific wavelength (e.g., from a laser) is supplied and absorbed by a fluorophore creating an excited electronic singlet state ($S_1'$). The second stage is the excited-state lifetime in which the excited fluorophore undergoes several different changes to relax its energy to the lowest singlet state ($S_1$). From the $S_1$ state several possible mechanisms can occur in the third stage, fluorescence, in which a photon of energy ($S_1$-$S_0$) is emitted returning the fluorophore to its ground state. Many thousands of these three-stage processes of excitation and emission typically occur to produce a signal detectable by standard optical sensors.

One of the many pathways that dissipate the energy of the excited electronic singlet state ($S_1$) is the intersystem crossing (ISC), which involves a change in spin multiplicity that transits the system from $S_1$ to the excited triplet state ($T_1$). In many fluorescent dye molecules, the formation of the much longer lifetime triplet-state species competes with fluorescence emission and greatly reduces the brightness of the fluorescence emission. In addition, fluorescent dyes exhibit a high degree of chemical reactivity in this state that often results in photobleaching and the production of damaging free radicals and reactive intermediates, e.g., radical ions, carbenes, carbocations, carbanions, etc. Further, there is also evidence to suggest that even a fluorophore in the $S_1$ state can react with reaction components, e.g., negatively impacting an analytical reaction by mediating the production of non-reactive intermediates.

In general terms, the invention is directed to the performance of illuminated reaction analyses, where such analyses are illuminated for an amount of time that permits the effective performance of the analysis. In some embodiments, one or more photo-induced damage mitigating agents (e.g., reducing agents, oxidizing agents, triplet-state quenchers, free radical quenchers, oxygen scavengers, and/or a combination thereof) may be included in an illuminated reaction. Certain examples of photo-induced damage mitigating agents are provided in U.S. Patent Publication Nos. 2007/0128133, 2007/0161017, and 2010/0136592, all of which are incorporated herein by reference in their entireties for all purposes. In certain embodiments, compounds of the invention function as triplet-state quenchers and/or free radical quenchers, e.g., to prevent, slow, or remove the accumulation of damaging excited triplet-state forms of one or more reaction components. For example, in specific embodiments, using photo-induced damage mitigating agents of the invention slows the accumulation of the excited triplet state of the fluorophore by, e.g, reducing T1 lifetime and restoring the fluorophore to its ground state (S0) (thereby facilitating the availability of the fluorophore to absorb another photon and fluoresce again), greatly improving the photophysical properties of the dye. This reduction in triplet state lifetime also reduces the likelihood that other reaction components will undergo photo-induced damage caused by interaction with a triplet-state dye, thereby essentially protecting the other reaction components and potentially extending the time during which the reaction can generate useful data.

Photoprotective compounds can be added to the reaction mixture, e.g., to form a triplet state quenching (TSQ) system, e.g., with multiple TSQ reagents added to address the triplet states for additional dyes or fluorophores used in the reaction at issue. A reducing and oxidizing system (ROXS) can be effective in minimizing photobleaching and blinking of fluorescent dyes. (*Agnew. Chem. Int. Ed*, 2008, 47, 5465-5469, incorporated herein by reference in its entirety for all purposes.) Such photobleaching and blinking can adversely affect the detectability of an emission from a day, so the presence of an ROXS can facilitate detection at least by reducing these photochemical phenomena. Typically, an ROXS is a multicomponent system, e.g., comprising a pair of TSQ reagents that includes a reducing agent and an oxidizing agent, which can work in concert to speed the relaxation of a dye from its triplet state to its ground state. For example, one reagent reduces the dye triplet state into a radical anion which can then be oxidized by the second reagent back to ground state. Alternatively, the second reagent oxidizes the dye triplet state into a radical cation which can then be reduced by the first reagent into its ground state. An example of such a system is a mixture of methylviologen and ascorbic acid. Another ROXS that can be used is one including nitrobenzoic acid or salts thereof and mercaptoethylamine, e.g., 2-mercaptoetylamineHCL and sodium 2-, 3- and/or 4-nitrobenzoate. Other systems include mixtures of nitrobenzoic acid or salts thereof (e.g., potassium 2-nitrobenzoic acid) and other reducing agents, such as DTT (dithiothreitol) or DMAPA (dimethylaminopropylamine). Adding these reagents to an illuminated reaction can be used to mitigate photo-induced damage to other reactants, e.g., an enzyme, and to improve other reaction metrics, as well. For example, a reduction in photobleaching and/or blinking can improve the detectability of fluorescent or fluorogenic reaction components, which can increase the accuracy with which their presence is monitored. However, a drawback to this type of system, e.g., when used in single molecule systems is that relatively high concentrations of each TSQ reagent are needed because it requires two different bimolecular reactions, one with each TSQ reagent, to complete the triplet state quenching. As such, the rate of completion of the two reactions is diffusion-limited and dependent upon multiple independent molecular collision events. Further, certain analytical reactions are adversely affected by the high concentrations of agents required in a multicomponent ROXS. For example, in a single molecule enzyme reaction, the high concentrations of the ROXS reagents can lead to reduced enzyme (e.g., polymerase, ribosome, nuclease, etc.) activity, e.g., resulting in suboptimal product generation, e.g., reduced read length in a single molecule sequencing reaction.

In certain preferred embodiments, the invention provides methods and compositions for nucleic acid analysis in which a photo-induced damage mitigating agent (also referred to as a photoprotective agent) that is a single compound comprising both a reducing unit (e.g., a functional group comprising a reducing agent, center or moiety) and an oxidizing unit (e.g., a functional group comprising an oxidizing agent, center or moiety) is added to the reaction mixture. This is a preferred method of mitigating photo-induced damage, especially in single molecule reactions, as compared to a method wherein two different compounds (one being a reducing agent and the other an oxidizing agent) must both be added to the reaction mixture. When added separately, reducing and oxidizing compounds are often added in high concentrations, e.g., 10 mM each in order to ensure that their protective effects extend to all reactant molecules in the reaction. It is believed that mitigation of photo-induced damage by separately added reducing and oxidizing compounds is diffusion-limited and requires multiple molecular collision events. As such, relatively high concentrations are required as two different compounds must both interact with the same reactant to produce the two bimolecular reactions needed to complete a reducing and oxidizing system (ROXS) quenching of the triplet state. However, in some small volume reactions, providing such an excess of photo-induced damage mitigating agents can potentially interfere with the ability of a reaction to proceed. Having an intramolecular interaction with both a reducing unit and an oxidizing unit present on the same molecule is highly desirable so that the coupled functions of the two reactions can occur in a single collision, e.g., to further reduce $T_1$ lifetime. Therefore, a lower concentration of photoprotective agent can be used per reaction mixture, which can mitigate negative impacts of the photoprotective agent on the reaction, e.g., due to incompatibilities between the photoprotective agents and the reaction, while still providing the photoprotective properties desired in the reaction, e.g. mitigation of photo-induced damage and/or reduction of blinking or photobleaching.

In certain embodiments, a photoprotective agent, e.g., one comprising both a reducing unit and an oxidizing unit covalently bound in a single compound, can be linked to another reaction component or to a reaction site to bring the photo-induced damage mitigating agent into close spatial proximity to the reactants susceptible to direct or indirect (e.g., by interaction with an excited dye molecule) damage by the illumination. For example, the photo-induced damage mitigating agent may be linked to one or more of a reactant (e.g., a substrate for an enzyme (e.g., a nucleic acid, polypeptide, sugar, or monomers thereof), a fluorescent or fluorogenic label (e.g., a fluorescent dye or quantum dot), an enzyme or other reactive protein or cofactor thereof (e.g., a polymerase, ligase, receptor, antibody, or nuclease)), a reaction site at which the reaction will take place (e.g., within a well, chip, fiber, bead, optical confinement (e.g., zero mode waveguide (ZMW)), etc.), or a combination thereof (See, e.g., U.S. Patent Publication No. 20090325260, incorporated herein by reference in its entirety for all purposes.) In certain embodiments, the invention provides methods and compositions for nucleic acid analysis in which a nucleoside polyphosphate, e.g., having three to eight phosphate groups, is linked to a fluorescent dye, and wherein the compound further includes, integrated into its structure (e.g., linked directly to the dye or nucleoside polyphosphate, or to a structure connecting them, such as a scaffold or linker), a photo-induced damage mitigating agent (e.g., one comprising both a reducing and an oxidizing activity), which generally refers to any agent that can prevent and/or mitigate damages caused directly or indirectly by illumination, for example, by triplet/radical quenching. In other embodiments, a photo-induced damage mitigating agent (e.g., one comprising both reducing and an oxidizing activity) is linked to an enzyme or reactive protein that interacts with a substrate or ligand comprising a fluorescent dye. For example, where such enzyme or reactive protein is immobilized at a reaction site by a linker construct, the photo-induced damage mitigating agent can be integrated into the structure of the linker construct. Such conjugates and compositions of the present invention are particularly useful in small reaction volumes, because incorporating the photo-induced damage mitigating agent into one of the reactants or linking it to a reaction site helps to maintain the protective effects of the agent without needing to provide the agent in an excess quantity, in part by removing diffusion-limited processes present when the photo-induced damage mitigating agents are free in solution and completion of the reaction is therefore dependent upon multiple independent molecular collision events. Further, because the close proximity of the photo-induced damage mitigating agents to the reactants can hasten the removal or reversal of a radical formed during illumination, it can also lessen the likelihood that the radical will react with other reaction components.

The invention is generally applicable to any of a variety of optical assays that involve substantial illumination and/or photoactivated conversion or excitation of chemical groups, e.g., fluorophores, and is particularly useful for assays that are impaired by the generation and/or accumulation of triplet-state forms or free radicals. For example, the compositions and methods provided herein may be used with fluorescence microscopy, optical traps and tweezers, spectrophotometry, fluorescence correlation spectroscopy, confocal microscopy, near-field optical methods, fluorescence resonance energy transfer (FRET), structured illumination microscopy, total internal reflection fluorescence microscopy (TIRF), etc., all of which are well known techniques that are routinely used by those of skill in the art.

Further, the methods provided herein are particularly useful in analyses that utilize very limited concentrations of reactants that might be subject to photo-induced damage, such as single molecule detection/monitoring assays. As will be appreciated, in such reagent-limited analyses, any degradation of a critical reagent will dramatically impact the analysis by further limiting the reagent, which not only can adversely effect the detectable signal, but may also directly impact the reaction being monitored, e.g., by changing its rate, duration, or product(s). For example, photo-induced damage can include a photo-induced change in a given reagent that reduces the reactivity of that reagent in the reaction, e.g., photobleaching of a fluorescent molecule under excitation illumination, which diminishes or removes its ability to act as a signaling molecule. Also included in the term photo-induced damage are other changes that reduce a reactant's usefulness in a reaction, e.g., by making the reagent less specific in its activity in the reaction. Likewise, photo-induced damage includes undesired changes in a reagent that are caused by interaction of that reagent with a product of another photo-induced reaction, e.g., the generation of singlet oxygen during a fluorescence excitation event, which singlet oxygen may damage organic or other reagents, e.g., proteins. Such interaction may be a covalent or noncovalent interaction, a binding interaction, a transient interaction, a catalytic interaction, and the like. For example, damage to an enzyme that catalyzed a reaction being monitored may cause a reduction in the rate of the reaction, in some cases stopping it altogether, or may reduce the duration or fidelity of the reaction. As such, it is to be understood that reference to photo-induced damage includes both direct damage to a reactant caused by optical energy (e.g., excitation radiation), as well as indirect damage caused by interaction with another reactant that has undergone direct or indirect photo-induced damage. It is to be understood that excitation radiation as used herein may comprise optical energy in the UV, visible, and/or IR range.

One particularly apt example of analyses that benefit from the invention are single-molecule biological analyses, including, inter alia, single molecule nucleic acid sequencing analyses, single molecule enzyme analyses, hybridization or binding assays (e.g., antibody assays), nucleic acid hybridization assays, nucleic acid sequencing assays, protein sequencing assays, polymerization assays, ligation reactions, catalytic reactions, and the like, where the reagents of primary import are subjected to prolonged illumination with relatively concentrated light sources (e.g., lasers and other concentrated light sources, such as mercury, xenon, halogen, or other lamps) in an environment where excitation/photo-conversion is occurring with its associated generation of products. In certain embodiments, the methods, compositions, and systems are used in nucleic acid sequencing processes that rely on detection of fluorescent or fluorogenic reagents. Examples of such nucleic acid sequencing technologies include, for example, SMRT™ nucleic acid sequencing (described in, e.g., U.S. Pat. Nos. 6,399,335, 6,056,661, 7,052,847, 7,033,764, 7,056,676, 7,361,466, 7,416,844; U.S. Patent Publication No. 20100311061; and in Eid, et al. (2009) Science 323:133-138, the full disclosures of which are incorporated herein by reference in their entireties for all purposes), non-real time, or "one base at a time" sequencing methods available from, e.g., Illumina, Inc. (San Diego, Calif.), Helicos BioSciences (Cambridge, Mass.), Clonal Single Molecule Array™, and SOLiD™ sequencing. Methods for single molecule protein sequencing are provided, e.g., in U.S. Patent Publication No. 20100317116, which is incorporated herein by reference in its entirety for all purposes. Such prolonged illumination can result in photo-induced damage to reaction component and can diminish their effectiveness in the desired reaction. Adding compounds of the invention, e.g., a compound containing both a reducing and an oxidizing center, to the reaction mixtures can reduce the effects of the photo-induced damage, e.g., by increasing the photo-induced damage threshold period or in practical terms, increasing the read length of a nucleic acid sequencing reaction.

II. Illuminated Analyses

Certain aspects of the invention are generally directed to mitigating photo-induced damage during the performance of illuminated analyses. The terms "illuminated analysis" and "illuminated reaction" are used interchangeably and generally refer to an analytical reaction that is occurring while being illuminated (e.g., with excitation radiation), so as to evaluate the production, consumption and/or conversion of luminescent (e.g., fluorescent or fluorogenic) reactants and/or products. As used herein, the terms "reactant" and "reagent" are used interchangeably. In certain preferred embodiments, the illuminated reaction is a sequencing reaction and the photo-induced damage results, directly or indirectly, from an excitation radiation source used to detect fluorescently labeled nucleoside polyphosphates as they are used to extend to a nascent nucleic acid strand. In certain preferred embodiments, the illuminated reaction is a polypeptide sequencing reaction and the photo-induced damage results, directly or indirectly, from an excitation radiation source used to detect fluorescently labeled amino acids during nascent polypeptide strand synthesis. In certain preferred embodiments, the illuminated reaction is a binding assay to detect association between an antibody and an antigen and the photo-induced damage results, directly or indirectly, from an excitation radiation source used to detect a binding event, e.g., by observation of one or more labels linked to the antibody and/or antigen. In certain preferred embodiments, the illuminated reaction is a hybridization assay to detect association between two nucleic acids that share complete or partial complementarity, and the photo-induced damage results, directly or indirectly, from an excitation radiation source used to detect a hybridization event, e.g., by observation of one or more labels linked to one or both of the nucleic acids.

The amount of time an illuminated analysis may be carried out before photo-induced damage so substantially impacts the reactants to render the analysis non-useful (e.g., when the reaction prematurely terminates) is referred to as the "photo-induced damage threshold period." A photo-induced damage threshold period is assay-dependent, and is affected by various factors, including but not limited to characteristics of reactants (e.g., enzymes, substrates, binding partners, etc.) in the assay (e.g., susceptibility to photo-induced damage and the effect of such damage on enzyme activity/processivity), characteristics of the radiation source (e.g., wavelength, intensity), characteristics of the signal-generating molecule (e.g., type of emission, susceptibility to photo-induced damage, propensity to enter triplet state, and the effect of such damage on the brightness/duration of the signal), and similar characteristics of other components of the assay. It can also depend on various components of the assay system, e.g., signal transmission and detection, data collection and analysis procedures, etc. It is well within the abilities of the ordinary practitioner to determine an acceptable photo-induced damage threshold period for a given assay, e.g., by monitoring the signal decay for the assay in the presence of a photodamaging agent and identifying a period for which the signal is a reliable measure for the assay, and such analyses can optionally include time course reactions, titrations, and the like. In certain preferred embodiments of the invention, the photo-induced damage threshold period is that period of illuminated analysis during which such photo-induced damage occurs so as to reduce the rate, processivity, fidelity, product formation, or error frequency of the subject reaction by no more than 10%, 20%, 30%, 40%, 50%, 60%, 70%, 80%, or 90% over the same reaction in the absence of such illumination. This impact on the subject reaction is typically due to direct or indirect damage to one or more reaction components, and of particular interest are those present in limiting quantities, e.g., at a low concentration. For example, certain single molecule reactions comprise immobilized reactants that are present as a single molecule at a given reaction site. While other reactants in solution can diffuse in and out of the reaction site, such immobilized reactants are not "exchangeable" in the reaction mixture. As such, damage to these immobilized reactants is typically detrimental to the subject reaction at a given reaction site, and can even cause premature termination of the single reaction being monitored at a reaction site. It is an object of the invention to increase the photo-induced damage threshold period, thereby increasing the amount of time reactions can proceed toward completion with minimal damage to the reactants, thereby lengthening the time in which a detectable signal is an accurate measure of reaction progression. In particular, it is an object to reduce damage to reactants at limiting concentrations, e.g., immobilized reactants, and especially those present as single molecules at a reaction site.

In some contexts, a reaction comprising one or more components that have been subject to photo-induced damage may be subject to spurious activity, and thus be more active than desired. In such cases, it will be appreciated that the photo-induced damage threshold period of interest would be characterized by that period of illuminated analysis during which such spurious activity, e.g., as measured by an increase in reaction rate, or an increase in non-specific reaction rate, is no more than 10% over a non-illuminated reaction, no more than 20% over a non-illuminated reaction, no more than 50% over a non-illuminated reaction, and in some cases, no more than 90% over a non-illuminated reaction. In one non-limiting example, where a nucleic acid polymerase, by virtue of a photodamaging event, begins to incorrectly incorporate nucleotides (or analogs or derivatives thereof) during template directed synthesis, such activity would impact the photo-induced damage threshold period as set forth above. In this case, the compounds and methods of the invention would increase the photo-induced damage threshold period, thus increasing the amount of time the reaction could be illuminated before the above-described spurious activity occurred.

With reference to nucleic acid analyses, it has been observed that in template-directed synthesis of nucleic acids using fluorescent nucleotide analogs as a substrate, prolonged illumination can result in a substantial degradation in the ability of the polymerase to synthesize the nascent strand of DNA, as described previously, e.g., in U.S. Published Patent Application No. 20070161017, incorporated by reference herein in its entirety for all purposes. Damage to polymerase enzymes, template sequences, and/or primer sequences can significantly hinder the ability of the polymerase to process longer strands of nucleic acids. For example, reduction in the processivity of a polymerase leads to a reduction in read lengths for sequencing processes that identify sequence constituents based upon their incorporation into the nascent strand. As is appreciated in the art of genetic analysis, the length of contiguous reads of sequence directly impacts the ability to assemble genomic information from segments of genomic DNA. Such a reduction in the activity of an enzyme can have significant effects on many different kinds of reactions in addition to sequencing reactions, such as ligations, cleavages, digestions, phosphorylations, other types of polymerizations, etc.

Without being bound to a particular theory or mechanism of operation, it is believed that at least one cause of photo-induced damage to enzyme activity, particularly in the presence of fluorescent reagents, results from the direct interaction of the enzyme with photodamaged fluorescent reagents. Such interaction may be a covalent or noncovalent interaction, a binding interaction, a transient interaction, a catalytic interaction, and the like. Further, it is believed that this photo-induced damage of the fluorescent reagents (and possibly additional damage to the enzyme) is at least partially mediated by reactive intermediates (e.g., reactive oxygen species) that are generated during the relaxation of triplet-state fluorophores. One or both of the photo-induced damaged fluorescent reagents and/or reactive intermediates may be included in the overall detrimental effects of photo-induced damage. One possible mechanism for this photo-induced damage is shown in FIG. 1. As shown, a fluorophore excited by exposure to electromagnetic radiation at an excitation wavelength can transition into a triplet state. This may occur directly, or as a result of multi-photon processes, where an excited fluorophore transitions to the triplet state upon contact with a photon of a wavelength that is shorter (or bluer) than the nominal excitation wavelength of the fluorophore. Subsequent relaxation of the triplet-state fluorophore can lead to generation of reactive intermediates, which can, in turn, damage one or both of the fluorophore or the enzyme processing the fluorophore, e.g., the polymerase. Accordingly, photo-induced damage mitigating agents (e.g., free radical and/or triplet-state quenching agents) are useful to prevent or slow the formation of reactive intermediates. Such agents can be included within the reaction mixtures or directly incorporated into compounds of the invention, other reaction components, or confined at a reaction site to alleviate, prevent, and/or reverse the effects of reactive intermediates, as well as other species generated during illuminated reaction that can cause photo-induced damage, e.g., in single molecule reactions.

The photo-induced damage sought to be prevented by the methods and compositions of the invention is not merely photo-induced damage to fluorescent reagents, e.g., photo-bleaching, but is also directed to prevention or reduction of the downstream effects of photoactivation of such fluorescent reagents, e.g., during interaction with or proximity to other reagents, and in particular those that are of limited quantity in a reaction mixture, and as such, their limited presence is more greatly impacted by even slight losses due to photo-induced damage. For example, and without being bound to a theory of operation, photo-induced damage to reactive proteins, enzymes, or other reactants may include damage to the reactants or irreversible interactions between such reactants and the photo-induced damaged reagents. Such interactions may be covalent or noncovalent interactions, binding interactions, transient interactions, catalytic interactions, and the like. As suggested by the foregoing, photo-induced damage generally refers to an alteration in a given reagent, reactant, or the like, that causes such reagent to have altered functionality in a desired reaction, e.g., reduced activity, reduced specificity, or a reduced ability to be acted upon, converted, or modified, by another molecule, that results from, either directly or indirectly, a photo-induced reaction, e.g., a photo-induced reaction creates a reactant that interacts with and causes damage to one or more other reactants. Typically, such a photoreaction directly impacts either the reactant of interest, e.g., direct photo-induced damage, or impacts a reactant within one, two or three reactive steps of such reactant of interest. Further, such photoreaction can directly impact the reaction of interest, e.g., causing a change in rate, duration, processivity, product formation, or fidelity of the reaction.

In another aspect of the invention, the photo-induced damage mitigating agents described herein are particularly suitable for mitigating photo-induced damage to reactants in small reaction volume concentrations, wherein such reactants may be present in solution, but at very limited concentrations, As generally referred to herein, such limited quantity reagents or reactants may be present in solution, but at very limited concentrations, e.g., less than 200 nM, in some cases less than 10 nM and in still other cases, less than 10 pM. In preferred aspects, however, such limited quantity reagents or reactants refer to reactants that are immobilized, or otherwise confined within a given area (a reaction site, e.g., within a confinement, e.g., a well, channel, or zero mode waveguide), so as to provide limited quantity of reagents in that given area, and in certain cases, provide small numbers of molecules of such reagents within that given area, e.g., from 1 to 1000 individual molecules, preferably between 1 and 10 molecules. As will be appreciated, photo-induced damage of immobilized reactants in a given area will have a substantial impact on the reactivity of that area, as other, non-damaged reactants are not free to diffuse into and mask the effects of such damage.

While methods and compositions for limiting photo-induced damage to fluorophores have been previously provided, the negative impacts of downstream photodamage, e.g., to enzymes in the presence of or resulting from photodestruction of fluorescent reagents is a particular object of the present invention. The detrimental effect of the of a photodamage event, whether from actual damage to a given reagent from the fluorophore or from interaction with a downstream damaged reagent is generally referred to herein as photodamage or photo-induced damage. Any reagent that can prevent the photodamage is referred to herein as a "photoprotective reagent" or a "photo-induced damage mitigating agent."

The present invention therefore provides, e.g., for use on such substrates, photoprotective agents that reduce the level of photo-induced damage to these limited quantities of reagents. In preferred embodiments, such photoprotective agents comprise both a reducing unit (e.g., a functional group comprising a reducing agent, center or moiety) and an oxidizing unit (e.g., a functional group comprising an oxidizing agent, center or moiety). Example photoprotective agents of the invention include, but are not limited to nitrobenzene derivatives or nitrobenzoic acid derivatives, e.g., nitrobenzoic acid derivatives further comprising a thiol, a disulfide group, an aliphatic amine, or an aromatic amine.

III. Prevention or Mitigation of Photo-Induced Damage

In a first aspect, the invention is directed to methods and compositions that reduce, prevent, or reverse the amount of photo-induced damage to one or more reactants during an illuminated reaction, e.g., during excitation, the excited-state lifetime, or emission. In particular, compositions are provided that yield a reduction in the level of photo-induced damage (or an increase in the photo-induced damage threshold period) as compared to such reactions in the absence of such compositions. As used herein, the components of such compositions that provide such effects are generally referred to as photo-induced damage mitigating agents or photoprotective agents. In particular, photo-induced damage mitigating agents are provided in the context of the illuminated reaction to reduce the level of photo-induced damage (and/or increase the photo-induced damage threshold period), that would otherwise have occurred but for the presence of the photo-induced damage mitigating agent.

Again, the definition of an agent as a photo-induced damage mitigating agent is generally reflective of the impact that such agent has on the actual photo-induced damage event or the downstream impacts of that damage. As such, the detrimental impact of the photo-induced damage event, whether resulting from actual damage to a given reagent or from interaction with a damaged reagent, is generally referred to herein as photo-induced damage. Such interaction may be a covalent or noncovalent interaction, a binding interaction, a transient interaction, a catalytic interaction, and the like. Therefore, a photo-induced damage mitigating agent may prevent photo-induced damage of one or more reagents, or it may mitigate the impact that a photo-induced damaged reagent may have on a particular, limited reagent in the reaction of interest. By way of example, an agent that blocks a detrimental interaction between a photo-induced damaged fluorescent compound and a critical enzyme component (e.g., by quenching the triplet state of the fluorescent compound) would still be referred to as a photo-induced damage mitigating agent, regardless of the fact that it did not prevent but rather reverted the initial photo-induced damage (triplet state formation) to the fluorescent reagent.

Measurements of reduction of photo-induced damage as a result of inclusion or treatment with one or more photo-induced damage mitigating agents may be characterized as providing a reduction in the level of photo-induced damage over an untreated reaction. Further, characterization of a reduction in photo-induced damage generally utilizes a measurement of reaction rates, durations, processivities, product formation, or fidelities, e.g., of enzyme activity, and/or a comparison of the photo-induced damage threshold period, between a treated reaction mixture and an untreated reaction mixture. These analyses generally involve well established laboratory methods, such as time course reactions, titrations, and the like.

In the case of the present invention, the inclusion of photo-induced damage mitigating agent(s) of the invention generally results in a reduction of photo-induced damage of one or more reactants in a given reaction, as measured in terms of "prevented loss of reactivity" in the system. Using methods known in the art, the amount of prevented loss of activity can be at least 10%, preferably greater than 20%, 30%, or 40%, and more preferably at least 50% reduction in loss of reactivity, and in many cases greater than a 90% and up to and greater than 99% reduction in loss of reactivity. By way of illustration, and purely for the purpose of example, when referring to reduction in photo-induced damage as a measure of enzyme activity in the presence and absence of the photo-induced damage mitigating agent, if a reaction included a reaction mixture having 100 units of enzyme activity that would, in the absence of a photo-induced damage mitigating agent and following illuminated analysis, yield a reaction mixture having only 50 units of activity, then a 10% reduction in photo-induced damage would yield a final reaction mixture of 55 units (e.g., 10% of the 50 units otherwise lost, would no longer be lost). Similarly, "prevented loss of reactivity" can be computed in terms of reaction rates, product formation, processivity, fidelity, and other metrics of a given analytical reaction.

IV. Photo-Induced Damage Mitigating Agents

Accordingly, in at least one aspect, the present invention is directed to an illuminated reaction volume that includes one or more photo-induced damage mitigating agents that function to block or otherwise minimize the pathways that lead to such photo-induced damage, e.g., due to the creation of triplet-state fluorophores and resulting reactive oxygen species that can form during an illuminated reaction. Such agents that prevent photo-induced damage include reducing and/or oxidizing agents or anti-fade agents that reduce the lifetime and/or formation of the triplet-state fluorophores (also referred to as triplet-state quenchers), in some cases by interacting/reacting with a triplet-state fluorophore, thereby preventing its interaction with (and resulting photo-induced damage to) other reaction components. Such agents also include oxygen and/or radical scavenging/quenching agents that remove oxygen, reactive oxygen species, and other radicals from the reaction mixture, thus preventing downstream damage to enzymes and/or other reaction components within the system. Such agents also include mixtures of agents having one or more reducing, oxidizing, anti-fade, triplet-state quenching, oxygen radical scavenging/quenching, or radical scavenging/quenching activities. For example, in some preferred embodiments enzymatic systems for oxygen removal (oxygen scavenging) are used (e.g., protocatechuic acid/protocatechuate dioxygenase), optionally in combination with other types of photo-induced damage mitigating agents. Certain examples of photo-induced damage mitigating agents are provided, e.g., in U.S. Published Patent Application Nos. 20070161017 and 20100136592, the disclosures of which are incorporated herein by reference in their entireties for all purposes.

As described above, the drawbacks to using multicomponent ROXS include the diffusion-limited, collision-based functionalities of these systems, which necessitate the use of relatively high concentrations of each photoprotective reagent (e.g., TSQ) to be effective, as well as the adverse effects of such high concentrations on certain analytical reactions. The present invention provides a solution to the requirement for high concentrations of ROXS components, and the detrimental effects that accompany them by combining the reducing agent and the oxidizing agent into a single photoprotective compound, termed a "single molecule ROXS." This single molecule ROXS allows the reducing and oxidizing functions to occur in a single bimolecular interaction between the photoprotective agent and the triplet state molecule so that the oxidizing and reducing reactions occur nearly simultaneously. As a result, the single molecule ROXS can be used at a much lower concentration as compared to the multiple photoprotective reagents in the conventional ROXS described above. For example, the concentration of the single molecule ROXS can be similar to that of a single member of a conventional ROXS pair. In certain embodiments, the single molecule ROXS is provided at a concentration of, e.g., 12 mM or lower, 10 mM or lower, 8 mM or lower, 6 mM or lower, 4 mM or lower, 2 mM or lower, or 1 mM or lower.

Figure 2:
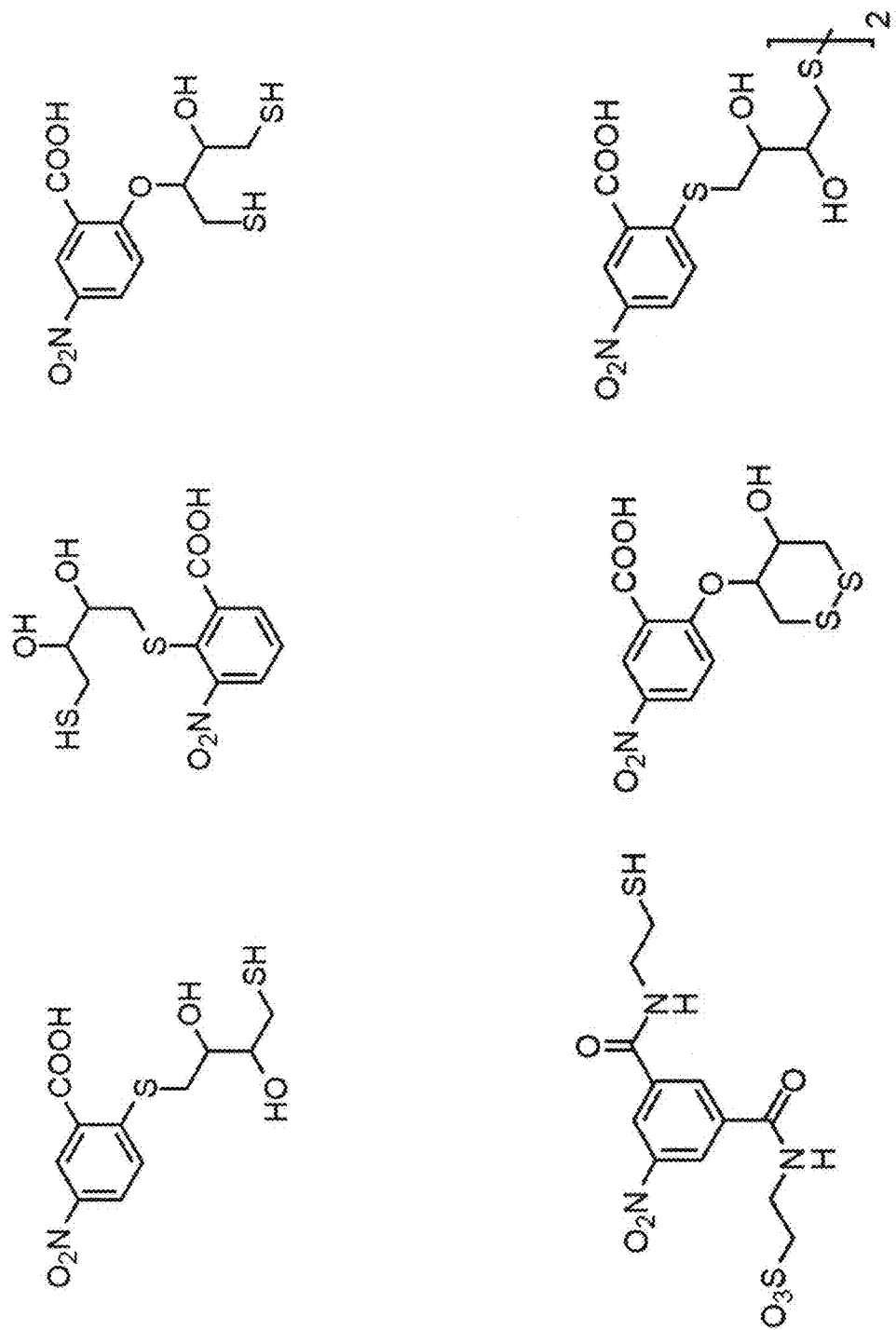
FIG. 2 provides certain exemplary embodiments of the photoprotective agents provided herein.
Figure 2:
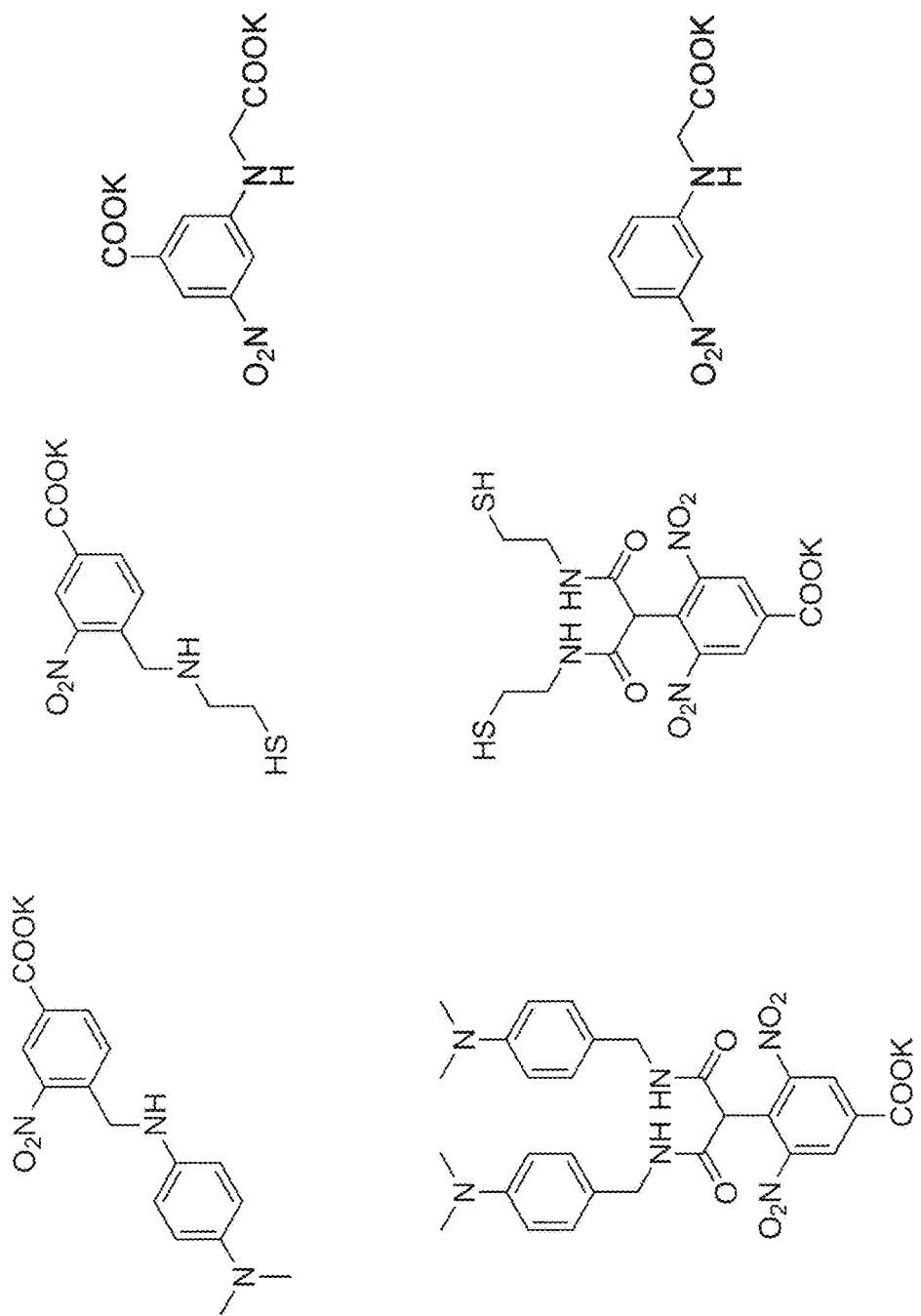
Figure 2:
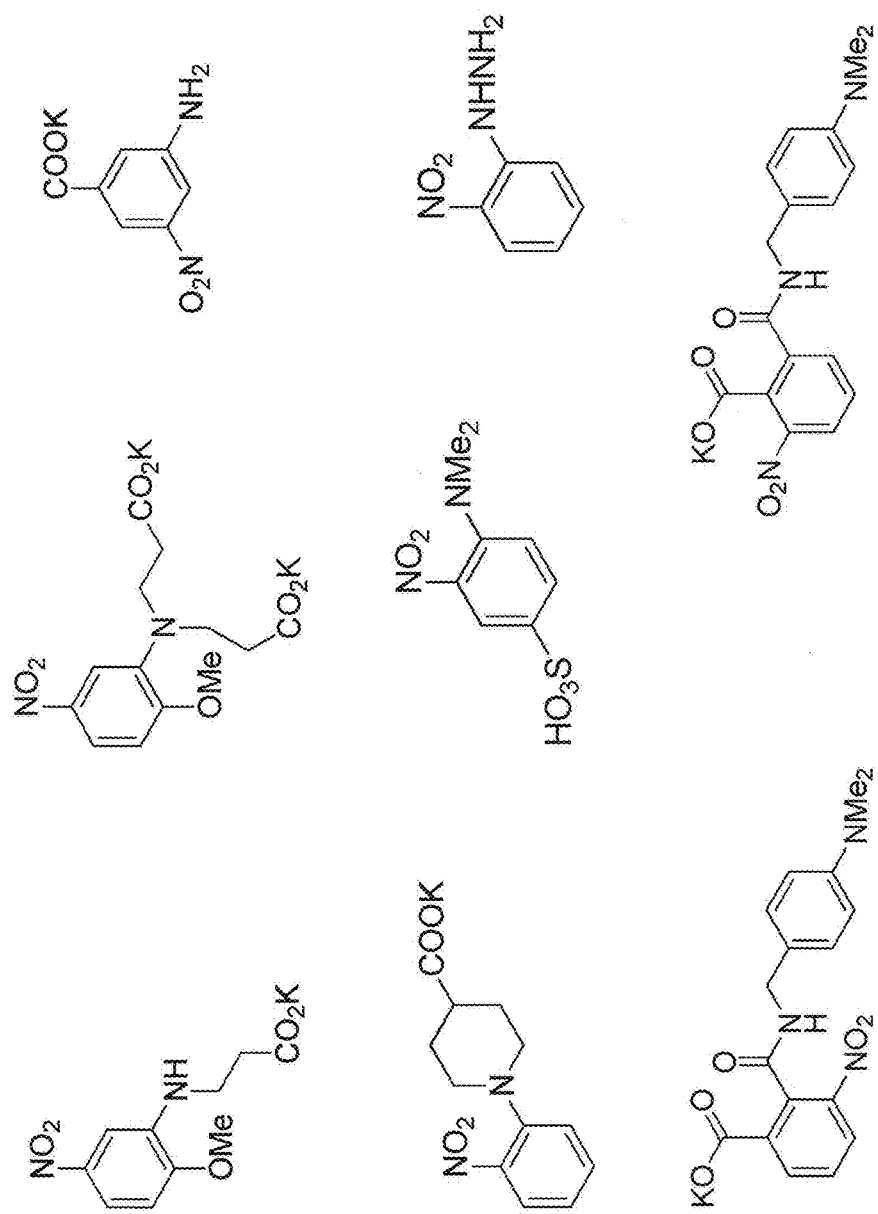
Figure 2:
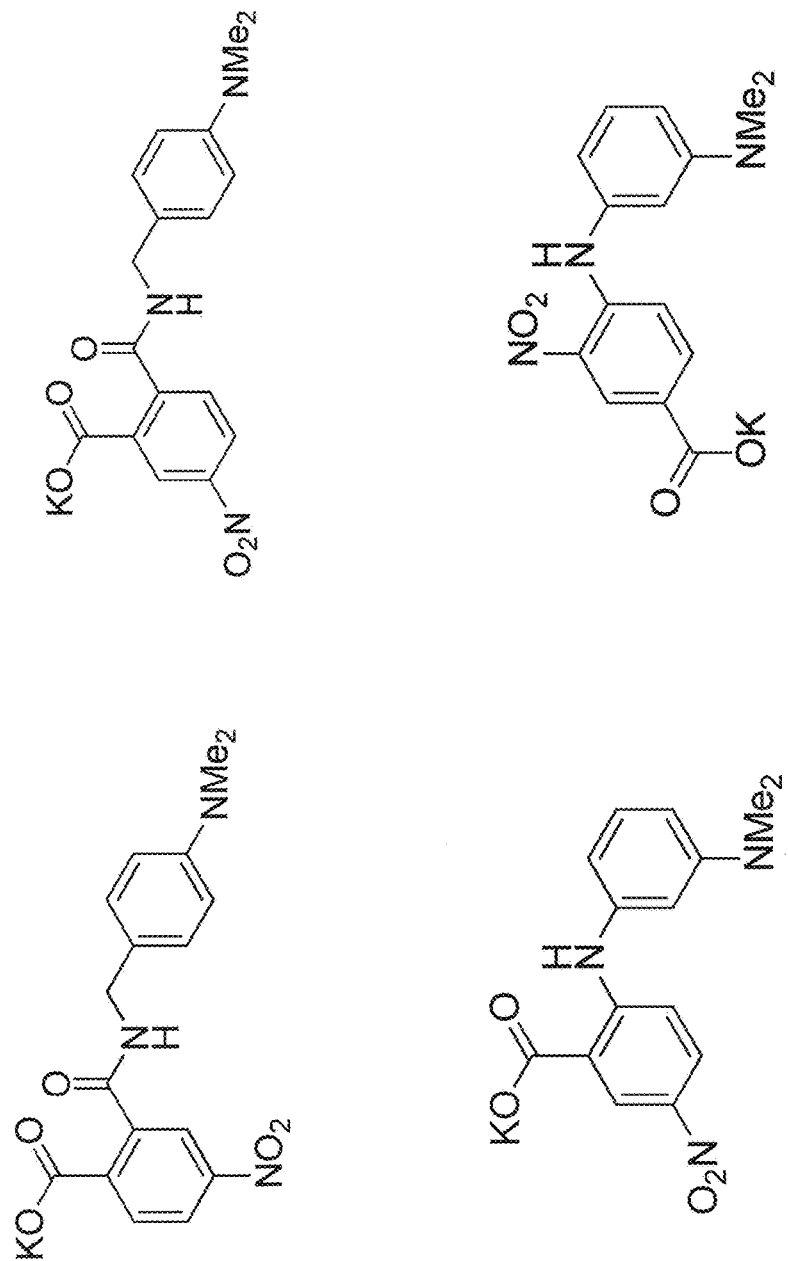
Figure 2:
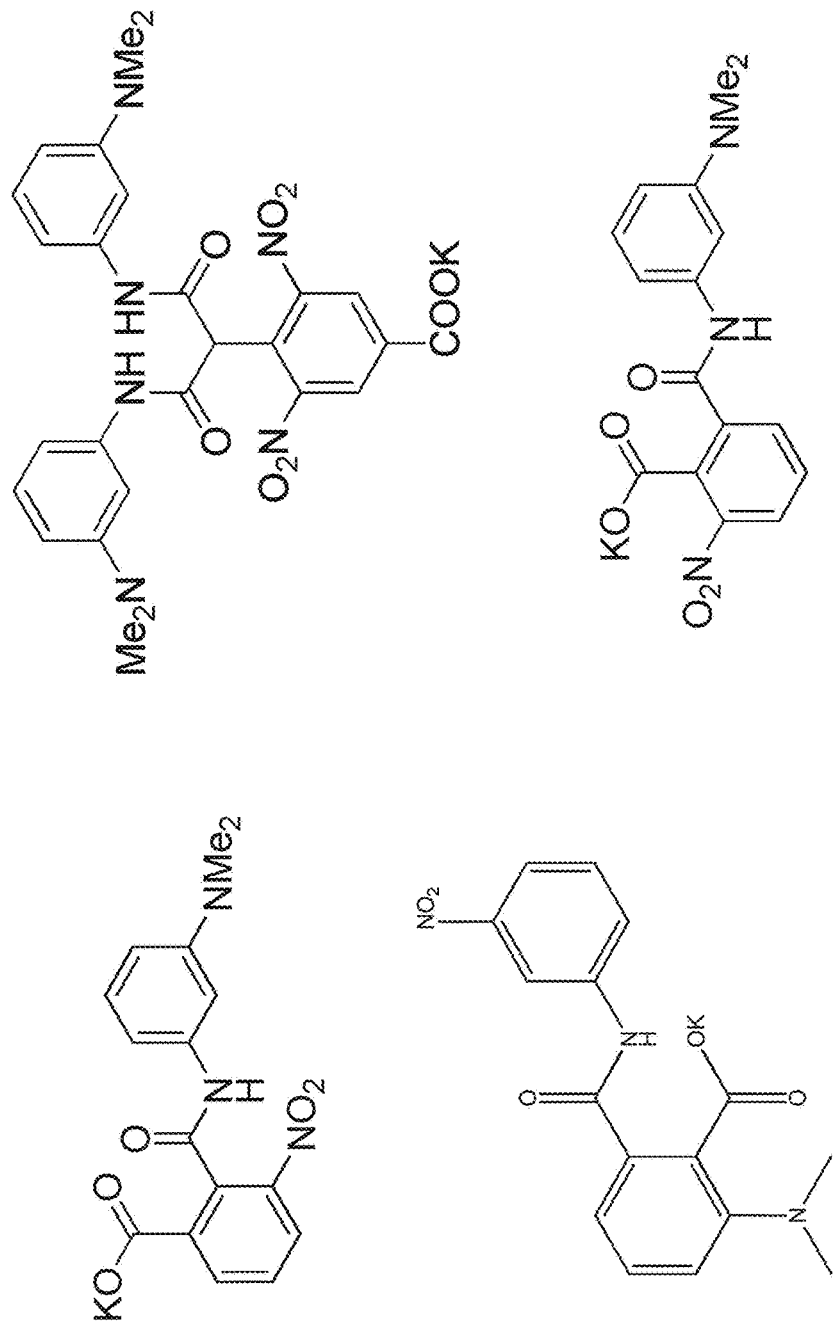
Figure 2:
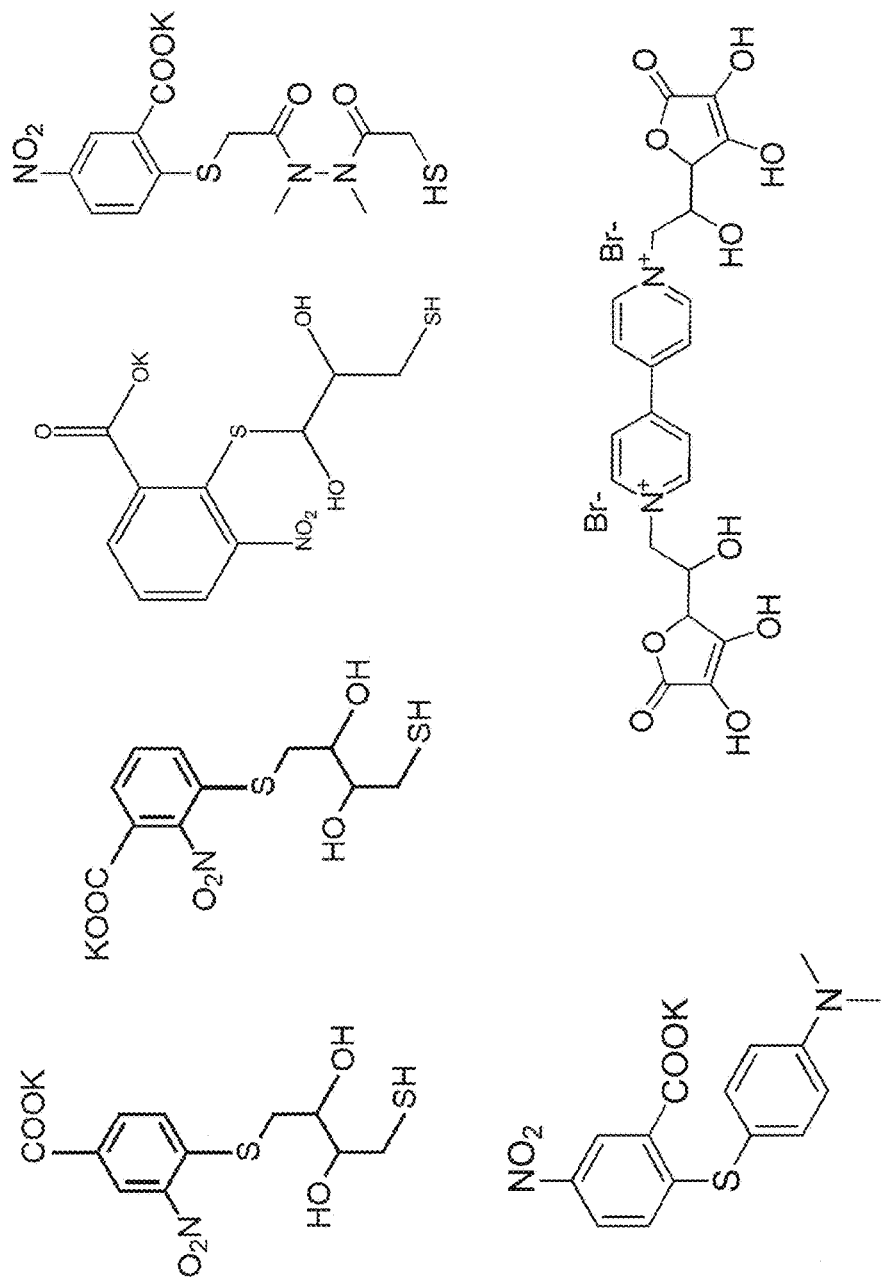

Preferred embodiments of photoprotective agents of the invention are those in which a reducing unit and an oxidizing unit are covalently bound, or physically linked together to form a single molecule, e.g., a water-soluble molecule that can be added to the reaction mixture, e.g., an illuminated reaction mixture. Particularly preferred examples are provided in FIG. 2, and details on preparation of certain of these compounds are found herein in the examples section. In certain aspects, such a molecule comprises: (1) a reducing unit, such as a dialkyl substituted analine, a thiol, an aliphatic amine, or an aromatic amine; and (2) an oxidizing unit, such as a substituted nitrobenzene derivative. Where a higher solubility of the compound is desired, the compound can further comprise a water solubilizing unit, such as a carboxylic acid or sulfonyl, or a salt thereof (e.g., potassium carboxylate), or other agent that increases water solubility of the compound (e.g., polyethylene glycol, etc.). For example, in some applications a photoprotective agent may be insoluble or water soluble only at low concentrations, so a water solubilizing unit can be incorporated to increase the solubility of the compound and allow higher concentrations, e.g., in reaction mixtures and/or stock solutions. In certain preferred embodiments, single molecule ROXS compounds comprise one or more rings, which can be homo- or heterocyclic rings, and which are preferably five- or six-membered rings, but can comprise a higher-order structure. In some embodiments, one or more of these units are linked to such rings, and they can be linked to the same or different rings. Where both the oxidizing unit and reducing unit are directly or indirectly coupled to a single ring, a meta or para orientation is preferable over an ortho orientation. For example, in a nitrobenzene derivative compound of the invention, the nitrite group is preferably linked to a carbon of the benzene ring that is at least two carbons away from a carbon to which an amine, thiol, or disulfide group is directly or indirectly linked. Where different units are linked to different rings, such rings are typically covalently attached together via a linker, examples of which are provided elsewhere herein. In certain embodiments, the reducing unit is bound to a first ring and the oxidizing unit is bound to a second ring, where the first and second rings are connected via a linker, e.g., a substituted or unsubstituted alkyl chain. For example, a nitrobenzene derivative or nitrobenzoic acid derivative comprising a reducing unit, such as a thiol, disulfide group, or aliphatic or aromatic (homo- or heterocyclic) amine, can be used as a single molecule ROXS compound. Of particular interest are compounds that include a nitrobenzene derivative or nitrobenzoic acid derivative, e.g., nitrobenzoic acid further comprising a thiol, disulfide, or amine group to function as the reducing unit. The nitrite group and linkage to the reducing unit can be present at multiple different positions on the benzene ring, and multiple nitrite groups can also be present, as shown in FIG. 2. Further, although certain of the compounds in FIG. 2 possess a carboxylic acid group as the water solubilizing unit, in certain preferred embodiments a potassium carboxylate group or other carboxylate salt is used, which can further increase the solubility of the compound. Likewise, although certain of the compounds in FIG. 2 possess a potassium carboxylate group as the water solubilizing unit, in certain embodiments a carboxylic acid group or other carboxylate salt is used in place of the potassium carboxylate group. Other compounds can be similarly constructed, e.g., by combining both methylviologen and ascorbic acid into a single compound, e.g., using a linker, e.g., as described elsewhere herein.

The terms oxidation and reduction describe chemical reactions in which atoms have their oxidation number (oxidation state) changed, e.g., an atom can undergo reduction of oxidation number (reduction) or an increase in oxidation number (oxidation). Substances that have the ability to oxidize other substances are said to be oxidative and are known as oxidizing agents, oxidants, or oxidizers. For example, an oxidant removes electrons from another substance, and is itself reduced. And, because it "accepts" electrons, it is also called an electron acceptor. Oxidizing agents in organic chemistry are those that increase the oxygen content or decrease the hydrogen content of an organic molecule. Substances that have the ability to reduce other substances are said to be reductive and are known as reducing agents, reductants, or reducers. For example, a reducing agent transfers electrons to another substance, and is itself oxidized. And, because it "donates" electrons, it is also called an electron donor. Electron donors can also form charge transfer complexes with electron acceptors. Reducing agents are those that cause another compound to increase hydrogen content or decrease its oxygen content. As used herein, a "reducing unit" includes or is a reducing agent, and an "oxidizing unit" is or includes an oxidizing agent.

Both types of groups are well known to those of skill in the art. Preferred reducing units that can be combined with oxidizing units to create photoprotective agents that are single compound TSQ reagents of the invention, include, but are not limited to, anilines (e.g., N,N-dialkyl anilines, such as 4-(dimethylamino)phenylacetic acid or 4-(dimethylamino)benzoic acid; 3-(N-carboxyethylamino)-4-methoxy-nitrobenzoic acid; or 3-(N,N-bis-carboxyethylamino)-4-methoxy-nitrobenzoic acid), ascorbic acid, anthracenes, thiols, disulfides, aromatic heterocyclic amines, aromatic homocyclic amines, aliphatic amines, dimethyl methylphosphonate (DMMP), dimethylaminopropylamine (DMAPA), and the like and derivatives and/or salts (e.g., potassium salts) thereof (e.g., 3-(N-carboxyethylamino)-4-methoxy-nitrobenzene, potassium salt; or 3-(N,N-bis-carboxyethylamino)-4-methoxy-nitrobenzene, dipotassium salt). Other reducing agents that can be incorporated into a single molecule ROXS compound of the invention include, but are not limited to, N-propyl gallate, mercaptoethanol, 6-hydroxy-2,5,7,8-tetramethylchroman-2-carboxylic acid and derivatives thereof, active metals such as potassium, calcium, barium, sodium and magnesium, and compounds that contain a hydrogen ion, such as $NaH$, $LiH_2$ $LiAlH_4$ and $CaH_4$, formic acid, oxalic acid, sulfites, and many others known to those of skill in the art.

Preferred oxidizing units that can be combined with reducing units to create photoprotective agents that are single compound TSQ reagents, include, but are not limited to, aromatic nitro derivatives such as nitrobenzoic acid, quinones, methylviologen, and the like and derivatives thereof. For example, in preferred embodiments a generic structure of a compound of the invention is a nitro-substituted aniline, e.g.,

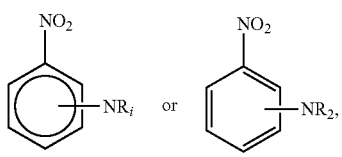

where each R can be a hydrogen atom (H) or comprise an alkyl group, e.g., an unbranched alkyl group, a branched alkyl group, a substituted alkyl group, or a combination thereof. In certain preferred embodiments, however, the photoprotective agent does not comprise a quinone, hydroquinone, or a derivative thereof. Additional oxidizing compounds that can be incorporated into a single molecule ROXS compound of the invention include, but are not limited to, halogen containing compounds, peroxides, hypochlorite, permanganate and magnate compounds, and many other known to those of skill in the art. In certain embodiments, multiple reducing units and/or oxidizing units can be linked to construct a single molecule ROXS compound. For example, methylviologen can be linked to two reducing units, e.g., thiol groups.

The term "linker" encompasses any moiety that is useful to connect one or more molecules or compounds (including, e.g., reducing units, oxidizing units, and/or water solubilizing units), e.g., to each other and/or to a reaction site. For example, a linker can connect a photoprotective agent (e.g., a triplet-state quencher, free radical quencher, or single molecule ROXS described herein) to a reaction site or a reaction component (e.g., an enzyme or fluorescent reaction component); a linker can attach a reporter molecule or "label" (e.g., a fluorescent dye) to a reaction site or a reaction component (e.g., an enzyme, substrate, ligand, binding partner, etc.); and a linker can covalently link a reducing agent to a oxidizing agent to form a single molecule ROXS. Methods for choosing, synthesizing, and attaching linkers to reactants and surfaces are well known to those of ordinary skill in the art and further discussion and exemplary linker moieties are provided, e.g., in U.S. Ser. No. 61/026,992 (filed Feb. 7, 2008), U.S. Ser. No. 12/367,411, (filed Feb. 6, 2009), and U.S. Published Patent Application No. 2009/0233302, the disclosures of which are incorporated herein by reference in their entireties for all purposes. For example, by keeping a photoprotective agent in close proximity to a fluorescent label, the efficiency of suppressing and/or reversing triplet state formation may be enhanced. (See, e.g., U.S. Patent Publication No. 2009/0325260, which is incorporated herein by reference in its entirety for all purposes.) In certain embodiments, a photoprotective agent is bound to a linker that connects a fluorescent label to a reactant, such as an enzyme substrate. A specific example would be to place a photoprotective agent in a linker that connects a nucleoside polyphosphate to a fluorescent dye:

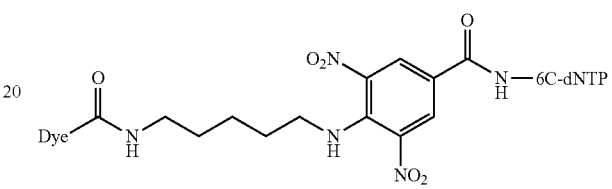

Although designated at "dNTP" in the above structure, the nucleotide polyphosphate may comprise three or more phosphate groups, and it may be a deoxyribonucleoside polyphosphate or a ribonucleoside polyphosphate. More than one photoprotective agent can be incorporated onto a fluorescent dye molecule:

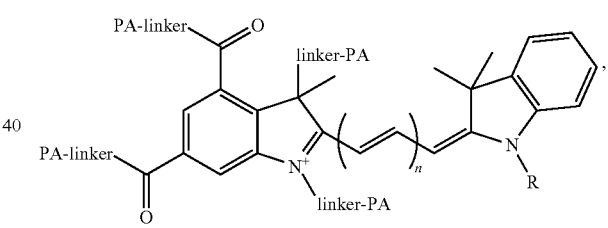

where "PA" is indicative of a photoprotective agent that is preferably a triplet state quencher, but may also be another type of photoprotective agent. In certain preferred embodiments, n=1, 2, or 3. One specific example is:

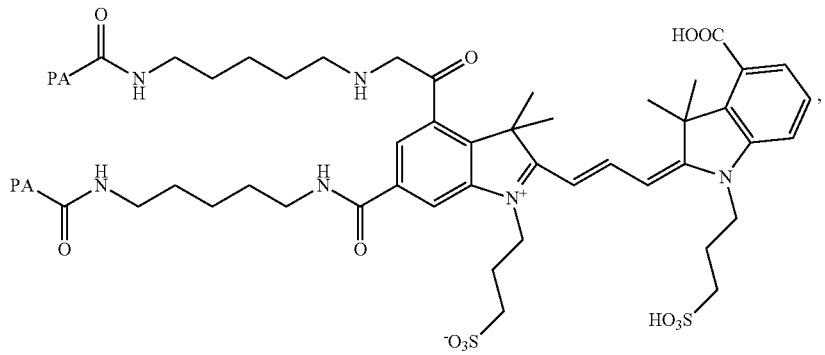

where the photoprotective agent can be selected from those provided herein. In certain preferred embodiments, photoprotective agents included within a labeled nucleoside polyphosphate construct are selected from:

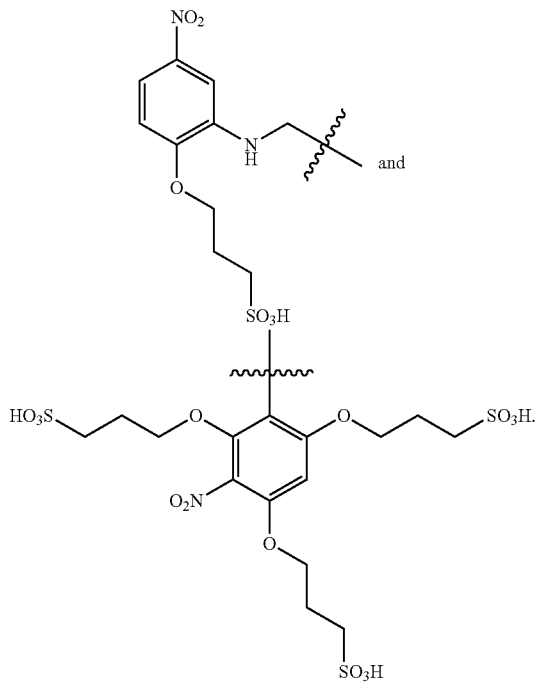

The sulfonyl groups both increase the bulkiness of the labeled nucleoside polyphosphate and its hydrophilicity. It is beneficial to keep the photoprotective agent apart from the dye core to mitigate any quenching, e.g., due to the nitro group, while allowing a proximity sufficient to enhance effective prevention or reversal of triplet state formation.

Linkers may also be branched to connect three or more components of a reaction mixture, e.g., in to a tridentate, tetradentate, or higher order structure. For example, a dye may be linked to one or more photo-induced damage mitigating agents, enzymes, or other reaction components. In some such embodiments, a tridendate or higher order (e.g., tetradentate, pentadentate, hexadentate, etc.)) structure may be formed connecting the photo-induced damage mitigating agent to two or more different reaction components and/or to a reaction site. For example, the photo-induced damage mitigating agent can be incorporated into a linker connecting two other components of the reaction. Methods of producing such compounds are provided, e.g., in U.S. Ser. No. 61/026, 992 (filed Feb. 7, 2008) and U.S. Ser. No. 12/367,411, (filed Feb. 6, 2009), both of which are incorporated herein by reference in their entireties for all purposes. In a single molecule sequencing reaction, such a tridendate structure may include a photo-induced damage mitigating agent, a dye, and a nucleoside polyphosphate, for example. Such an embodiment may be beneficial to bring the photo-induced damage mitigating agent near the dye to facilitate rapid quenching of any triplet state occurring in the dye molecule. In certain preferred embodiments, a luminescently labeled reaction component (e.g., fluorescent nucleoside polyphosphate, enzyme, etc.) is linked to at least one photo-induced damage mitigating agent provided herein.

In certain embodiments, the linker is a member selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl. In one example, the linker moiety is selected from straight- and branched carbon-chains, optionally including at least one heteroatom (e.g., at least one functional group, such as ether, thioether, amide, sulfonamide, carbonate, carbamate, urea and thiourea), and optionally including at least one aromatic, heteroaromatic or non-aromatic ring structure (e.g., cycloalkyl, phenyl). In certain embodiments, molecules that have trifunctional linkage capability are used, including, but are not limited to, cynuric chloride, mealamine, diaminopropanoic acid, aspartic acid, cysteine, glutamic acid, pyroglutamic acid, S-acetylmercaptosuccinic anhydride, carbobenzoxylysine, histine, lysine, serine, homoserine, tyrosine, piperidinyl-1, 1-amino carboxylic acid, diaminobenzoic acid, etc.

The linker as a whole may comprise a single covalent bond or a series of stable bonds. Thus, a reporter molecule (e.g., a fluorescent dye) may be directly attached to a triplet-state or free radical quencher of the invention (e.g., a nitrobenzene derivative or nitrobenzoic acid derivative comprising a thiol or amine). A linker that is a series of stable covalent bonds can incorporate non-carbon atoms, such as nitrogen, oxygen, sulfur and phosphorous, as well as other atoms and combinations of atoms, as is known in the art. If the linker is not directly attached to a reactant by a single covalent bond, the attachment may comprise a combination of stable chemical bonds, including for example, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In an exemplary embodiment, the dye is conjugated to a nucleoside triphosphate as an alkylated tetraphosphate analog. In other embodiments, other polyphosphate derivative can be used, e.g., a polyphosphate with 3 to 7 phosphate groups, wherein the polyphosphate can further comprise a linker between a phosphate subunit and a fluorescent reporting moiety. A particularly preferred example is a dye labeled hexaphosphate derivative.

In certain preferred embodiments, linkers are derived from molecules which comprise at least two reactive functional groups (e.g., one on each terminus), and these reactive functional groups can react with complementary reactive functional groups on the various reaction components or used to immobilize one or more reaction components at the reaction site. "Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application or modification for a particular purpose is within the ability of one of skill in the art (see, for example, Sandler and Karo, eds. ORGANIC FUNCTIONAL GROUP PREPARATIONS, Academic Press, San Diego, 1989).

In certain embodiments, the compounds provided herein may be used in combination with one another and/or with a variety of reducing agents, anti-fade agents, free radical quenchers/scavengers, oxygen scavengers, singlet oxygen quenchers, and/or triplet-state quenchers (e.g., 6-hydroxy-2,5,7,8-tetramethylchroman-2-carboxylic acid), including, for example, those provided in U.S. Patent Publication Nos. 20070161017 and 20100136592, previously incorporated by reference, which also provide methods of mitigating the impact of photo-induced damage on the results of a given analytical operation that may be used with the compounds and methods of the provided herein.

In certain embodiments, a photo-induced damage mitigating agent is a mixture of at least two different photoprotective compounds or a combination of derivatives of the same type of compound, e.g., at least about 2, 3, 4, 5, 6, or 7 single molecule ROXS compounds, e.g., as provided in FIG. 2, can be used together to provide mitigation of photo-induced damage. Alternatively, additional mitigation compounds such as 6-hydroxy-2,5,7,8-tetramethylchroman-2-carboxylic acid, mercaptoethanol, methylviologen, ascorbic acid, quinones, dithiothreitol, and the like and derivatives thereof can be mixed with the single molecule ROXS compounds of the invention. Such a mixture can comprise various ratios of any two of its constituent components, e.g., about 60:1, 40:1, 20:1, 10:1, 8:1, 6:1, 4:1, 2:1, 3:2, 1.5:1 1:1, 1:1.5, 2:3, 1:2, 1:4, 1:6, 1:8, 1:10, 1:20, 1:40, 1:60, etc. For example, there may be substantially equivalent amounts of multiple or each compound in the mixture or a single component, e.g., one or more ROXS compounds, or one of the compounds may be mixed in a significantly higher concentration than at least one other. In some embodiments, a mixture of at least two different ROXS compounds provided herein comprises various percentages of its constituent compounds.

Figure 3:
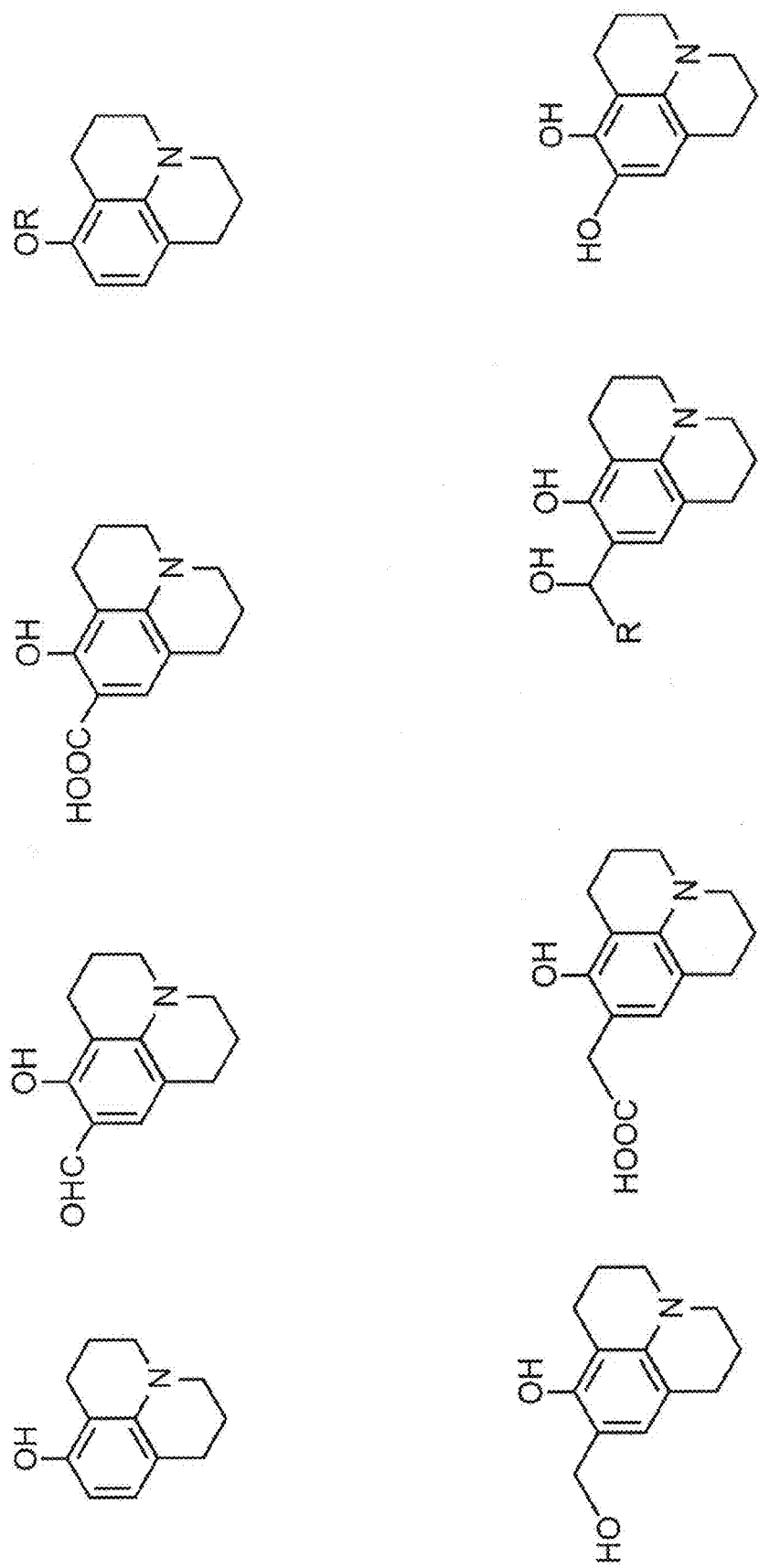
FIG. 3 provides additional photoprotective agents of the invention, e.g., hydroxyjulolideine derivatives.
Figure 4:
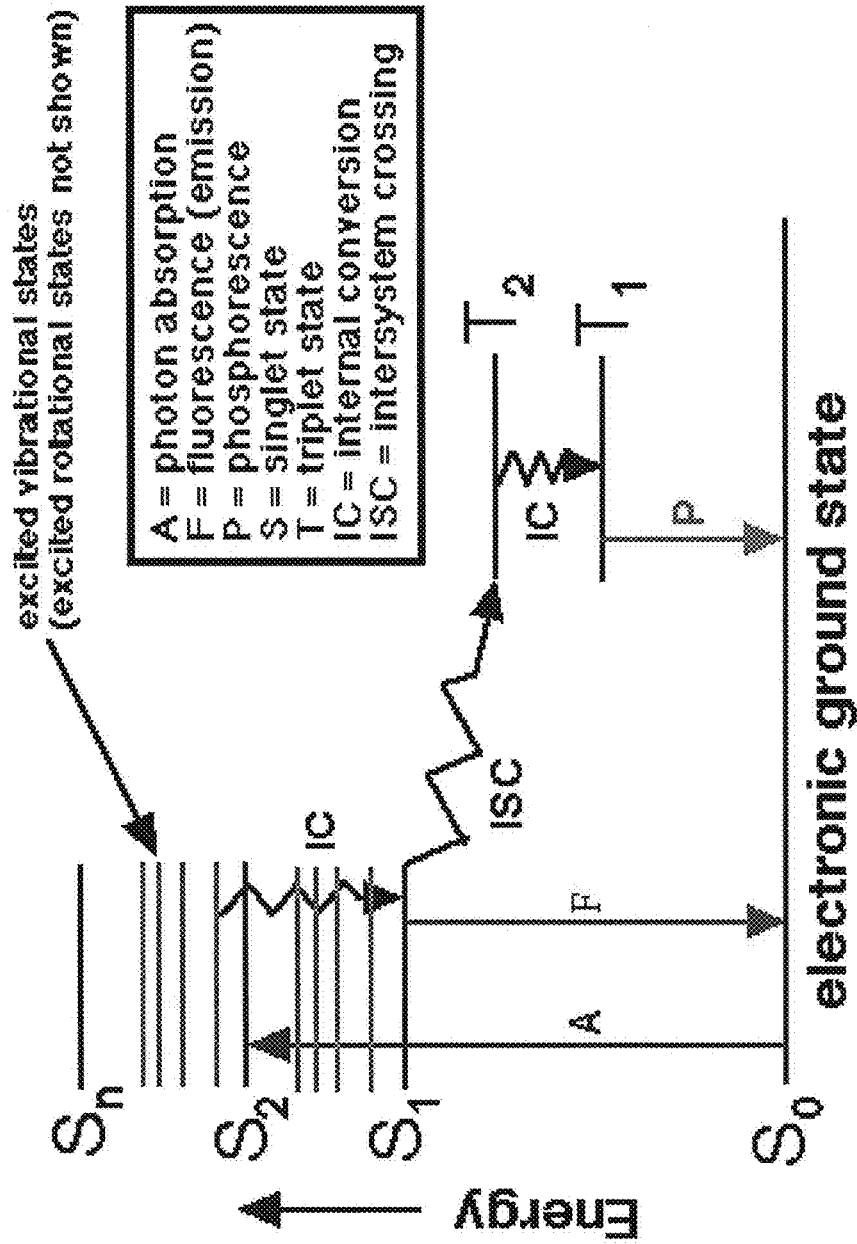
FIG. 4 is a Jablonski diagram illustrating excited vibrational states.

Additional photoprotective compounds can also be added to a reaction mixture. For example, 8-hydroxyjulolidine or derivatives thereof can be added to a reaction mixture as a triplet state quencher or these molecules can be coupled to the dye molecule or a reactant in an illuminated reaction. Examples of hydroxyjulolidine derivatives that can be used as TSQ reagents are provided in FIG. 3.

These approaches are particularly useful in the optical interrogation of reactions where components of the reaction that are susceptible to photo-induced damage are spatially confined on an assay plate or substrate, either through the presence of structural confinements, optical confinements, and/or through immobilization of the components. Examples of such confined reagents include surface immobilized or localized reagents, e.g., surface immobilized or associated enzymes, receptors, antibodies, etc. that are interrogated upon the surface, e.g., through fluorescence scanning microscopy or scanning confocal microscopy, total internal reflectance microscopy or fluorometry, surface imaging, or the like.

In accordance with the present invention, photo-induced damage mitigating agents may generally be provided as a component of the reaction mixture, either through addition as an additive, either liquid or solid, and can be predisposed and/or immobilized within the region where the reaction is taking place, or may be provided in a configuration that permits them to freely interact with the aqueous system components by including such agents within or linked to structures (e.g., caging groups, tridentate structures, etc.) that render the agents suspended in aqueous systems and additionally available to interact with relevant portions of the reaction mixture, e.g., dissolved oxygen species. By way of example, in cases where the reaction of interest is confined to a particular region or location, it may be desirable to immobilize or otherwise localize the photo-induced damage mitigating agents within or proximal to that region, e.g., upon the surfaces of the substrates or reactions wells. Likewise, where a photo-induced damage mitigating agent comprises cooperatively functioning components, e.g., dual enzyme systems, it may again be desirable to localize such components relative to each other, as well as to the reaction of interest.

As used herein, a substrate may comprise any of a variety of formats, from planar substrates, e.g., glass slides or planar surfaces within a larger structure, e.g., a multi-well plates such as 96-well, 384-well, and 1536-well plates, or regularly spaced micro- or nano-porous substrates (e.g., arrays of zero mode waveguides). Such substrates may also comprise more irregular porous materials, such as membranes, aerogels, fibrous mats, or the like, or they may comprise particulate substrates, e.g., beads, spheres, metal or semiconductor nanoparticles, optical fibers, or the like.

In addition to the foregoing, it will be appreciated that the other reagents in a given reaction of interest, including those reagents for which photo-induced damage is being mitigated in accordance with the invention, may be provided in any of a variety of different configurations. For example, they may be provided free in solution, or complexed with other materials, e.g., other reagents and/or solid supports. Likewise, such reagents may be provided coupled to beads, particles, nanocrystals or other nanoparticles, or they may be tethered to larger solid supports, such as matrices or planar surfaces. These reagents may be further coupled or complexed together with other reagents, or as separate reagent populations or even as individual molecules, e.g., that are detectably resolvable from other molecules within the reaction space. In addition, for purposes of discussion herein, whether a particular reagent is confined by virtue of structural barriers to its free movement or is chemically tethered or immobilized to a surface of a substrate, it will be described as being "confined." For example, in some preferred embodiments, one or more reagents in an assay system are confined within an optical confinement. Such an optical confinement may be an internal reflection confinement (IRC) or an external reflection confinement (ERC), a zero mode waveguide, or an alternative optical structure, such as one comprising porous film with reflective index media or a confinement using index matching solids. More detailed descriptions of various types of optical confinements are provided, e.g., in International Application Publication No. WO/2006/083751, U.S. Pat. No. 6,917,726, and U.S. Pat. No. 7,170,050, the full disclosures of which are incorporated herein by reference in their entireties for all purposes.

V. Exemplary Applications

As noted above, the methods and compositions of the invention are useful in a broad range of illuminated analytical reactions, and particularly those using photoluminescent or fluorescent reactants, and particularly such reactions where the reagents that are susceptible to photo-induced damage are present at relatively low levels. One exemplary application of the methods and compositions described herein is in single molecule analytical reactions, where the reaction of a single molecule (or very limited number of molecules) is observed in the analysis, such as observation of the action of a single enzyme, receptor, or antibody molecule. In particular, when an analysis relies upon a small population of reagent molecules, damage to any significant fraction of that population will have a substantial impact on the analysis being performed. For example, prolonged interrogation of a limited population of reagents, e.g., fluorescent analogs and enzymes, can lead to photo-induced damage of the various reagents to the point of substantially impacting the activity or functionality of the enzyme. In particular, it has been shown that prolonged illumination of DNA polymerases involved in synthesis using fluorescent nucleotide analogs results in a dramatic decrease in the enzyme's ability to synthesize DNA, often measured as a reduction in read length. Without being bound to any theory of operation, it is believed that in some cases the photo-induced damage event affects the catalytic region of the enzyme thus affecting either the ability of the enzyme to remain complexed with the template, or its ability to continue synthesis. The compositions and methods of the present invention can prevent or mitigate that impact by providing photo-induced damage mitigating agents in the reaction mixture.

In general, the photo-induced damage mitigating agents described herein are present in the reaction mixture at levels sufficient to provide beneficial impact, e.g., reduced photo-induced damage and/or extension of the photo-induced damage threshold period, but are not present at levels that interfere substantially with the reaction of interest, e.g., the sequencing reaction. For example, the preferred compounds of the invention combine an oxidizing unit and a reducing unit onto a single molecule to decrease the amount of photo-induced damage mitigating reactants are needed. In certain preferred embodiments, the photo-induced damage mitigating agents are present at 0.5-10.0 mM, or more preferably between about 0.5 mM and 5 mM, which represents the total concentration of a single or a combination of photo-induced damage mitigating agents presented herein. However, these concentrations are merely exemplary and may be change depending on various factors including, e.g., the particular photo-induced damage mitigating agent and/or mixture thereof, the type of reaction to which it is added, conditions under which such reaction is to be performed, and the like. Such adjustments are well within the abilities of the ordinary practitioner.

In another aspect, the present invention is directed to illuminated reactions for single molecule analysis, including sequencing of nucleic acids by observing incorporation of nucleotides or nucleotide analogs into a nascent nucleic acid sequence during template-directed polymerase-based synthesis. Such methods, generally referred to as "sequencing-by-incorporation," often involve the observation of the addition of nucleotides or nucleotide analogs in a template-dependent fashion in order to determine the sequence of the template strand. See, e.g., U.S. Pat. Nos. 6,780,591, 7,037, 687, 7,344,865, 7,302,146; U.S. Patent Publication Nos. 20100075327 and 20070036511; U.S. patent application Ser. No. 12/767,673, filed Apr. 26, 2010; U.S. patent application Ser. No. 12/635,618, filed Dec. 10, 2009; and Eid, et al. (2009) Science 323:133-138, all of which are incorporated herein by reference in their entireties for all purposes. Processes for performing this detection typically include the use of fluorescently labeled nucleotide analogs within a confined observation region, e.g., within a nanoscale well and/or tethered, either directly or indirectly to a surface. By using excitation illumination (i.e., illumination of an appropriate wavelength to excite the fluorescent label and induce a detectable signal), the fluorescently labeled bases can be detected as they are incorporated into the nascent strand, thus identifying the nature of the incorporated base, and as a result, the complementary base in the template strand. It will be understood that many different kinds of reactions can also benefit through use of the methods, compositions, and systems provided herein, e.g., including those described in U.S. patent application Ser. Nos. 12/813,968 and 12/814,075, both of which were filed Jun. 11, 2010, and are incorporated herein by reference in their entireties for all purposes.

One particularly preferred aspect of the invention is in conjunction with the sequencing by incorporation of nucleic acids within an optical confinement, such as a zero mode waveguide. Such reactions involve observation of an extremely small reaction volume in which one or only a few polymerase enzymes and their fluorescent substrates may be present. Zero mode waveguides, and their use in sequencing applications are generally described in U.S. Pat. Nos. 6,917, 726 and 7,033,764, and preferred methods of sequencing by incorporation are generally described in Published U.S. Patent Application No. 2003-0044781, the full disclosures of which are incorporated herein by reference in their entireties for all purposes, and in particular for their teachings regarding such sequencing applications and methods. Briefly, arrays of zero mode waveguides ("ZMWs"), configured in accordance with the present invention may be employed as optical confinements for single molecule analytical reactions, e.g., for nucleic acid (e.g., DNA, RNA) sequence determination. In particular, as noted above, these ZMWs provide extremely small observation volumes at or near the transparent substrate surface, also termed the "base" of the ZMW. A nucleic acid synthesis complex, e.g., template sequence, polymerase, and primer, which is immobilized at the base of the ZMW, may then be specifically observed during synthesis to monitor incorporation of nucleotides or nucleotide analogs in a template-dependent fashion, and thus provide the identity and sequences of nucleotides or nucleotide analogs in the template strand. This identification is typically accomplished by providing detectable label groups, such as fluorescent labeling molecules, on the nucleotides or nucleotide analogs. In some instances, the labeled nucleotides or nucleotide analogs terminate primer extension, allowing a "one base at a time" interrogation of the complex. If, upon exposure to a given labeled base, a base is incorporated, its representative fluorescent signal may be detected at the base of the ZMW. If no signal is detected, then the base was not incorporated and the complex is interrogated with each of the other bases, in turn. Once a base is incorporated, the labeling group is removed, e.g., through the use of a photocleavable linking group or enzymatic cleavage of the alpha phosphate, and where the label was not the terminating group, a terminator, upon the 3' end of the incorporated nucleotide or nucleotide analog, may be removed prior to subsequent interrogation.

In accordance with the present invention, the above-described sequencing reaction may be carried out in the presence of one or more photo-induced damage mitigating agents (e.g., single molecule ROXS compounds and conjugates and mixtures thereof) provided herein, either alone or in combination with other reaction mixture additives, such as reducing agents, antifade agents, free radical quenchers, triplet-state quenchers, singlet oxygen quenchers, or enzyme systems for depletion of oxygen species (e.g., comprising an oxidase). In certain preferred embodiments, the sequencing reactions may be carried out in the presence of at least one of the photoprotective agents described herein. For example, a photo-induced damage mitigating agent may be a compound in which a reducing unit is covalently bound to an oxidizing unit to form a single molecule ROXS triple state quencher.

In another aspect, the illuminated reaction mixture includes a nucleoside polyphosphate connected to a fluorescent dye by a linker. The linker in such a reaction mixture itself may comprise one or more photo-induced damage mitigating agents, such as single molecule ROXS compounds, hydroxyjulolidene derivatives, oxidizing units, reducing units, or mixtures thereof.

In addition to the use of photo-induced damage mitigating agents, the present invention also provides alternative methods of mitigating the impact of photo-induced damage on a reaction. Such alternative methods can be used in combination with the compositions and methods described above to further alleviate the effects of species that can be generated during an illuminated reaction.

One alternative method of mitigating the impact of photo-induced damage on the results of a given reaction is by only interrogating a reaction mixture, e.g., detecting fluorescent emission, during such portion of the illumination period before which excessive photo-induced damage has occurred. This approach is particularly useful in the optical interrogation of reactions where components of the reaction that are susceptible to photo-induced damage are spatially confined on an assay plate or substrate, either through the presence of structural confinements and/or through immobilization of the components. Examples of such confined reagents include surface immobilized or localized reagents, e.g., surface immobilized or associated enzymes, antibodies, etc. that are interrogated upon the surface, e.g., through fluorescence scanning microscopy or scanning confocal microscopy, total internal reflectance microscopy or fluorometry, surface imaging, or the like. The timing of observation of each reaction is determined based on knowledge of the photodamage threshold period, as described elsewhere herein. A given reaction or set of reactions is monitored under illumination for a period that is less than the photodamage threshold period, followed by a redirection of the illumination to a second, preferably adjacent, reaction or set of reactions, which were not previously subjected to the illumination. This second reaction or set of reactions is also observed for a period less than the photodamage threshold period, before the illumination is redirected to a third reaction or set of reactions, and so on. Further details are provided in U.S. Patent Publication No. 20070161017, incorporated herein by reference in its entirety for all purposes.

Another alternative method of mitigating the impact of photo-induced damage on the results of a given reaction provides for the elimination of potentially damaging oxygen species using means other than the use of the photo-induced damage mitigating agents described above. In one example, dissolved oxygen species may be flushed out of aqueous systems by providing the reaction system under different gas environments, such as by exposing an aqueous reaction to neutral inert gas environments, such as argon, nitrogen, helium, xenon, or the like, to prevent dissolution of excess oxygen in the reaction mixture. By reducing the initial oxygen load of the system, it has been observed that photo-induced damage effects, e.g., on polymerase mediated DNA synthesis, is markedly reduced. In particularly preferred aspects, the system is exposed to a xenon atmosphere. In particular, since xenon can be induced to form a dipole, it operates as a triplet-state quencher in addition to supplanting oxygen in the aqueous system. (See, e.g., Vierstra and Poff, Plant Physiol. 1981 May; 67(5): 996-998, which is incorporated herein by reference in its entirety for all purposes) As such, xenon would also be categorized as a quencher, as set forth above.

It is to be understood that the above description is intended to be illustrative and not restrictive. It readily should be apparent to one skilled in the art that various embodiments and modifications may be made to the invention disclosed in this application without departing from the scope and spirit of the invention. For example, in certain embodiments various photo-induced damage mitigating agents and systems can be combined within a single reaction mixture, in particular where their modes of action differ and/or complement one another. The scope of the invention should, therefore, be determined not with reference to the above description, but should instead be determined with reference to the appended claims, along with the full scope of equivalents to which such claims are entitled. All publications mentioned herein are cited for the purpose of describing and disclosing reagents, methodologies and concepts that may be used in connection with the present invention. Nothing herein is to be construed as an admission that these references are prior art in relation to the inventions described herein. Throughout the disclosure various patents, patent applications and publications are referenced. Unless otherwise indicated, each is incorporated by reference in its entirety for all purposes.

VI. Examples

The following non-limiting examples illustrate methods of making and using various photoprotective compounds of the invention.

Preparation of

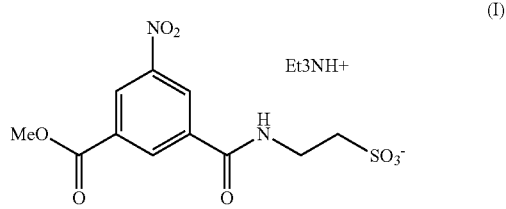

A mixture of 1.23 g of mono-methyl-5-nitroisophthalate, 2.41 g of N,N,N',N'-Tetramethyl-O—(N-succinimidyl)uronium tetrafluoroborate and 1.4 mL of triethylamine was stirred in 25 mL of DMF at room temperature for 15 minutes. In a separate flask, an aqueous solution of 3.13 g of taurine in 30 mL of 1 M NaHCO3 was prepared. The DMF solution was then added to the aqueous solution via a separatory funnel and the mixture was stirred at room temperature for about an hour. All volatile components were evaporated and the crude material was purified on a silica gel column eluting with acetonitrile and water to yield 1.09 g of product.

Preparation of

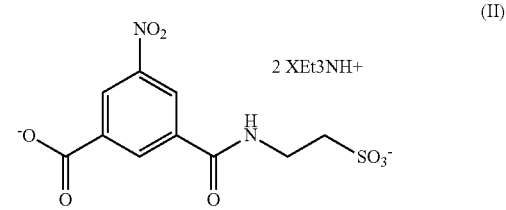

To 0.675 g of (I)-65 in 15 mL of water, 0.91 mL of triethylamine was added and the mixture was stirred at room temperature for 4 hours. Volatile components were removed under reduced pressure to recover the product which can be used without further purification.

Preparation of

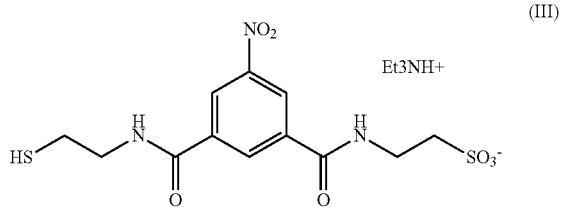

To 1.089 g of SY360-(II) in 20 mL of DMF at room temperature, 0.65 g of N,N,N',N'-Tetramethyl-O—(N-succinimidyl)uronium tetrafluoroborate and 0.84 mL of triethylamine were added and stirred t room temperature for 20 minutes. At the end of the period, 0.35 g of cyteamine was added and stirred for 1 hour. Volatile components were removed under reduced pressure and the crude was purified on a silica gel column eluting with acetonitrile and water to yield 0.173 g of the desired product.

Preparation of

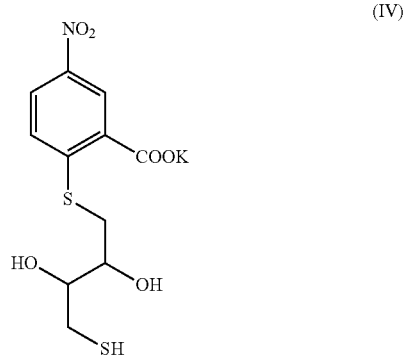

A mixture of 0.2 g of 2-chloro-5-nitrobenzoic acid, 0.462 g of dithiothreitol (DTT), and 0.35 mL of triethylamine in 2 mL of DMF was heated at 50 C for 20 hours. The reaction was then diluted with about 30 mL of 1 N HCl and extracted with ethyl acetate and dried over magnesium sulfate. The crude product thus obtained was purified on HPLC to obtain 0.235 g of product as its triethylammonium salt which was replaced by potassium by adding 1 equivalent of KOH in aqueous medium.

Preparation of

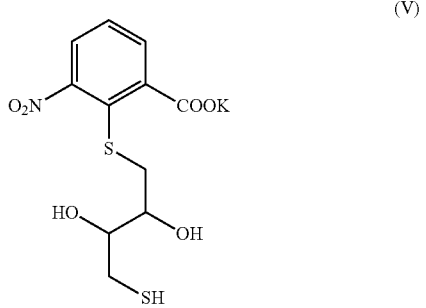

This compound was prepared by starting with a mixture of 0.2 g of 2-bromo-3-nitrobenzoic acid, 0.462 g of dithiothreitol (DTT), and 0.35 mL of triethylamine in 2 mL of DMF. The mixture is then heated at 50 C for 20 hours. The reaction is then diluted with about 30 mL of 1 N HCl and extracted with ethyl acetate and dried over magnesium sulfate. The crude product thus obtained can be purified on HPLC to obtain the product as its triethylammonium salt which can be replaced by potassium by adding 1 equivalent of KOH in aqueous medium.

Preparation of

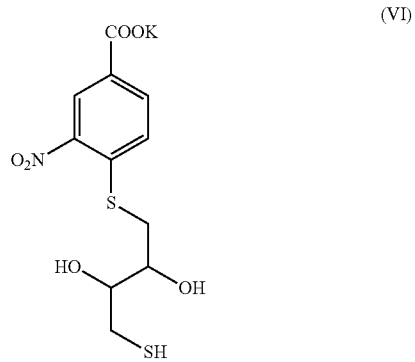

This compound was prepared by starting with a mixture of 4-chloro-3-nitrobenzoic acid, dithiothreitol (DTT), and triethylamine in 2 mL of DMF. The mixture is then heated at 50 C for 20 hours. The reaction is then diluted with about 30 mL of 1 N HCl and extracted with ethyl acetate and dried over magnesium sulfate. The crude product thus obtained can be purified on HPLC to obtain the product as its triethylammonium salt which can be replaced by potassium by adding 1 equivalent of KOH in aqueous medium.

Preparation of

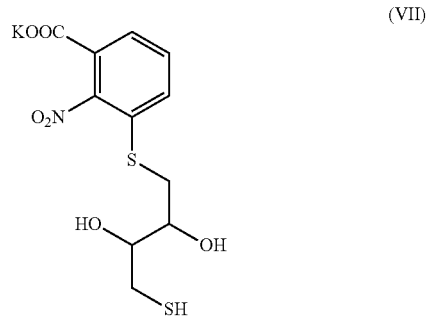

This compound can be prepared by starting with a mixture of 3-chloro-2-nitrobenzoic acid, dithiothreitol (DTT), and triethylamine in 2 mL of DMF. The mixture is then heated at 130 C for 20 hours. The reaction is then diluted with about 30 mL of 1 N HCl and extracted with ethyl acetate and dried over magnesium sulfate. The crude product thus obtained can be purified on HPLC to obtain the product as its triethylammonium salt which can be replaced by potassium by adding 1 equivalent of KOH in aqueous medium.

Preparation of N,N'-dimethyl-N,N'-bis(mercaptoacetyl)hydrazine (DMH)

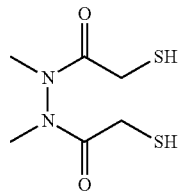
(VIII)

The compound was prepared by following the literature procedure (R. Singh and G. Whitesides, J. Org. Chem., vol 56, 2332-2337, 1991).

Preparation of

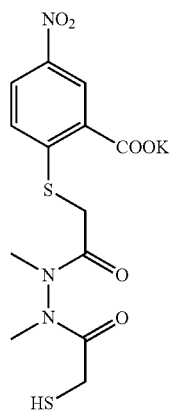
(IX)

This compound can be prepared by starting with a mixture of 2-chloro-5-nitrobenzoic acid, DMH, and triethylamine in 2 mL of DMF. The mixture is then heated at 50 C for 20 hours. The reaction is then diluted with about 30 mL of 1 N HCl and extracted with ethyl acetate and dried over magnesium sulfate. The crude product thus obtained can be purified on HPLC to obtain the product as its triethylammonium salt which can be replaced by potassium by adding 1 equivalent of KOH in aqueous medium.

Preparation of

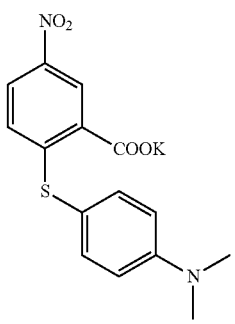
(X)

This compound can be prepared by starting with a mixture of 2-chloro-5-nitrobenzoic acid, 4-(dimethylamino)thiophenol, and triethylamine in 2 mL of DMF. The mixture is then heated at 130 C for 20 hours. The reaction is then diluted with about 30 mL of 1 N HCl and extracted with ethyl acetate and dried over magnesium sulfate. The crude product thus obtained can be purified on HPLC to obtain the product as its triethylammonium salt which can be replaced by potassium by adding 1 equivalent of KOH in aqueous medium Preparation of 1,1'-bis(6-deoxyascorbate)-4,4'-bipyridinium dibromide

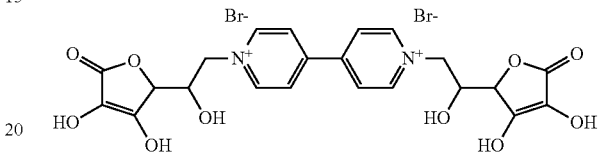
(IX)

The compound was prepared by reacting 4,4'-bipyridine with 6-bromo-6-deoxy-ascorbic acid (J. Med. Chem., E. Schmid, V. Figala, D. Roth and V. Ullrich, vol 36, 4021-4029, 1993).

Sequencing Performance of Two-Component ROXS Vs. Single Molecule ROXS Compound

Figure 5:
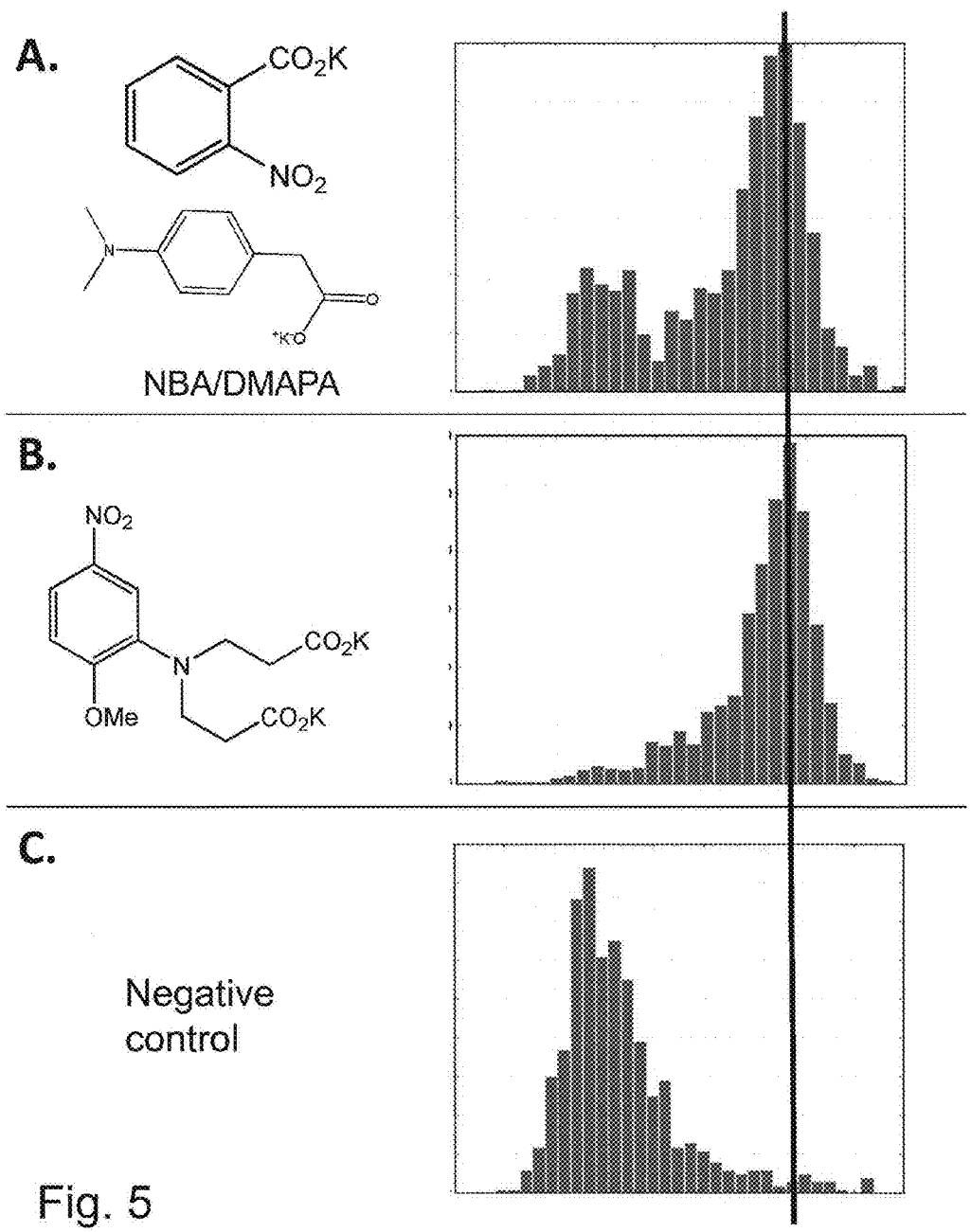
FIG. 5 shows accuracy distributions for sequencing reactions in the presence of a two-component ROXS (panel A), a single molecule ROXS compound (panel B), and in the absence of both a two-component ROXS and a single molecule ROXS compound (panel C).

Experiments were conducted using a Single Molecule Real Time (SMRT™) four-color sequencing instrument. (For detailed information on experiments, see, e.g., Eid, et al. (2009) Science 323:133-138.) Briefly, 30 nM of a phi29 polymerase enzyme modified for immobilization was mixed with 10 nM of a circular DNA template/primer complexes and other reaction mixture components, including Ca2+ salt and nucleotide analogs bearing a phospholinked fluorescent dye in MOPS buffer, pH 7.5. The mixture was incubated at 37° C. to allow formation of polymerase/template/primer complexes. The mixture was then diluted and an aliquot was added to a zero mode waveguide array, which was incubated to allow immobilization of the complexes within zero mode waveguides on the array. After washing, a solution comprising fluorescently labeled nucleotides was added and the array was placed inside the sequencing instrument. Sequencing was initiated and twenty minute reactions were monitored in real time. The fluorescence emissions were recorded, processed, and analyzed. FIG. 5 shows accuracy distributions for such reactions in the presence of a two-component ROXS (panel A), a single molecule ROXS compound (panel B), and in the absence of both a two-component ROXS and a single molecule ROXS compound (panel C). The chemical structures for each of these compounds is provided to the left of the distribution. Although the maxima of the accuracy distributions in the presence of a two-component or single molecule ROXS are similar, the concentrations of each required to achieve these accuracy distributions were quite different. The two-component ROXS was composed of 6 mM potassium nitrobenzoate (NBA) and 2.5 mM DMAPA, which the single molecule ROXS compound was present at a concentration of only 0.5 mM. The maxima of accuracy distributions in the presence of either a two-component or single molecule ROXS were significantly higher than when neither was present.

Sequencing Performance of Two Different Single Molecule ROXS Compounds

Figure 6:
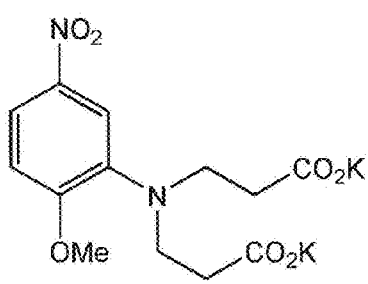
FIG. 6 shows accuracy distributions for these reactions in the presence of a two different single molecule ROXS compounds (panels A and B) and in the absence of both (panel C), as well as the chemical structures of the compounds.
Figure 6:
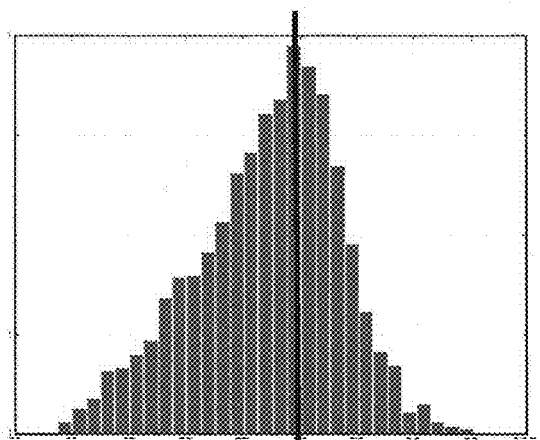
Figure 6:
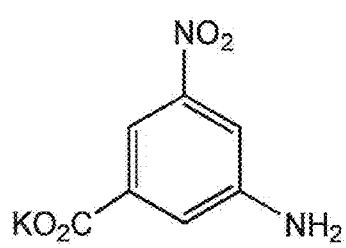
Figure 6:
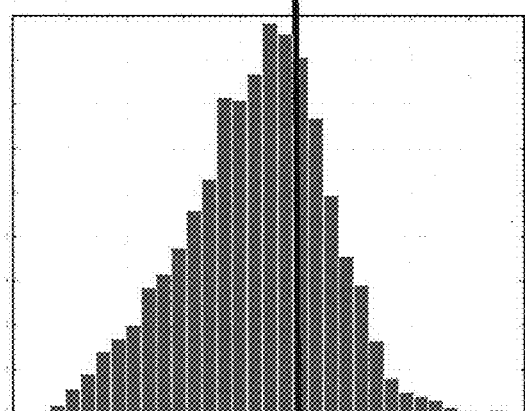
Figure 6:
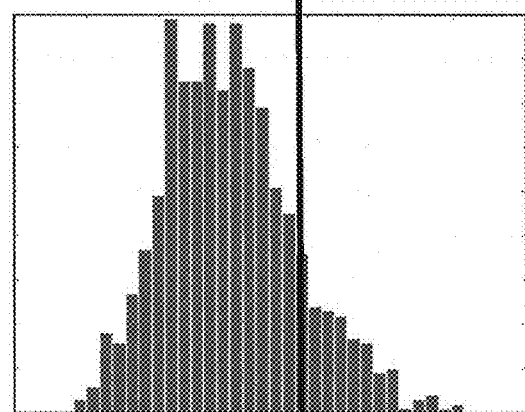

Experiments were conducted using a Single Molecule Real Time (SMRT™) four-color sequencing instrument as described above, and the data shown are based on seven minute reactions monitored in real time. FIG. 6 shows accuracy distributions for these reactions in the presence of a two different single molecule ROXS compounds (panels A and B) and in the absence of both (panel C), as well as the chemical structures of the compounds. The single molecule ROXS compounds were present at a concentration of 0.25 mM, which is notably even lower than the concentration of the single molecule ROXS compound used in the experiment described above. The maxima of the accuracy distributions in the presence of these single molecule ROXS were similar to one another, and were significantly higher than when neither was present.

Figure 7:
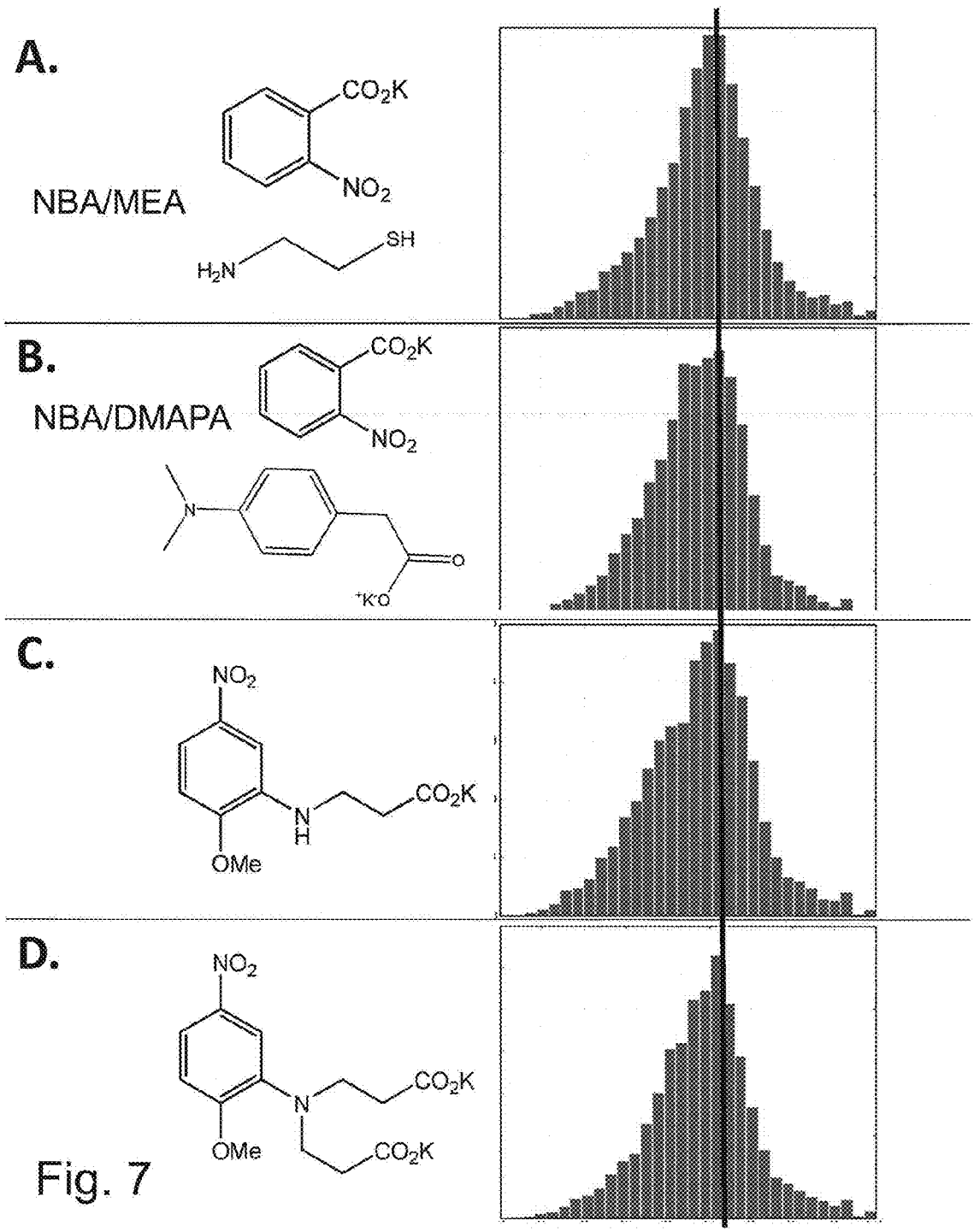
FIG. 7 shows accuracy distributions for these reactions in the presence of a two different two-component ROXS (panels A and B), and two different single molecule ROXS compounds (panels C and D).

Sequencing Performance of Two Different Two-Component ROXS Vs. Two Different Single Molecule ROXS Compounds Experiments were conducted using a Single Molecule Real Time (SMRT™) four-color sequencing instrument as described above, and the data shown are based on seven minute reactions monitored in real time. FIG. 7 shows accuracy distributions for these reactions in the presence of a two different two-component ROXS (panels A and B), and two different single molecule ROXS compounds (panels C and D). Panel A shows the accuracy distribution in the presence of 6 mM NBA and 2 mM mercaptoethylamine (MEA); panel B shows the accuracy distribution in the presence of 6 mM NBA and 2.5 mM DMAPA; and panels C and D show the accuracy distributions in the presence of 0.25 mM of two different single molecule ROXS compounds, whose chemical structures are provided to the left of the distributions. Although the maxima of the accuracy distributions in the presence of a two-component ROXS or single molecule ROXS compounds were similar, the concentrations of the single molecule ROXS compounds required to achieve these accuracy distributions were much lower than the concentrations of the two-component ROXS.

Figure 8:
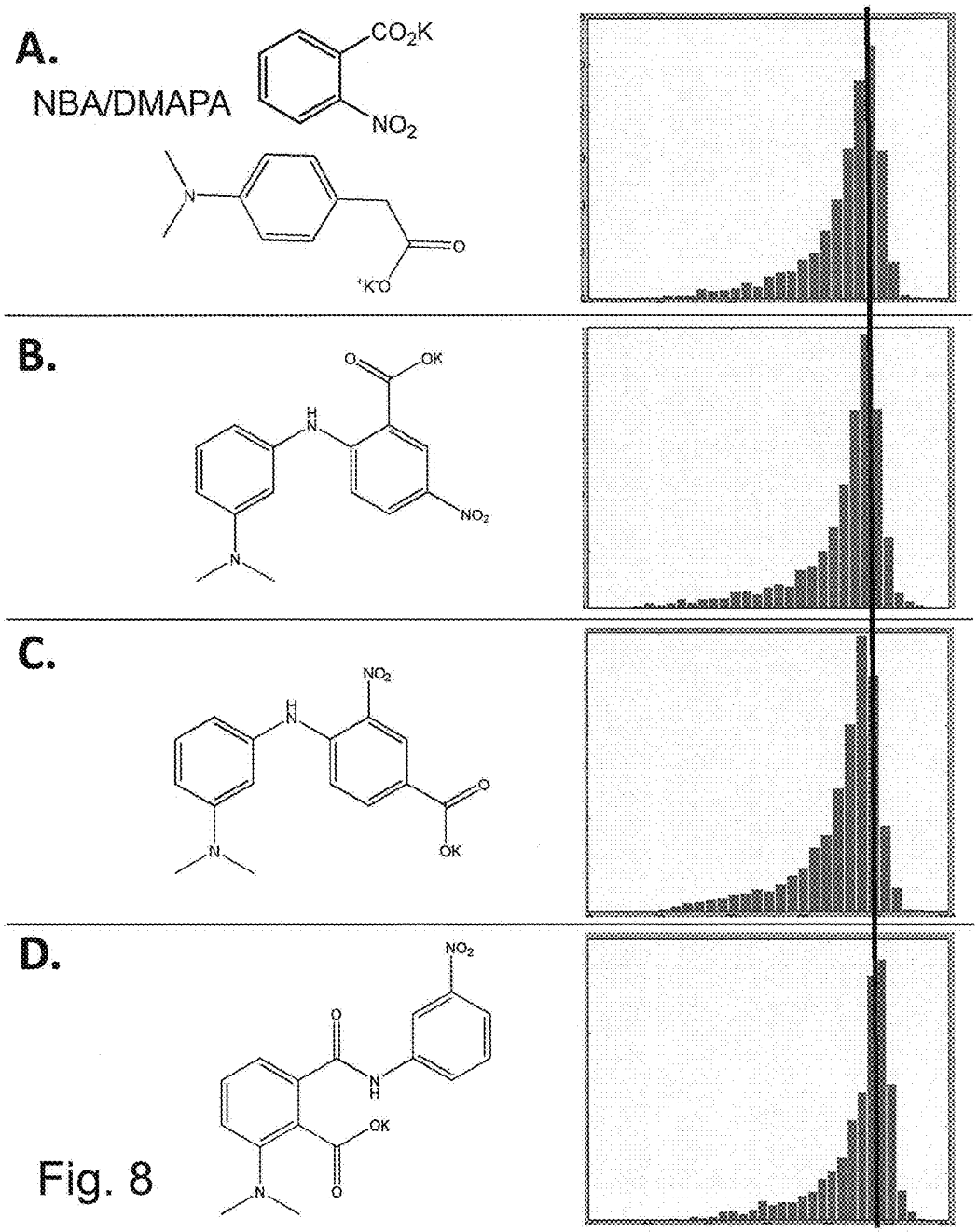
FIG. 8 shows accuracy distributions for these reactions in the presence of a two-component ROXS (panels A and E), and six different single molecule ROXS compounds (panels B, C, D, F, G, and H), as well as the chemical structures of the compounds.
Figure 8:
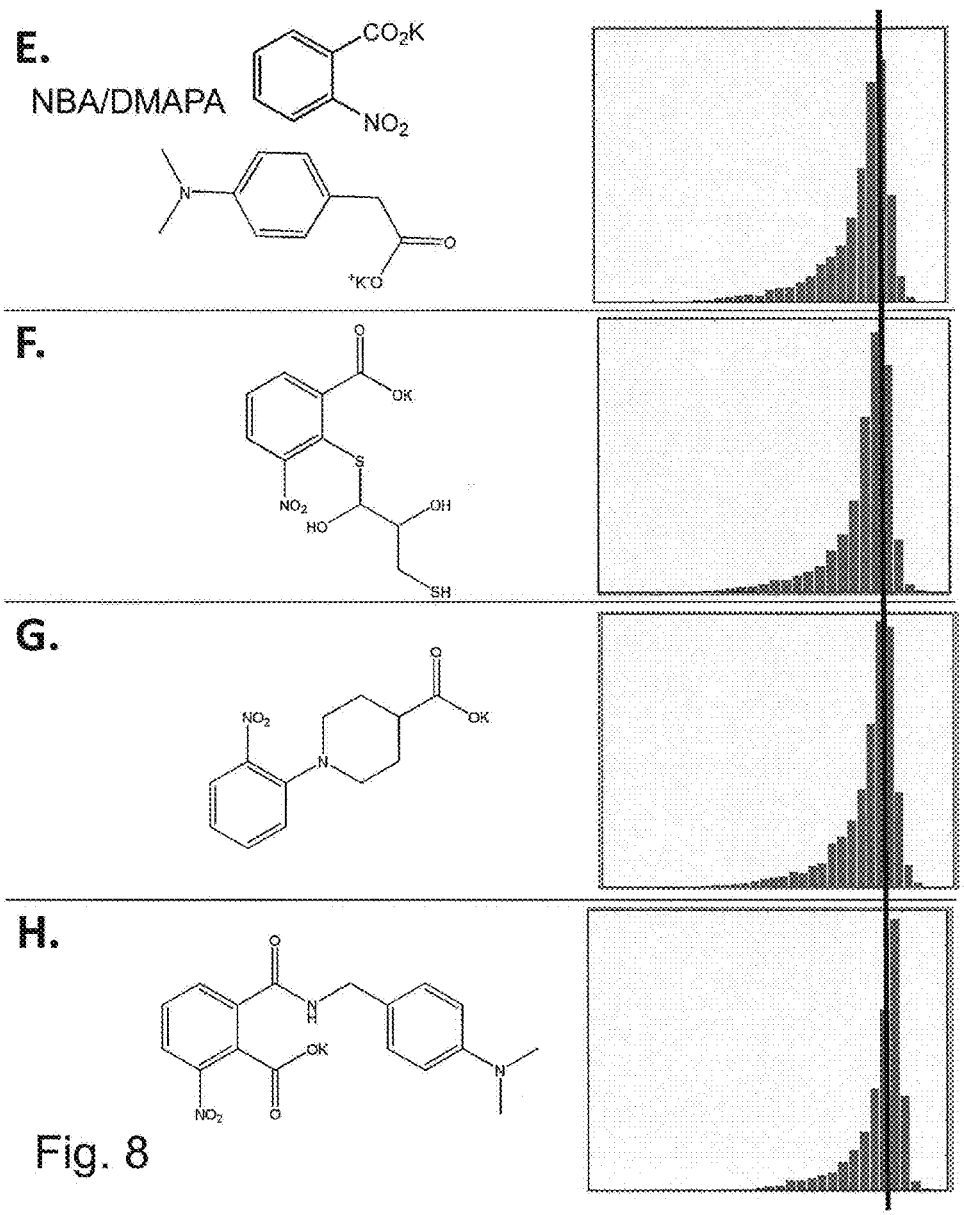

Sequencing Performance of a Two-Component ROXS Vs. Six Different Single Molecule ROXS Compounds Experiments were conducted using a Single Molecule Real Time (SMRT™) four-color sequencing instrument as described above, and the data shown are based on fifteen minute reactions monitored in real time. FIG. 8 shows accuracy distributions for these reactions in the presence of a two-component ROXS, and six different single molecule ROXS compounds, as well as the chemical structures of the compounds. Panels A and E show the accuracy distribution in the presence of 6 mM NBA and 2.5 mM DMAPA; and panels B, C, D, F, G, and H show the accuracy distributions in the presence of 0.25 mM of two different single molecule ROXS compounds, whose chemical structures are provided to the left of the distributions. Once again, although the maxima of the accuracy distributions in the presence of a two-component ROXS or single molecule ROXS compounds were similar in these experiments, the concentrations of the single molecule ROXS compounds required to achieve these accuracy distributions were much lower than the concentrations of the two-component ROXS.

Sequencing Performance of Four Different Single Molecule ROXS Compounds

Figure 9:
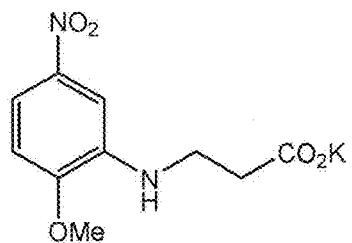
FIG. 9 shows accuracy distributions for these reactions in the presence of four different single molecule ROXS compounds (panels A-D), and the chemical structures of the compounds are provided to the left of the distributions.
Figure 9:
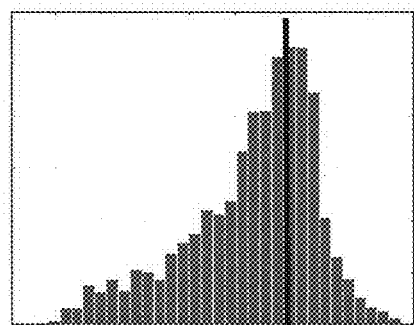
Figure 9:
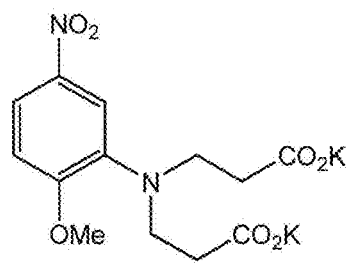
Figure 9:
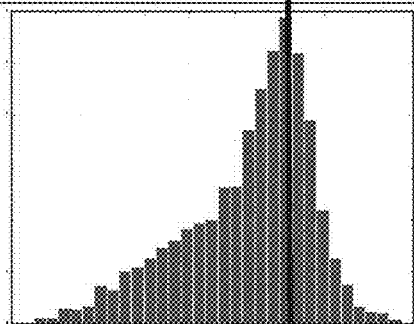
Figure 9:
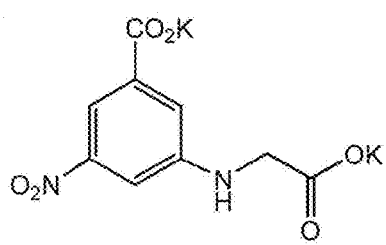
Figure 9:
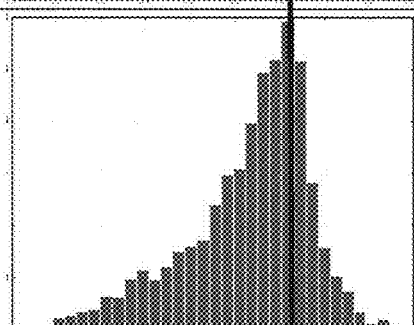
Figure 9:
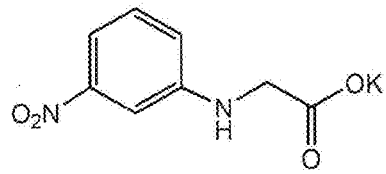
Figure 9:
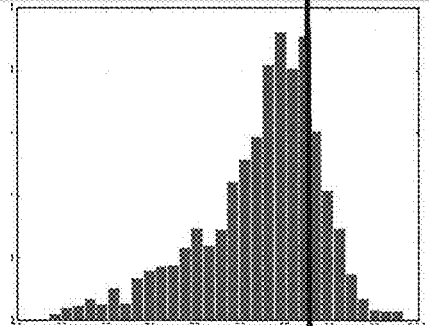

Experiments were conducted using a Single Molecule Real Time (SMRT™) four-color sequencing instrument as described above, and the data shown are based on seven minute reactions monitored in real time. FIG. 9 shows accuracy distributions for these reactions in the presence of four different single molecule ROXS compounds (panels A-D), and the chemical structures of the compounds are provided to the left of the distributions. The single molecule ROXS compounds are each present at a concentration of 0.25 mM, which is significantly lower than the typical concentrations of either member of a two-component ROXS. This experiment demonstrated that single molecule ROXS compounds having structural variations can perform similarly in improving the accuracy of sequencing reactions.

What is claimed is:
1. A method for protecting an enzyme from photo-induced damage in an illuminated reaction, the method comprising:
providing a reaction mixture comprising the enzyme, and a fluorescent or fluorogenic substrate for the enzyme, wherein interaction of the enzyme and the fluorescent or fluorogenic substrate under excitation illumination results in altered activity of the enzyme;
adding a photoprotective agent to the reaction mixture, wherein the photoprotective agent comprises a compound of a formula selected from the group consisting of:

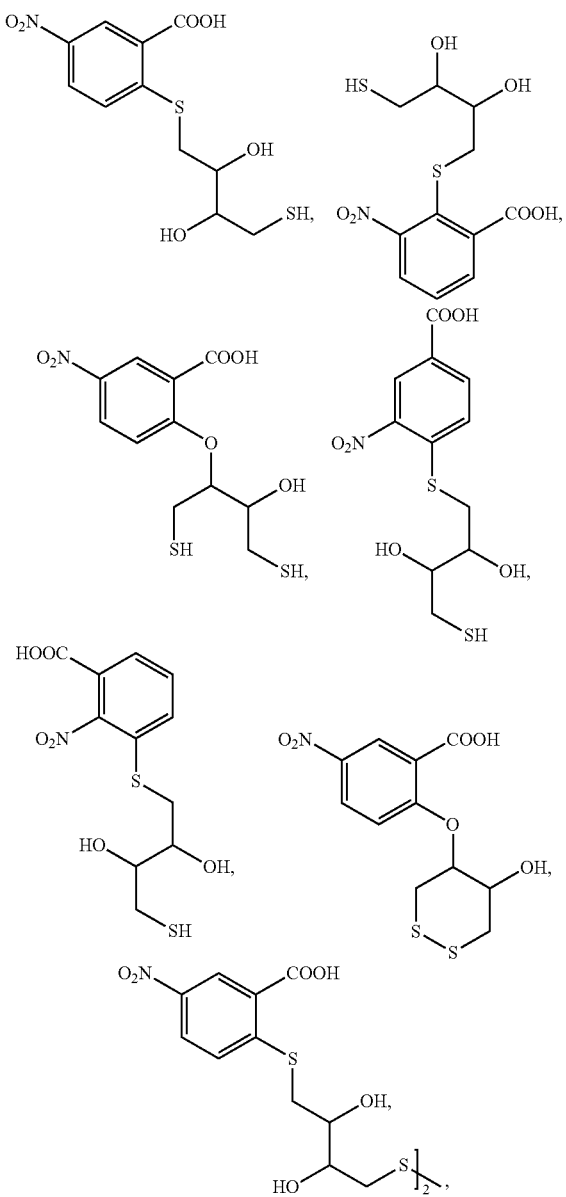

-continued
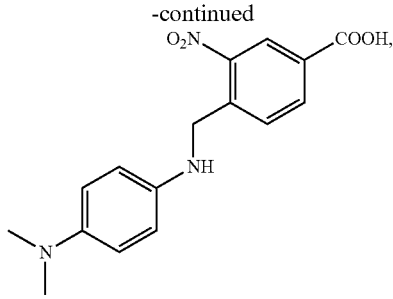
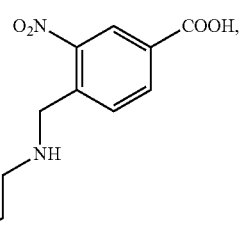
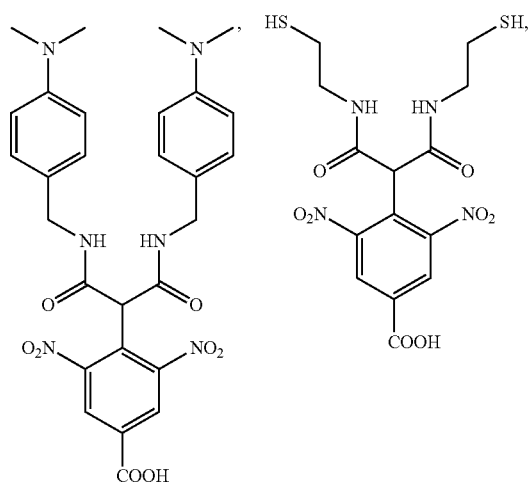
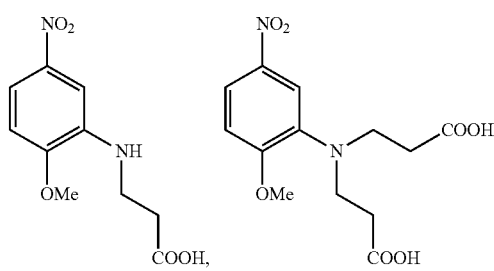
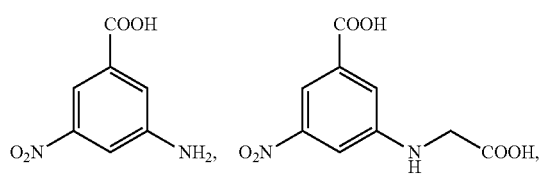
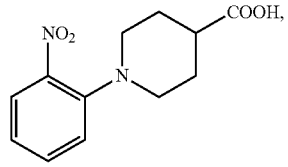
-continued
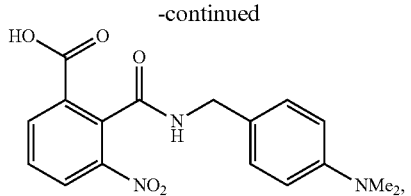
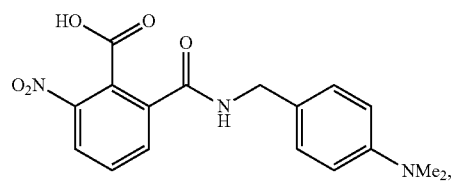
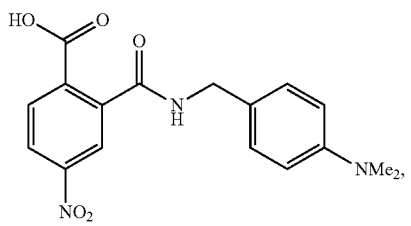
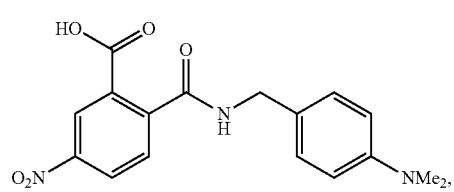
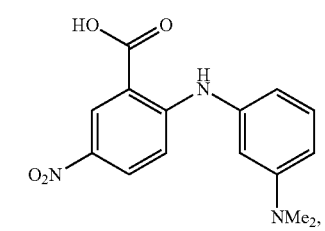
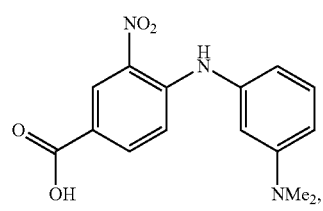
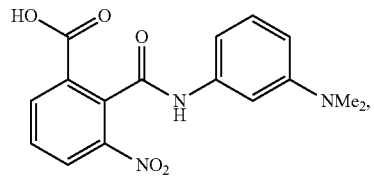
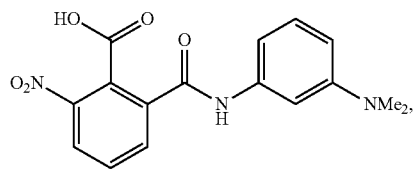

-continued

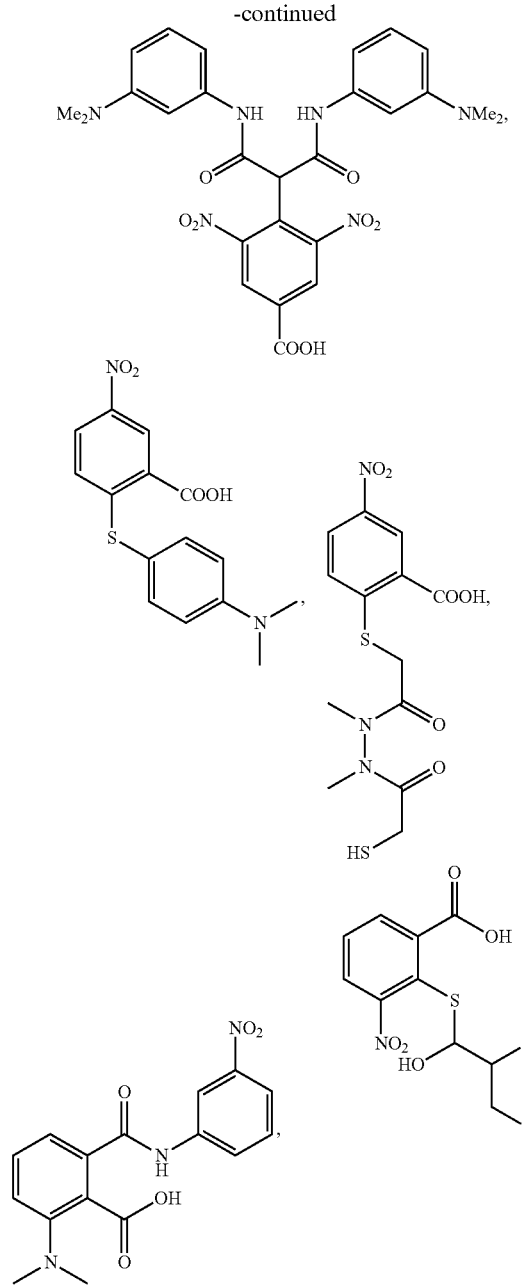

and a carboxylate salt thereof; and
illuminating the reaction mixture with an excitation illumination, wherein the photoprotective agent reduces an amount of photo-induced damage to the enzyme resulting from interaction of the enzyme with the fluorescent or fluorogenic substrate under the excitation illumination to an amount that is less than that which would occur in the absence of the photoprotective agent.

2. The method of claim 1, further comprising the step of monitoring a reaction between the enzyme and the fluorescent or fluorogenic substrate while illuminating the reaction mixture.

3. The method of claim 1, wherein said illuminated reaction is a base extension reaction.

4. The method of claim 1, wherein the enzyme is a polymerase or a ligase.

5. The method of claim 1, wherein the reaction mixture further comprises a template nucleic acid molecule.

6. The method of claim 1, wherein the fluorescent or fluorogenic substrate comprises a nucleoside polyphosphate or analog thereof.

7. The method of claim 1, wherein at least one component of the reaction mixture is confined within a zero mode waveguide.

8. The method of claim 1, wherein illuminating the reaction mixture comprises illuminating the reaction for a period of time that is less than a photo-induced damage threshold period, wherein the photo-induced damage threshold period is lengthened in the presence of the photoprotective agent.

9. The method of claim 1, wherein the carboxylate salt is a potassium salt.

10. A method for increasing the accuracy of an illuminated sequencing reaction, the method comprising:

providing a reaction mixture comprising a polymerase, a template nucleic acid, and a fluorescent or fluorogenic nucleotide or nucleotide analog;

adding a photoprotective agent to the reaction mixture, wherein the photoprotective agent comprises a compound of a formula selected from the group consisting of:

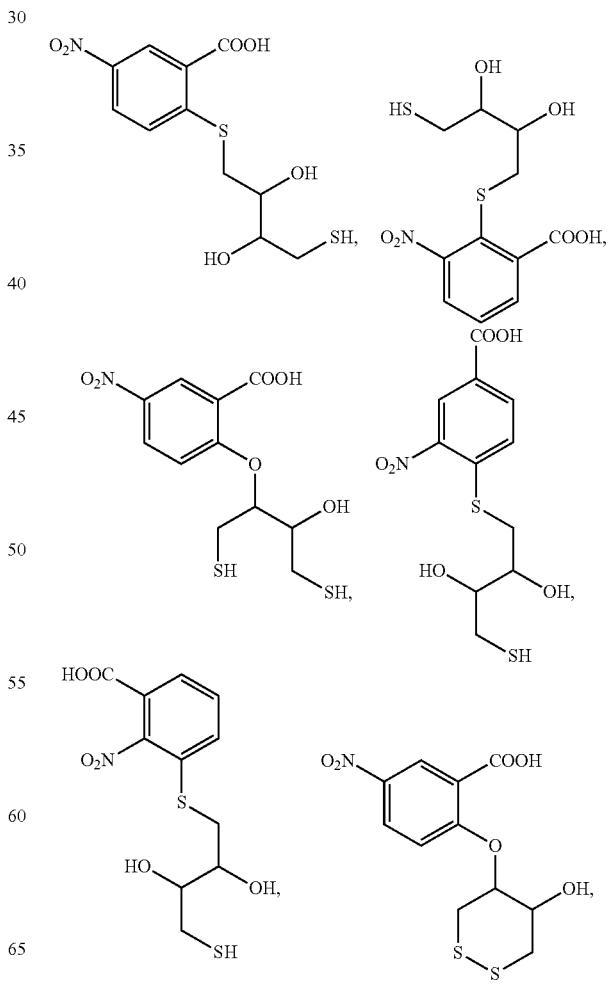

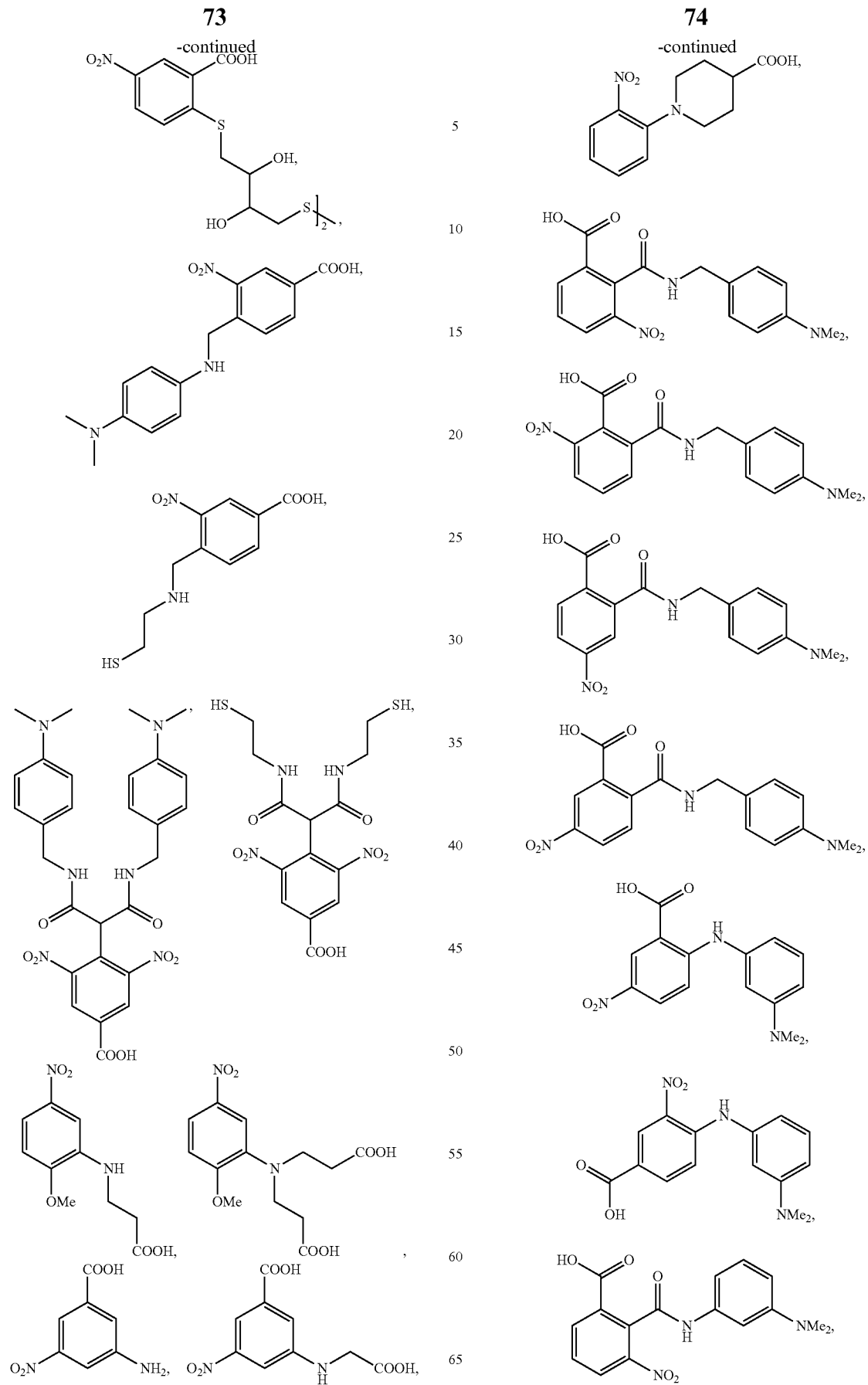

-continued

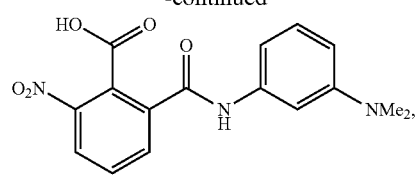
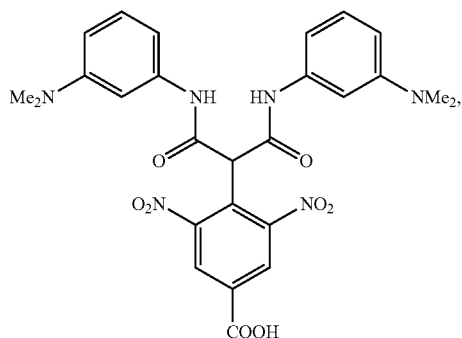
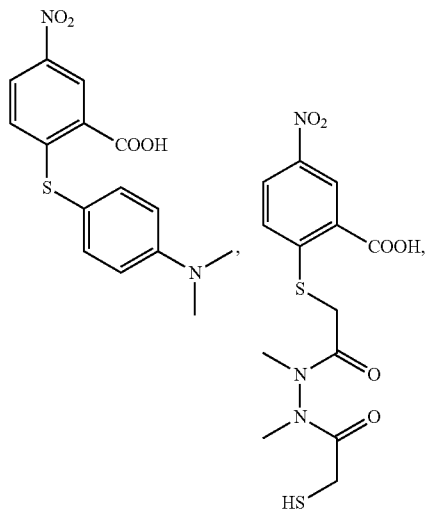

-continued

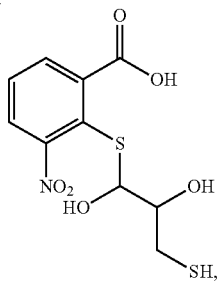

and a carboxylate salt thereof;
illuminating the reaction mixture with an excitation illumination; and
detecting emission signals from the reaction mixture, wherein the photoprotective agent enhances the detection, thereby increasing the accuracy of the sequencing reaction.

11. The method of claim 10, further comprising the step of monitoring a reaction between the polymerase and the fluorescent or fluorogenic nucleotide or nucleotide analog while illuminating the reaction mixture.

12. The method of claim 10, wherein the photoprotective agent reduces an amount of blinking or photobleaching of a dye within the fluorescent or fluorogenic nucleotide or nucleotide analog resulting from excitation of the dye by the excitation illumination to an amount that is less than that which would occur absent the photoprotective agent.

13. The method of claim 10, wherein said illuminated sequencing reaction is a base extension reaction.

14. The method of claim 10, wherein at least one component of the reaction mixture is confined within a zero mode waveguide.

15. The method of claim 10, wherein the polymerase is confined within a zero mode waveguide.

16. The method of claim 10, wherein the carboxylate salt is a potassium salt.

* * * * *